(12) United States Patent
Naor et al.

(10) Patent No.: US 10,611,819 B2
(45) Date of Patent: Apr. 7, 2020

(54) ISOLATED POLYPEPTIDES OF CD44 AND USES THEREOF

(71) Applicant: Yissum Research Development Company of the Hebrew University of Jerusalem Ltd., Jerusalem (IL)

(72) Inventors: David Naor, Tel-Aviv (IL); Lora Eshkar-Sebban, Beit Hasmonai (IL); Keren-Or Amar, Kiryat-Bialik (IL); Shmuel Cohen, Nehusha (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 84 days.

(21) Appl. No.: 15/324,768

(22) PCT Filed: Jul. 15, 2015

(86) PCT No.: PCT/IL2015/050732
§ 371 (c)(1),
(2) Date: Jan. 9, 2017

(87) PCT Pub. No.: WO2016/009436
PCT Pub. Date: Jan. 21, 2016

(65) Prior Publication Data
US 2017/0218045 A1    Aug. 3, 2017

Related U.S. Application Data

(60) Provisional application No. 62/024,719, filed on Jul. 15, 2014.

(51) Int. Cl.
*C07K 14/705* (2006.01)
*G01N 33/53* (2006.01)
*A61K 38/00* (2006.01)

(52) U.S. Cl.
CPC ........ *C07K 14/70585* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,331,647 A | 5/1982 | Goldenberg |
| 4,469,863 A | 9/1984 | Tso et al. |
| 4,476,301 A | 10/1984 | Imbach et al. |
| 4,666,828 A | 5/1987 | Gusella |
| 4,683,202 A | 5/1987 | Mullis |
| 4,761,406 A | 8/1988 | Flora et al. |
| 4,801,531 A | 1/1989 | Frossard |
| 4,816,567 A | 3/1989 | Cabilly et al. |
| 4,879,219 A | 11/1989 | Wands et al. |
| H735 H | 2/1990 | Srivastava et al. |
| 4,946,778 A | 8/1990 | Ladner et al. |
| 5,011,771 A | 4/1991 | Bellet et al. |
| 5,023,243 A | 6/1991 | Tullis |
| 5,034,506 A | 7/1991 | Summerton et al. |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci et al. |
| 5,272,057 A | 12/1993 | Smulson et al. |
| 5,276,019 A | 1/1994 | Cohen et al. |
| 5,278,302 A | 1/1994 | Caruthers et al. |
| 5,281,521 A | 1/1994 | Trojanowski et al. |
| 5,286,717 A | 2/1994 | Cohen et al. |
| 5,321,131 A | 6/1994 | Agrawal et al. |
| 5,399,676 A | 3/1995 | Froehler |
| 5,405,938 A | 4/1995 | Summerton et al. |
| 5,405,939 A | 4/1995 | Suhadolnik et al. |
| 5,434,257 A | 7/1995 | Matteucci et al. |
| 5,453,496 A | 9/1995 | Caruthers et al. |

(Continued)

FOREIGN PATENT DOCUMENTS

| | | |
|---|---|---|
| DE | 19708713 | 9/1998 |
| EP | 0239400 | 9/1987 |

(Continued)

OTHER PUBLICATIONS

Communication Pursuant to Article 94(3) EPC dated Jul. 27, 2018 From the European Patent Office Re. Application No. 15750822.7. (3 Pages).

(Continued)

*Primary Examiner* — Maher M Haddad

(57) ABSTRACT

Isolated polypeptides of CD44 are provided. Accordingly, there is provided an isolated polypeptide consisting of an amino acid sequence selected from the group consisting of SEQ ID NOs: 1-3. Also provided is an isolated end-capping modified polypeptide comprising an amino acid sequence selected from the group consisting of SEQ ID NO: 1-3, wherein the modified polypeptide comprises an anti-inflammatory activity. Also provided are compositions of matter, fusion proteins and pharmaceutical compositions and their use in the treatment of inflammatory disease.

12 Claims, 18 Drawing Sheets
(17 of 18 Drawing Sheet(s) Filed in Color)
Specification includes a Sequence Listing.

(56) References Cited

U.S. PATENT DOCUMENTS

| | | | |
|---|---|---|---|
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,489,677 A | 2/1996 | Sanghvi et al. |
| 5,519,126 A | 5/1996 | Hecht |
| 5,536,821 A | 7/1996 | Agrawal et al. |
| 5,539,082 A | 7/1996 | Nielsen et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,569,825 A | 10/1996 | Lonberg et al. |
| 5,571,799 A | 11/1996 | Tkachuk et al. |
| 5,587,361 A | 12/1996 | Cook et al. |
| 5,596,086 A | 1/1997 | Matteucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,625,126 A | 4/1997 | Lonberg et al. |
| 5,633,360 A | 5/1997 | Bischofberger et al. |
| 5,633,425 A | 5/1997 | Lonberg et al. |
| 5,661,016 A | 8/1997 | Lonberg et al. |
| 5,663,312 A | 9/1997 | Chaturvedula |
| 5,677,437 A | 10/1997 | Teng et al. |
| 5,677,439 A | 10/1997 | Weis et al. |
| 5,714,331 A | 2/1998 | Buchardt et al. |
| 5,719,262 A | 2/1998 | Buchardt et al. |
| 5,843,449 A | 12/1998 | Boots et al. |
| 5,935,577 A | 8/1999 | Weiner et al. |
| 5,951,982 A | 9/1999 | Zoeller |
| 5,961,977 A | 10/1999 | Hafler et al. |
| 6,010,865 A | 1/2000 | Ponta et al. |
| 6,019,970 A | 2/2000 | Ghent et al. |
| 6,077,509 A | 6/2000 | Weiner et al. |
| 6,303,374 B1 | 10/2001 | Zhang et al. |
| 6,645,504 B1 | 11/2003 | Weiner et al. |
| 6,703,361 B2 | 3/2004 | Weiner et al. |
| 6,790,447 B1 | 9/2004 | Wildner et al. |
| 7,534,605 B2 | 5/2009 | Naor et al. |
| 8,193,311 B2 | 6/2012 | Naor et al. |
| 2003/0108984 A1 | 6/2003 | Naor et al. |
| 2005/0215464 A1 | 9/2005 | Melnik et al. |
| 2006/0019340 A1 | 1/2006 | Naor et al. |
| 2009/0093053 A1 | 4/2009 | Naor et al. |
| 2009/0104202 A1 | 4/2009 | Naor et al. |
| 2011/0098215 A1* | 4/2011 | Agris ............... G01N 33/56988 514/3.8 |

FOREIGN PATENT DOCUMENTS

| | | |
|---|---|---|
| EP | 0368684 | 5/1990 |
| EP | 0438310 | 7/1991 |
| EP | 0501233 | 9/1992 |
| EP | 0519596 | 12/1992 |
| EP | 0538754 | 4/1993 |
| JP | 2008-500004 | 1/2008 |
| JP | 2013-502421 | 1/2013 |
| RU | 2359974 | 9/2007 |
| WO | WO 92/07075 | 4/1992 |
| WO | WO 92/22653 | 12/1992 |
| WO | WO 94/02610 | 2/1994 |
| WO | WO 94/09811 | 5/1994 |
| WO | WO 95/00658 | 1/1995 |
| WO | WO 95/03832 | 2/1995 |
| WO | WO 95/04547 | 2/1995 |
| WO | WO 00/75312 | 12/2000 |
| WO | WO 02/078524 | 10/2002 |
| WO | WO 03/014160 | 2/2003 |
| WO | WO 03/072606 | 9/2003 |
| WO | WO 2005/007700 | 1/2005 |
| WO | WO 2005/032454 | 4/2005 |
| WO | WO 2010/058396 | 5/2010 |
| WO | WO 2011/022335 | 2/2011 |
| WO | WO 2016/009436 | 1/2016 |

OTHER PUBLICATIONS

International Preliminary Report on Patentability dated Jan. 26, 2017 From the International Bureau of WIPO Re. Application No. PCT/IL2015/050732. (8 Pages).
Examination Report dated Oct. 31, 2018 From the Australian Government, IP Australia Re. Application No. 2015291151. (5 Pages).
Communication Pursuant to Article 94(3) EPC dated Dec. 21, 2009 From the European Patent Office Re. Application No. 04744979.8.
Communication Pursuant to Article 94(3) EPC dated Nov. 21, 2008 From the European Patent Office Re. Application No. 04744979.8.
Communication Pursuant to Article 96(2) EPC dated Dec. 5, 2003 From the European Patent Office Re. Application No. 00935449.9.
Examiner's Report dated May 14, 2010 From the Australian Government, IP Australia Re. Application No. 2006200123.
International Preliminary Report on Patentability dated Jan. 26, 2006 From the International Bureau of WIPO Re. Application No. PCT/IL2004/000639.
International Search Report and the Written Opinion dated Nov. 2, 2015 From the International Searching Authority Re. Application No. PCT/IL2015/050732.
International Search Report and the Written Opinion dated Mar. 9, 2010 From the International Searching Authority Re. Application No. PCT/IL2009/001086.
International Search Report dated Nov. 25, 2004 From the International Searching Authority Re. Application No. PCT/IL2004/000639.
International Preliminary Report on Patentability dated Jun. 3, 2011 From the International Bureau of WIPO Re. Application No. PCT/IL2009/001086.
Office Action dated Jul. 12, 2005 From the Israeli Patent Office Re. Application No. 130356.
Office Action dated Jul. 14, 2010 From the Israeli Patent Office Re. Application No. 173108 and Its Translation Into English.
Office Action dated Feb. 18, 2009 From the Israeli Patent Office Re. Application No. 173108.
Office Action dated Jan. 18, 2007 From the Israeli Patent Office Re. Application No. 130356.
Office Action dated Nov. 18, 2008 From the Israeli Patent Office Re. Application No. 130356 and Its Translation Into English.
Office Action dated Jan. 24, 2008 From the Israeli Patent Office Re. Application No. 130356.
Official Action dated May 5, 2009 From the US Patent and Trademark Office Re. U.S. Appl. No. 12/230,899.
Official Action dated Jun. 6, 2007 From the US Patent and Trademark Office Re. U.S. Appl. No. 11/130,206.
Official Action dated Nov. 6, 2006 From the US Patent and Trademark Office Re. U.S. Appl. No. 11/130,206.
Official Action dated Sep. 6, 2011 From the US Patent and Trademark Office Re. U.S. Appl. No. 13/021,807.
Official Action dated Nov. 10, 2011 From the US Patent and Trademark Office Re. U.S. Appl. No. 13/021,807.
Official Action dated Mar. 23, 2010 From the US Patent and Trademark Office Re. U.S. Appl. No. 12/230,899.
Official Action dated Jul. 31, 2009 From the US Patent and Trademark Office Re. U.S. Appl. No. 12/230,899.
Official Communication dated Oct. 9, 2006 From the European Patent Office Re. U.S. Appl. No. 06113988.7.
Partial European Search Report dated Oct. 9, 2006 From the European Patent Office Re. Application No. 06113988.7.
Requisition by the Examiner dated Apr. 12, 2011 From the Canadian Intellectual Property Office Re. Application No. 2,532,323.

(56) References Cited

OTHER PUBLICATIONS

Summons to Attend Oral Proceedings Pursuant to Rule 115(1) EPC dated Mar. 17, 2008 From the European Patent Office Re. Application No. 00935449.9.
Translation of Notice of Reason for Rejection dated Apr. 16, 2010 From the Japanese Patent Office Re. Application No. 2006-520103.
Written Opinion dated Nov. 25, 2004 From the International Searching Authority Re. Application No. PCT/IL2004/000639.
Abaza et al. "Effects of Amino Acid Sustitutions Outside an Antigenic Site on Protein Binding to Monoclonal Antibodies of Predetermined Specifity Obtained by Peptide Immuniation: Demonstration With Region 94-100 (Antigenic Site 3) of Myoglobin", Journal of Protein Chemistry, 11(5): 433-444, 1992.
Alexander et al. "Autoimmune Prostatitis: Evidence of T Cell Reactivity With Normal Prostatic Proteins", Urology, 50: 893-899, 1997.
Antoine et al. "Anti-Neuronal Antibodies and Central Nervous System Diseases: Contribution to Diagnosis and Pathophysiology", Reviews in Neurology, 156(1): 23-33, 2000.
Antoneli et al. "Extraocular Retinoblastoma: A 13-Year Experience", Cancer, 98: 1292-1298, 2003.
Barbas III et al. "Human Monoclonal Fab Fragments Derived From a Combinatorial Library Bind to Respiratory Syncytial Virus F Glycoprotein and Neutralize Infectivity", Proc. Natl. Acad. Sci. USA, 89: 10164-10168, 1992.
Bebbington et al. "High-Level Expression of a Recombinant Antibody From Myeloma Cells Using a Glutamine Synthetase Gene as an Amplifiable Selectable Marker", Bio/Technology, 10: 169-175, 1992.
Beerli et al. "Intracellular Expression of Single Chain Antibodies Reverts ErbB-2 Transformation", the Journal of Biological Chemistry, 269(39): 23931-23936, 1994.
Biocca et al. "Intracellular Immunization With Cytosolic Recombinant Antibodies", Bio/Technology, 12: 396-399, 1994.
Bird et al. "Single-Chain Antigen-Binding Proteins", Science, 242(4877): 423-426, 1988.
Boerner et al. "Production of Antigen-Specific Human Monoclonal Antibodies From in Vitro-Primed Human Splenocytes", the Journal of Immunology, 147(1): 86-95, 1991.
Braley-Mullen et al. "Early Requirement for B Cells for Development of Spntaneous Autoimmune Thyroiditis in NOD.H-2h4 Mice", the Journal of Immunology 165: 7262-7269, 2000.
Caporossi et al. "Autoimmune T-Cell Response to the CD4 Molecule in HIV-Infected Patients", Viral Immunology, 11(1): 9-17, 1998.
Carlson "A New Use for Intracellular Antibody Expression: Inactivation of Human Immunodeficiency Virus Type 1", Proc. Natl. Acad. Sci. USA, 90: 7427-7428, 1993.
Castano et al. "Type-I Diabetes: A Chronic Autoimmune Disease of Human, Mouse, and Rat", Annual Reviews in Immunology, 8: 647-679, 1990.
Chan et al. "The Central and Multiple Roles of B Cells in Lupus Pathogenesis", Immunological Reviews, 169: 107-121, 1999.
Chaudhary et al. "A Recombinant Single-Chain Immunotoxin Composed of Anti-Tac Variable Regions and a Truncated Diphtheria Toxin", Proc. natl. Acad. Sci. USA, 87: 9491-9494, 1990.
Chen et al. "Combined Intra- and Extracellular Immunization Against Human Immunodeficiency Virus Type 1 Infection With A Human Anti-Gp120 Antibody", Proc. Natl. Acad. Sci. USA, 91: 5932-5936, 1994.
Chen et al. "Intracellular Antibodies as a New Class of Therapeutic Molecules for Gene Therapy", Human Gene Therapy, 5: 595-601, 1994.
Cole et al. "Human Monoclonal Antibodies", Molecular and Cellular Biochemistry, 62: 109-120, 1984.
Cole et al. "The EBV-Hybridoma Technique and Its Application to Human Lung Cancer", Monclonal Antobodies and Cancer Therapy, p. 77-96, 1985.

Colman "Effects of Amino Acid Sequence Changes on Antibody-Antigen Interactions", Research in Immunology, 145(1): 33-36, 1994.
Coloma et al. "Novel Vectors for the Expression of Antibody Molecules Using Variable Regions Generated by Polymerase Chain Reaction", Journal of Immunological Methods, 152: 89-104, 1992.
Cross et al. "B Cells and Antibodies in CNS Demyelinating Disease", Journal of Neuroimmunology, 112: 1-14, 2001.
Cunha-Neto et al. "Autoimmunity in Chagas' Disease", Journal of Clinical Investigation, 98: 1709-1712, 1996.
Datta "Production of Pathogenic Antibodies: Cognate Interactions Between Autoimmune T and B Cells", Lupus, 7: 591-596, 1998.
Deshane et al. "Intracellular Single-Chain Antibosy Directed Against ErbB2 Down-Regulates Cell Surface ErbB2 and Exhibits A Selective Anti-Proliferative Effect in ErbB2 Overexpressing Cancer Cell Lines", Gene Therapy, 1: 332-337, 1994.
Diekman et al. "Anti-Sperm Antibodies From Infertile Patients and Their Cognate Sperm Antigens: A Review. Identity Between SAGA-1, the H6—3C4 Antigen, and CD52", American Journal of Reproductive Immunology, 43: 134-143, 2000.
Ding et al. "Partial Characterization of the MPM-2 Phosphoepitope", Experimental Cell Research, 231(1): 3-13, 1997.
Duan et al. "Potent Inhibition of Human Immunodeficiency Virus Type 1 Replication by an Intracellular Anti-Rev Single-Chain Antibody", Proc. Natl. Acad. Sci. USA, 91: 5075-5079, 1994.
Efremov et al. "The Pathologic Significance of the Immunoglobulins Expressed by Chronic Lymphcytic Leukemia B-Cells in the Development of Autoimmune Hemolytic Anemia", Leukemia and Lymphoma, 28: 285-293, 1998.
Englisch et al. "Chemically Modified Oligonucleotides as Probes and Inhibitors", Angewandte Chemie, International Edition in English, 30(6): 613-629, 1991.
Erikson et al. "Self-Reactive B Cells in Nonautoimmune and Autoimmune Mice", Immunologic Research, 17(1 & 2): 49-61, 1998.
Erlich et al. "Specific DNA Amplification", Nature, 331: 461-462, 1988.
Feist et al. "Diagnostic Importance of Anti-Proteasome Antibodies", International Archives of Allergy and Immunology, 123: 92-97, 2000.
Fingl et al. "General Principles", the Pharmacological Basis of Therapeutics, Ch.1(Sec.I): 1-46, 1975.
Fishwild et al. "High-Avidity Human IgGk Monoclonal Antibodies From a Novel Strain of Minilocus Transgenic Mice", Nature Biotechnology, 14: 845-851, 1996.
Flamholz et al. "Therapeutic Plasma Exchange for the Acute Management of the Catastrophic Antiphospholipid Syndrome: Beta2-Glycoprotein I Antibodies as a Marker of Response to Therapy", Journal of Clinical Apheresis, 14: 171-176, 1999.
Franco et al. "Liver-Derived T Cell Clones in Autoimmune Chronic Active Hepatitis: Accessory Cell function of Hepatocytes Expressing Class II Major Histocompatibility Complex Molecules", Clinical Immunology and Immunopathology, 54: 382-394, 1990.
Friedman et al. "BR96 sFv-PE40, A Potent Single-Chain Immunotoxin That Selectively Kills Carcinoma Cells", Cancer Research, 53: 334-339, 1993.
Gait "Oligoribonucleotides", Antisense Research and Applications, CRC Press, Chap.16: 289-302, 1993.
Garza et al. "Mechanism of Ovarian Autoimmunity: Induction of T Cell and Antibody Responses by T Cell Epitope Mimicry and Epitope Spreading", Journal of Reproductive Immunology, 37: 87-101, 1998.
Gloddek et al. "Induction of an Inner-Ear-Specific Autoreactive T-Cell Line for the Diagnostic Evaluation of an Autoimmune Disease of the Inner Ear", Annals NY Academy of Sciences, 830: 266-276, 1997.
Golan et al. "Expression of Extra Trinucleotide in CD44 Varaint of Rheumatoid Arthritis Patients Allows Generation of Disease-Specific Monoclonal Antibody", Journal of Autoimmunity, XP022064945, 28(2-3): 99-113, May 5, 2007.
Goodwin "A New Approach to the Problem of Targeting Specific Monoclonal Antibodies to Human Tumors Using Anti-Hapten Chimeric Antibodies", Nuclear Medical Biology, 16(6): 645-651, 1989.

(56) References Cited

OTHER PUBLICATIONS

Gussow et al. "Humanization of Monoclonal Antibodies", Methods in Enzymology, 203: 99-121, 1991.
Hara et al. "GammaDelta T Lymphcyte Clonality in Pure Red Blood Cell Aplasia. Response", Blood, 77(5): 1127, 1991.
Harlow et al. "Antibodies", a Laboratory Manuel, Cold Spring Harbor, p. 141-155, 1988.
Hiemstra et al. "Cytomegalovirus in Autoimmunity: T Cell Crossreactivity to Viral antigen and Autoantigen Glutamic Acid Decarboxylase", Proc. Natl. Acad. Sci. USA, 98(7): 3988-3991, 2001.
Hoogenboom et al. "By-Passing Immunisation. Human Antibodies From Synthetic Repertoires of Germline VH Gene Segments Rearranged In Vitro", Journal of Molecular Biology, 227: 381-388, 1992.
Hulme et al. "Strategy and Tactics in Receptor-Binding Studies", Chap.4: 63-119, 124-167, 172-176.
Inbar et al. "Localization of Antibody-Combining Sites Within the Variable Portions of Heavy and Light Chains", Proc. Natl. Acad. Sci. USA, 69(9): 2659-2662, 1972.
Infante et al. "Myasthenia Gravis and Its Animal Model: T Cell Receptor Expression in an Antibody Mediated Autoimmune Disease", International Review in Immunology, 18: 83-109, 1999.
Jones "T-Cell Autoimmunity in Primary Biliary Cirrhosis", Clinical Science, 91: 551-558, 1996.
Jones et al. "Replacing the Complementarity-Determining Regions in a Human Antibody With Those From a Mouse", Nature, 321: 522-525, 1986.
Kelly "T Cell Regulation of Autoimmune Interstitial Nephritis", Journal of the American Society of Nephrology, 1(2): 140-149, 1990.
Koehler et al. "Continuous Cultures of Fused Cells Secreting Antibody of Predefined Specificity", Nature, 256: 495-497, 1975.
Komminoth et al. "Correspondance to the Editor-in-Chief", AJP, 145(3): 742-744, 1994.
Komminoth et al. "Evaluation of Methods for Hepatitis C Virus Detection in Archival Liver Biopsies", Pathology Research Practice, 190: 1017-1025, 1994.
Koopman et al. "Activated Human Lymphocytes and Aggressive Non-Hodgkin's Lymphomas Express a Homologue of the Rat Metastasis-Associated Variant of CD44", Journal of Experimental Medicine, 177: 897-904, 1993. Abstract.
Kornberg "Anti-GM1 Ganglioside Antibodies: Their Role int he Diagnosis and Pathogenesis of Immune-Mediated Motor Neuropathies", Journal of Clinical Neuroscience, 7(3): 191-194, 2000.
Krenn et al. "Histopathology and Molecular Pathology of Synovial B-Lymphocytes in Rheumatoid Arthritis", Histology and Histopathology, 15: 791-798, 2000.
Kugelman et al. "The Core Protein of Epican, a Heparan Sulfate Proteoglycan on Keratinocytes, is an Alternative Form of CD44", Journal of Investigative Dermatology, 99(4): 381-385, 1992.
Kusunoki "Antiglycolipid Antibodies in Guillai-Barre Syndrome and Autoimmune Neuropathies", the American Journal of Medical Science, 319(4): 234-239, 2000.
Lacroix-Desmazes et al. "Natural Antibodies to Factor VIII", Seminars in Thrombosis and Hemostasis, 26(2): 157-165, 2000.
Landau et al. Harefuah, 138(2): 122-126, 2000. Hebrew Only!
Larrick et al. "PCR Amplification of Antibody Genes", Methods: A Companion to Methods in Enzymology, 2(2): 106-110, 1991.
Li et al. "Beta-Endorphin Omission Analogs: Dissociation of Immunoreactivity From Other Biological Activities", Proc. Natl. Acad. Sci. USA, 77(6): 3211-3214, 1980.
Lonberg et al. "Antigen-Specific Human Antibodies From Mice Comprising Four Distinct Genetic Modifications", Nature, 368: 856-859, 1994.
Lonberg et al. "Human Antibodies From Transgenic Mice", International Review in Immunology, 13: 65-93, 1995.
Maloney et al. "Monoclonal Anti-Idiotype Antibodies Against the Murine B Cell Lymphoma 38C13: Characterization and Use as Probes for the Biology of the Tumor in Vivo and in Vitro", Hybridoma, 4(3): 191-209, 1985.

Manns "Antibodies to Soluble Liver Antigen: Specific Marker of Autoimmune Hepatitis", Journal of Hepatology, 33: 326-328, 2000.
Marasco et al. "Intracellular Antibodies Against HIV-1 Envelope Protein for AIDS Gene Therapy", Human Gene Therapy, 9: 1627-1642, 1998.
Marks et al. "By-Passing Immunization. Human Antibodies From V-Gene Libraries Displayed on Phage", Journal of Molecular Biology, 222: 581-597, 1991.
Marks et al. "By-Passing Immunization: Building High Affinity Human Antibodies by Chain Shuffling", Bio/Technology, 10: 779-783. 1992.
Martegani et al. "Structural Variability of CD44v Molecules and Reliability of Immunodetection of CD44 Isoforms Using mAbs Specific for DC44 Variant Exon Products", American Journal of Pathology, 154(1): 291-300, Jan. 1999.
Matsuura et al. "Antiphospholipid Antibodies and Atherosclerosis", Lupus, 7(Suppl.2): S135-S139, 1998.
Mhashilkar et al. "Inhibition of HIV-1 Tat-Mediated LTR Transactivation and HIV-1 Infection by Anti-Tat Single Chain Intrabodies", The EMBO Journal, 14(7): 1542-1551, 1995.
Moccia "Two Cases of Autoimmune Thrombocytopenic Purpura Associated With Antiphospholipid Antibodies", Annali Italiani di Medicina Interna, 14(2): 114-117, 1999.
Morrison "Success in Specification", Nature, 368: 812-813, 1994.
Morrison "Transfectomas Provide Novel Chimeric Antibodies", Science, 229(4719): 1202-1207, 1985.
Mullis et al. "Specific Synthesis of DNA in Vitro Via a Polymerase-Catalyzed Chain Reaction", Methods in Enzymology, 155(Chap. 21): 335-350, 1987.
Nagaoki et al. "Anti-Thyroglobulin Antibodies", Nippon Rinsho, 57(8): 122-126, 1999.
Naor et al. "CD44 in Cancer", Critical Reviews in Clinical Laboratory Sciences, 39(5): 527-579, 2002.
Naor et al. "CD44 in Rheumatoid Arthritis", Arthritis Research Therapy, XP001152927, 5(3): 105-115, Jan. 1, 2003.
Naor et al. "CD44 Involvement in Autoimmune Inflammations. The Lesson to Be Learned From CD44-Targeting by Antibody or From Knockout Mice", Annals of the New York Academy of Sciences, XP009130167, 1110: 233-247, Sep. 2007. p. 240, § 1-p. 241, § 3.
Naor et al. "CD44: Structure, Function and Association With the Malignant Process", Advances in Cancer Research, 71: 241-319, 1997. p. 286, last §-p. 287, first §.
Naor et al. "Generation of Anti-CD44-Rheumatoid Arthritis-Specific Monoclonal Antibodies", Human Antibodies, Session 5: Autoimmunity, 13: 13-14, 2004. Abstract.
Nedvetzki et al. "A Mutation in a CD44 Variant of Inflammatory Cells Enhances the Mitogenic Interaction of FGF With Its Receptor", Journal of Clinical Investigation, XP001152920, 111(8): 1211-1220, Apr. 1, 2003. Abstract, p. 1212, col. 1, § 2, p. 1214, col. 1, § 3-col. 2, § 1., p. 1218, col. 2, § 2, p. 1219, col. 2, § 4, Fig.1.
Nedvetzki et al. "CD44 Involvement in Experimental Collagen-Induced Arthritis (CIA)", Journal of Autoimmunity, 13(1): 39-47, Aug. 1999. Abstract.
Nesbit et al. "Production of a Functional Monoclonal Antibody Recognizing Human Colorectal Carcinoma Cells From a Baculovirus Expression System", Journal of Immunological Methods, 151: 201-208, 1992.
Neuberger "Generating High-Avidity Human Mabs in Mice", Nature Biotechnology, 14: 826-827, 1996.
Ngo et al. "Computational Complexity, Protein Structure Prediction and the Levinthal Paradox", the Protein Folding Problem, Problem and Tertiary Structure Prediction, Chap.14: 491-494, 1994.
Nissim et al. "Antibody Fragments From a 'Single Pot' Phage Display Library as Immunochemical Reagents", The EMBO Journal, 13(3): 692-698, 1994.
Nobile-Orazio et al. "Diagnostic Relevance of Anti-Neural Antibodies in Dysimmune Neuropathies", Electroencephalograpy & Clinical Neurophysiology: From Receptors to Perception, EEG, Suppl.50: 419-427, 1999.
Noel "Les Auto-Anticorps 'Anti-Cytoplasme des Polynucleaires' (ANCA): Description et Role Immunopathologique", Annales de la Medicine Interne, 151(3): 178-183, 2000.

(56) References Cited

OTHER PUBLICATIONS

Nuovo et al. "Intracellular Localization of Polymerase Chain Reaction (PCR)-Amplified Hepatitis C cDNA", the American Journal of Surgical Pathology, 17(7): 683-690, 1993.
Oh et al. "A New Epitope Tag From Hepatitis B Virus PreS1 for Immunodetection, Localization and Affinity Purification of Recombinant Proteins", Journal of Immunological Methods, 283(1-2): 77-89, 2003.
Orgiazzi "Anti-TSH Receptor Antibodies in Clinical Practice", Endocrinology and Metabolism Clinics of North America, 29(2): 339-355, 2000.
Oron et al. "Animal Model and In Vitro Studies of Anti Neurofilament Antibodies Mediated Neurodegeneration in Alzheimer's Disease", Journal of Neural Transm, Suppl. 49: 77-84, 1997.
Oshima et al. "Autoimmune T Cell Recognition of Human Acetylcholine Receptor: The Sites of T Cell Recognition in Myasthenia Gravis on the Extracellular Part of the Alpha Subunit", European Journal of Immunology, 20: 2563-2569, 1990.
Owens et al. "The Genetic Engineering of Monoclonal Antibodies", Journal of Immunological Methods, 168: 149-165, 1994.
Pack et al. "Improved Bivalent Miniantibodies, With Identical Avidity as Whole Antibodies, Produced by High Cell Density Fermentation of *Escherichia coli*", Bio/Technology, 11: 1271-1277, 1993.
Ponta et al. "CD44: From Adhesion Molecules to Signalling Regulators", Nature Reviews: Molecular Cell Biology, 4: 33-45, Jan. 2003.
Porter "The Hydrolysis of Rabbit Gamma-Globulin and Antibodies With Crystalline Papain", Biochemical Journal, 73: 119-126, 1959.
Praprotnik et al. "Pathogenic Role of Anti-Endothelial Cell Antibodies in Systemic Vasculitis", Wiener Klinische Wochenschrift, the Middle European Journal of Medicine, 112(15-16): 660-664, 2000.
Presta "Antibody Engineering", Current Opinion in Structural Biology, 2: 593-596, 1992.
Renaudineau et al. "Anti-Endothelial Cell Antibodies in Systemic Sclerosis", Clinical and Diagnostic Laboratory Immunology, 6(2): 156-160, 1999.
Richardson et al. "Phenotypic Knockout of the High-Affinity Human Interleukin 2 Receptor by Intracellular Single-Chain Antibodies Against the Alpha Subunit of the Receptor", Proc. Natl. Acad. Sci. USA, 92: 3137-3141, 1995.
Riechmann et al. "Reshaping Human Antibodies for Therapy", Nature, 332" 323-329, 1988.
Rudikoff et al. "Single Amino Acid Substitution Altering Antigen-Binding Specificity", Proc. Natl. Acad. Sci. USA, 79: 1979-1983, 1982.
Saiki et al. "Enzymatic Amplification of B-Globin Genomic Sequences and Restriction Site Analysis for Diagnosis of Sickle Cell Anemia", Science, 230(4732): 1350-1354, 1985.
Sakata et al. "Autoimmune T-Cell Recognition Sites of Human Thyrotropin Receptor in Graves' Disease", Molecular and Cellular Endocrinology, 92: 77-82, 1993.
Sallah et al. "Gamma/Delta T-Cell Hepatosplenic Lymphoma: Review of the Literature, Diagnosis by Flow Cytometry and Concomitant Autoimmune Hemolytic Anemia", Annals in Hematology, 74: 139-142, 1997.
Sanghvi "Antisense Research and Applications", CRC Press, 276-278, 1993.
Screaton et al. "Genomic Structure of DNA Encoding the Lymphocyte Homing Receptor CD44 Reveals at Least 12 Alternatively Spliced Exons", Proc. Natl. Acad. Sci. USA, 89: 12160-12164, 1992.
Screaton et al. "Genomic Structure of DNA Encoding the Lymphocyte Homing Receptor CD44 Reveals at Least 12 Alternatively Spliced Exons", Proc. Natl. Acad. Sci. USA, 89: 12160-12164, 1992. Abstract.
Sebban et al. "The Involvement of CD44 and Its Nocel Ligand Galectin-8 in Apoptotic Regulation of Autoimmune Inflammation", the Journal of Immunology, XP009130170, 179(2): 1225-1235, Jul. 15, 2007.

Semple et al. "Differences in Serum Cytokine Levels in Acute and Chronic Autoimmune Thrombocytopenic Purpura: Relationship to Platelet Phenotype and Antiplatelet T-Cell Reactivity", Blood, 10: 4245-4254, 1996.
Shaheen et al. "Targeting Human Immunodeficiency Virus Type 1 Reverse Transcriptase by Intracellular Expression of Single-Chain Variable Fragments to Inhibit Early Stages of the Viral Life Cycle", Journal of Virology, 70(6): 3392-3400, 1996.
Shin et al. "Production and Properties of Chimeric Antibody Molecules", Methods in Enzymology, 178: 459-476, 1989.
Soderstrom et al. "Autoimmune T Cell Repertoire in Optic Neuritis and Multiple Sclerosis: T Cells Recognising Multiple Myelin Proteins Are Accumulated in Cerebrospinal Fluid", Journal in Neurological and Neurosurgical Psychiatry, 57: 544-551, 1994.
Strassburg et al. "Anti-Mitochondrial Antibodies and Other Immunological Tests in Primary Biliary Cirrhosis", European Journal of Gastroenterology & Hepatology, 11: 595-601, 1999.
Takamori et al. "Antibodies to Calcium Channel and Synaptotagmin in Lambert-Eaton Myasthenic Syndrome", the American Journal of the Medical Science, 319(4): 204-208, 2000.
Terunori "Idiopathic Myxedema and Blocking Type Antibodies to TSH Receptor", Nippon Rinsho, 57(8): 71-75, 1999.
Tincani et al. "Anti Beta2-Glycoprotein I Antibodies: Clinical Significance", Lupus, 7(Suppl.2): S107-S109, 1998.
Tisch et al. "Antigen-Specific Immunotherapy: Is It a Real Possibility to Combat T-Cell-Mediated Autoimmunity?", Proc. Natl. Acad. Sci. USA, 91: 437-438, 1994.
Turley et al. "RHAMM and CD44 Peptides: Analytic Tools and Potential Drugs", Frontiers in Bioscience, 17: 1775-1794, Jan. 1, 2012.
Vaarala "Antiphospholipid Antibodies and Myocardial Infarction", Lupus, 7(Suppl.2): S132-S134, 1998.
Van Regenmortel "Improving the Quality of Biacore-Based Affinity Measurements", Developments in Biologicals, 112: 141-151, 2003.
Verdrengh et al. "Administration of Antibodies to Hyaluronanreceptor (CD44) Delays the Start and Ameliorates the Severiy of Collagen II Arthritis", Scandinavian Journal of Immunology, 42: 353-358, 1995. Introduction.
Verhoeyen et al. "Reshaping Human Antibodies: Grafting an Antilysozyme Activity", Science, 239(4847): 1534-1536, 1988.
Vincent et al. "Antibodies Affecting Ion Channel Function in Acquired Neurmyotonia, in Seropositive and Seronegative Myasthenia Gravis, and in Antibody-Mediated Arthrogryposis Multiplex Congenita", Annals of the NY Academy of Sciences, 841: 482-496, 1998.
Voswinkel et al. "B Lymphocyte Involvement in Ankylosing Spondylitis: The Heavy Chain Variable Segment Gene Repertoire of B Lymphocytes From Germinal Center-Like Foci in the Synovial Membrane Indicates Antigen Selection", Arthritis Research, 3: 189-195, 2001.
Wallukat et al. "Agonist-Like Beta-Adrenoceptor Antibodies in Heart Failure", American Journal of Cardiology, 83: 75H-79H, 1999.
Weiner et al. "Binding and Cyrotoxicity Cahracteristics of the Bispecific Murine Monoclonal Antibody 2B1", The Journal of Immunology, 151(5): 2877-2886, 1993.
Werge et al. "Intracellular Immunization. Cloning and Intracellular Expression of A Monoclonal Antibody to the P21Ras Protein", FEBS Letters 274(1,2): 193-198, 1990.
Whitlow et al. "Single-Chain Fv Proteins and Their Fusion Proteins", Methods: A Companion to Methods in Enzymology, 2(2): 97-105, 1991.
Williams et al. "Anti-Tumor Necrosis Factor Ameliorates Joint Disease in Murine Collagen-Induced Arthritis", Proc. Natl. Acad. Sci. USA, 89: 9784-9788, 1992.
Winter et al. "Making Antibodies by Phage Display Technology", Annual Reviews in Immunology, 12: 433-455, 1994.
Yoo et al. "Epitope Especificity and T Cell Receptor Usage in Type II Collagen Induced Autoimmune Ear Disease", Cellular Immunology, 157: 249-262, 1994.
Zauli et al. "Auto-Antibodies in Hepatitis C", Biomedicine & Pharmacotherapy, 53: 234-241, 1999.

(56) References Cited

OTHER PUBLICATIONS

Zhang et al. "Membrane Heparan Sulfate Proteoglycan-Supported FGF2-FGFR1 Signaling", the Journal of Biological Chemistry, 276(45): 41921-41929, 2001.
Zheng et al. "Monoclonal Antibodies to CD44 and Their Influence on Hyaluronan Recognition", Journal of Cell Biology, 130(2): 485-495, 1995.
Zimmet "Antibodies to Glutamic Acid Decarboxylase in the Prediction of Insulin Dependency", Diabetes Research and Clinical Practice, 34(Suppl.): S125-S131, 1996.
Translation Dated Apr. 15, 2019 of Notice of Reasons for Rejection dated Mar. 26, 2019 From the Japan Patent Office Re. Application No. 2017-522751. (5 Pages).
Notice of Reasons for Rejection dated Mar. 26, 2019 From the Japan Patent Office Re. Application No. 2017-522751. (6 Pages).
Request for Examination dated Dec. 26, 2018 From the (Rospatent), Federal Government Institution of Industrial Property of the Federal Service of Intellectual Property, Patents and Trademark of the Russian Federation Re. Application No. 2017104284 and Its Translation Into English. (11 Pages).

* cited by examiner

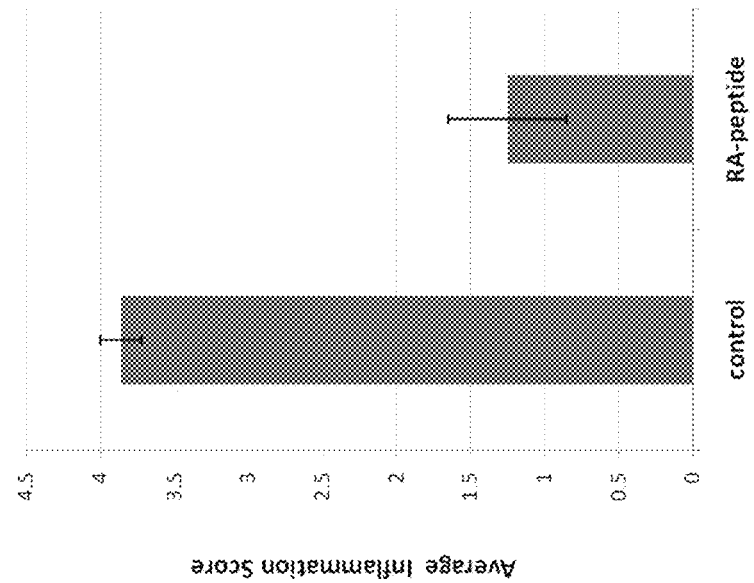
FIG. 3C
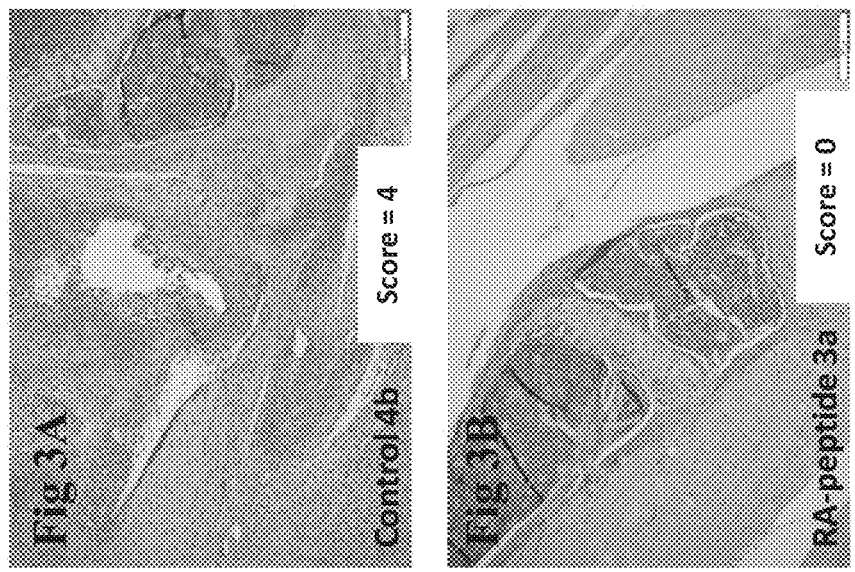
FIG. 3A
FIG. 3B

SEQUENCE LISTING

```
<160> NUMBER OF SEQ ID NOS: 29

<210> SEQ ID NO 1
<211> LENGTH: 5
<212> TYPE: PRT
<213> ORGANISM: Artificial sequence
<220> FEATURE:
<223> OTHER INFORMATION: Synthetic peptide

<400> SEQUENCE: 1

Met Thr Ala Asp Val
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic peptide

<400> SEQUENCE: 2

Met Thr Ala Asp Val Asp Arg
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Thr Arg Met Thr Ala Asp Val Asp Arg
1               5

<210> SEQ ID NO 4
<211> LENGTH: 5
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acylated-N terminus
<220> FEATURE:
<221> NAME/KEY: MISC_FEATURE
<222> LOCATION: (5)..(5)
<223> OTHER INFORMATION: C-Terminal Amidation

<400> SEQUENCE: 4

Met Thr Ala Asp Val
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acylated-N terminus
<220> FEATURE:
<221> NAME/KEY: MISC_FEATURE
<222> LOCATION: (7)..(7)
<223> OTHER INFORMATION: C-Terminal Amidation

<400> SEQUENCE: 5

Met Thr Ala Asp Val Asp Arg
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acylated-N terminus
<220> FEATURE:
<221> NAME/KEY: MISC_FEATURE
<222> LOCATION: (9)..(9)
<223> OTHER INFORMATION: C-Terminal Amidation

<400> SEQUENCE: 6

Thr Arg Met Thr Ala Asp Val Asp Arg
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acylated-N terminus
<220> FEATURE:
<221> NAME/KEY: MISC_FEATURE
<222> LOCATION: (7)..(7)
<223> OTHER INFORMATION: C-Terminal Amidation

<400> SEQUENCE: 7

Thr Met Asp Val Ala Asp Arg
1               5
```

<210> SEQ ID NO 8
<211> LENGTH: 5748
<212> TYPE: DNA
<213> ORGANISM: Homo sapiens

<400> SEQUENCE: 8

```
gagaagaaag ccagtgcgtc tctgggcgca ggggccagtg gggctcggag gcacaggcac      60
cccgcgacac tccaggttcc ccgacccacg tccctggcag ccccgattat ttacagcctc     120
agcagagcac ggggcggggg cagaggggcc cgcccgggag ggctgctact tcttaaaacc     180
tctgcgggct gcttagtcac agccccccct tgcttgggtgt gtccttcgct cgctccctcc    240
ctccgtctta ggtcactgtt ttcaacctcg aataaaaact gcagccaact tccgaggcag     300
cctcattgcc cagcggaccc cagcctctgc caggttcggt ccgccatcct cgtcccgtcc     360
tccgccggcc cctgccccgc gcccagggat cctccagctc ctttcgcccg cgccctccgt     420
tcgctccgga caccatggac aagttttggt ggcacgcagc ctggggactc tgcctcgtgc     480
cgctgagcct ggcgcagatc gatttgaata taacctgccg ctttgcaggt gtattccacg     540
tggagaaaaa tggtcgctac agcatctctc ggacggaggc cgctgacctc tgcaaggctt     600
tcaatagcac cttgcccaca atggcccaga tggagaaagc tctgagcatc ggatttgaga     660
cctgcaggta tgggttcata agagggcacg tggtgattcc ccggatccac cccaactcca     720
tctgtgcagc aaacaacaca ggggtgtaca tcctcacatc caacacctcc cagtatgaca     780
catattgctt caatgcttca gctccacctg aagaagattg tacatcagtc acagacctgc     840
ccaatgcctt tgatggacca attaccataa ctattgttaa ccgtgatggc acccgctatg     900
tccagaaagg agaatacaga acgaatcctg aagacatcta ccccagcaac cctactgatg     960
atgacgtgag cagcggctcc tccagtgaaa ggagcagcac ttcaggaggt tacatctttt    1020
acaccttttc tactgtacac cccatcccag acgaagacag tccctggatc accgacagca    1080
cagacagaat ccctgctacc actttgatga gcactagtgc tacagcaact gagacagcaa    1140
ccaagaggca agaaacctgg gattggtttt catggttgtt tctaccatca gagtcaaaga    1200
atcatcttca cacaacaaca caaatggctg gtacgtcttc aaataccatc tcagcaggct    1260
gggagccaaa tgaagaaaat gaagatgaaa gagacagaca cctcagtttt tctggatcag    1320
gcattgatga tgatgaagat tttatctcca gcaccatttc aaccacacca cgggcttttg    1380
accacacaaa acagaaccag gactggaccc agtggaaccc aagccattca aatccggaag    1440
tgctacttca caacccaca aggatgactg atgtagacag aaatggcacc actgcttatg    1500
aaggaaactg gaacccagaa gcacaccctc ccctcattca ccatgagcat catgaggaag    1560
aagagacccc acattctaca agcacaatcc aggcaactcc tagtagtaca acggaagaaa    1620
cagctaccca gaaggaacag tggtttggca acagatggca tgagggatat cgccaaacac    1680
ccaaagaaga ctcccattcg acaacaggga cagctgcagc ctcagctcat accagccatc    1740
caatgcaagg aaggacaaca ccaagcccag aggacagttc ctggactgat ttcttcaacc    1800
caatctcaca ccccatggga cgaggtcatc aagcaggaag aaggatggat atggactcca    1860
gtcatagtat aacgcttcag cctactgcaa atccaaacac aggtttggtg aagattgg      1920
acaggacagg acctctttca atgacaacgc agcagagtaa ttctcagagc ttctctacat    1980
cacatgaagg cttggaagaa gataaagacc atccaacaac ttctactctg acatcaagca    2040
ataggaatga tgtcacaggt ggaagaagag acccaaatca ttctgaaggc tcaactactt    2100
tactggaagg ttatacctct cattacccac acacgaagga aagcaggacc ttcatcccag    2160
```

-continued

```
tgacctcagc taagactggg tcctttggag ttactgcagt tactgttgga gattccaact    2220
ctaatgtcaa tcgttcctta tcaggagacc aagacacatt ccaccccagt gggggggtccc    2280
ataccactca tggatctgaa tcagatggac actcacatgg gagtcaagaa ggtggagcaa    2340
acacaacctc tggtcctata aggacacccc aaattccaga atggctgatc atcttggcat    2400
ccctcttggc cttggctttg attcttgcag tttgcattgc agtcaacagt cgaagaaggt    2460
gtgggcagaa gaaaaagcta gtgatcaaca gtggcaatgg agctgtggag acagaaaagc    2520
caagtggact caacggagag gccagcaagt ctcaggaaat ggtgcatttg gtgaacaagg    2580
agtcgtcaga aactccagac cagtttatga cagctgatga gacaaggaac ctgcagaatg    2640
tggacatgaa gattggggtg taacacctac accattatct tggaaagaaa caaccgttgg    2700
aaacataacc attacaggga gctgggcaca ttaacagatg caatgtgcta ctgattgttt    2760
cattgcgaat cttttttagc ataaaatttt ctactctttt tgttttttgt gttttgttct    2820
ttaaagtcag gtccaatttg taaaaacagc attgctttct gaattagggc cccaattaat    2880
aatcagcaag aatttgatcg ttccagttcc cacttggagg cctttcatcc ctcgggtgtg    2940
ctatggatgg cttctaacaa aaactacaca tatgtattcc tgatcgccaa cctttccccc    3000
accagctaag gacatttccc agggttaata gggcctggtc cctgggagga aatttgaatg    3060
ggtccatttt gcccttccat agcctaatcc ctgggcattg cttttccactg aggttggggg    3120
ttggggtgta ctagttacac atcttcaaca gacccctct agaaattttt cagatgcttc    3180
tgggagacac ccaaagggtg aagctattta tctgtagtaa actatttatc tgtgttttg    3240
aaatattaaa ccctggatca gtcctttgat cagtataatt ttttaaagtt actttgtcag    3300
aggcacaaaa gggtttaaac tgattcataa taaatatctg tacttcttcg atcttcacct    3360
tttgtgctgt gattcttcag tttctaaacc agcactgtct gggtccctac aatgtatcag    3420
gaagagctga gaatggtaag gagactcttc taagtcttca tctcagagac cctgagttcc    3480
cactcagacc cactcagcca aatctcatgg aagaccaagg agggcagcac tgttttttgtt    3540
ttttgttttt tgttttttt ttttgacact gtccaaaggt tttccatcct gtcctggaat    3600
cagagttgga agctgaggag cttcagcctc tttatggtt taatggccac ctgttctctc    3660
ctgtgaaagg ctttgcaaag tcacattaag tttgcatgac ctgttatccc tggggcccta    3720
tttcatagag gctggcccta ttagtgattt ccaaaaacaa tatggaagtg ccttttgatg    3780
tcttacaata agagaagaag ccaatggaaa tgaaagagat tggcaaaggg gaaggatgat    3840
gccatgtaga tcctgtttga cattttatg gctgtatttg taaacttaaa cacaccagtg    3900
tctgttcttg atgcagttgc tatttaggat gagttaagtg cctggggagt ccctcaaaag    3960
gttaaaggga ttcccatcat tggaatctta tcaccagata ggcaagttta tgaccaaaca    4020
agagagtact ggctttatcc tctaacctca tattttctcc cacttggcaa gtcctttgtg    4080
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
cacaaagcag aaagaagaag aaaagctcct gactaaatca gggctgggct tagacagagt    4320
tgatctgtag aatatcttta aaggagagat gtcaactttc tgcactattc ccagcctctg    4380
ctcctccctg tctaccctct cccctccctc tctccctcca cttcacccca caatcttgaa    4440
aaacttcctt tctcttctgt gaacatcatt ggccagatcc atttcagtg gtctggattt    4500
cttttttattt tcttttcaac ttgaaagaaa ctggacatta ggccactatg tgttgttact    4560
```

-continued

```
gccactagtg ttcaagtgcc tcttgttttc ccagagattt cctgggtctg ccagaggccc    4620
agacaggctc actcaagctc tttaactgaa aagcaacaag ccactccagg acaaggttca    4680
aaatggttac aacagcctct acctgtcgcc ccagggagaa aggggtagtg atacaagtct    4740
catagccaga gatggttttc cactccttct agatattccc aaaaagaggc tgagacagga    4800
ggttattttc aattttattt tggaattaaa tactttttc cctttattac tgttgtagtc     4860
cctcacttgg atatacctct gttttcacga tagaaataag ggaggtctag agcttctatt    4920
ccttggccat tgtcaacgga gagctggcca agtcttcaca aacccttgca acattgcctg    4980
aagtttatgg aataagatgt attctcactc ccttgatctc aagggcgtaa ctctggaagc    5040
acagcttgac tacacgtcat ttttaccaat gattttcagg tgacctgggc taagtcattt    5100
aaactgggtc tttataaaag taaaaggcca acatttaatt attttgcaaa gcaacctaag   5160
agctaaagat gtaattttc ttgcaattgt aaatcttttg tgtctcctga agacttccct     5220
taaaattagc tctgagtgaa aaatcaaaag agacaaaaga catcttcgaa tccatatttc    5280
aagcctggta gaattggctt ttctagcaga acctttccaa aagttttata ttgagattca    5340
taacaacacc aagaattgat tttgtagcca acattcattc aatactgtta tatcagagga   5400
gtaggagaga ggaaacattt gacttatctg gaaaagcaaa atgtacttaa gaataagaat    5460
aacatggtcc attcaccttt atgttataga tatgtctttg tgtaaatcat ttgttttgag    5520
ttttcaaaga atagcccatt gttcattctt gtgctgtaca atgaccactg ttattgttac   5580
tttgactttt cagagcacac ccttcctctg gtttttgtat atttattgat ggatcaataa   5640
taatgaggaa agcatgatat gtatattgct gagttgaaag cacttattgg aaaatattaa   5700
aaggctaaca ttaaaagact aaaggaaaca gaaaaaaaaa aaaaaaaa                5748
```

<210> SEQ ID NO 9
<211> LENGTH: 742
<212> TYPE: PRT
<213> ORGANISM: Homo sapiens

<400> SEQUENCE: 9

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160
```

```
Tyr Arg Thr Asn Pro Glu Asp Ile Tyr Pro Ser Asn Pro Thr Asp Asp
            165                 170                 175

Asp Val Ser Ser Gly Ser Ser Ser Glu Arg Ser Ser Thr Ser Gly Gly
        180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
        210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
                260                 265                 270

Ser Ala Gly Trp Glu Pro Asn Glu Glu Asn Glu Asp Glu Arg Asp Arg
            275                 280                 285

His Leu Ser Phe Ser Gly Ser Gly Ile Asp Asp Asp Glu Asp Phe Ile
        290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
                340                 345                 350

Thr Ala Tyr Glu Gly Asn Trp Asn Pro Glu Ala His Pro Pro Leu Ile
            355                 360                 365

His His Glu His His Glu Glu Glu Thr Pro His Ser Thr Ser Thr
        370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
            420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
        450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
        530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575
```

```
Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
            595                 600             605

Phe His Pro Ser Gly Gly Ser His Thr Thr His Gly Ser Glu Ser Asp
        610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
            675                 680                 685

Gly Ala Val Glu Asp Arg Lys Pro Ser Gly Leu Asn Gly Glu Ala Ser
            690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 10
<211> LENGTH: 2100
<212> TYPE: DNA
<213> ORGANISM: Homo sapiens

<400> SEQUENCE: 10
atggacaagt tttggtggca cgcagcctgg ggactctgcc tcgtgccgct gagcctggcg     60
cagatcgatt tgaatataac ctgccgcttt gcaggtgtat tccacgtgga aaaaatggt    120 cgctacagca tctctcggac ggaggccgct gacctctgca aggctttcaa tagcaccttg    180
cccacaatgg cccagatgga gaaagctctg agcatcggat ttgagacctg caggtatggg    240
ttcatagaag ggcacgtggt gattcccgg atccacccca actccatctg tgcagcaaac    300
aacacagggg tgtacatcct cacatccaac acctcccagt atgacacata ttgcttcaat    360
gcttcagctc cacctgaaga agattgtaca tcagtcacag acctgcccaa tgcctttgat    420
ggaccaatta ccataactat tgttaaccgt gatggcaccc gctatgtcca gaaggagaa    480 tacagaacga atcctgaaga catctacccc agcaacccta ctgatgatga cgtgagcagc    540
ggctcctcca gtgaaaggag cagcacttca ggaggttaca tcttttacac ctttttctact    600 gtacacccca tcccagacga agacagtccc tggatcaccg acagcacaga cagaatccct    660
gctaccagta cgtcttcaaa taccatctca gcaggctggg agccaaatga gaaaatgaa    720 gatgaaagag acagacacct cagttttttct ggatcaggca ttgatgatga tgaagatttt    780
atctccagca ccatttcaac cacaccacgg gcttttgacc acacaaaaca gaaccaggac    840
tggacccagt ggaacccaag ccattcaaat ccggaagtgc tacttcagac aaccacaagg    900
atgactgcag atgtagacag aaatggcacc actgcttatg aaggaaactg gaacccagaa    960
gcacaccctc ccctcattca ccatgagcat catgaggaag aagagacccc acattctaca   1020
agcacaatcc aggcaactcc tagtagtaca acggaagaaa cagctaccca gaaggaacag   1080
tggtttggca acagatggca tgagggatat cgccaaacac ccagagaaga ctcccattcg   1140
```

```
acaacaggga cagctgcagc ctcagctcat accagccatc caatgcaagg aaggacaaca    1200
ccaagcccag aggacagttc ctggactgat tcttcaacc caatctcaca ccccatggga    1260
cgaggtcatc aagcaggaag aaggatggat atggactcca gtcatagtac aacgcttcag   1320
cctactgcaa atccaaacac aggtttggtg aagatttgg acaggacagg acctctttca    1380
atgacaacgc agcagagtaa ttctcagagc ttctctacat cacatgaagg cttggaagaa    1440
gataaagacc atccaacaac ttctactctg acatcaagca ataggaatga tgtcacaggt    1500
ggaagaagag acccaaatca ttctgaaggc tcaactactt tactggaagg ttatacctct    1560
cattacccac acacgaagga aagcaggacc ttcatcccag tgacctcagc taagactggg    1620
tcctttggag ttactgcagt tactgttgga gattccaact ctaatgtcaa tcgttcctta    1680
tcaggagacc aagacacatt ccaccccagt gggggtccc ataccactca tggatctgaa    1740
tcagatggac actcacatgg gagtcaagaa ggtggagcaa acacaacctc tggtcctata    1800
aggacacccc aaattccaga atggctgatc atcttggcat ccctcttggc cttggctttg    1860
attcttgcag tttgcattgc agtcaacagt cgaagaaggt gtgggcagaa gaaaaagcta    1920
gtgatcaaca gtggcaatgg agctgtggag gacagaaagc caagtggact caacggagag    1980
gccagcaagt ctcaggaaat ggtgcatttg gtgaacaagg agtcgtcaga aactccagac    2040
cagtttatga cagctgatga gacaaggaac ctgcagaatg tggacatgaa gattggggtg    2100
```

<210> SEQ ID NO 11
<211> LENGTH: 700
<212> TYPE: PRT
<213> ORGANISM: Homo sapiens

<400> SEQUENCE: 11

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205
```

```
Ser Pro Trp Ile Thr Asp Ser Thr Asp Arg Ile Pro Ala Thr Thr Thr
    210                 215                 220
Ser Ser Asn Thr Ile Ser Ala Gly Trp Glu Pro Asn Glu Glu Asn Glu
225                 230                 235                 240
Asp Glu Arg Asp Arg His Leu Ser Phe Ser Gly Ser Gly Ile Asp Asp
                245                 250                 255
Asp Glu Asp Phe Ile Ser Ser Thr Ile Ser Thr Thr Pro Arg Ala Phe
            260                 265                 270
Asp His Thr Lys Gln Asn Gln Asp Trp Thr Gln Trp Asn Pro Ser His
        275                 280                 285
Ser Asn Pro Glu Val Leu Leu Gln Thr Thr Thr Arg Met Thr Ala Asp
290                 295                 300
Val Asp Arg Asn Gly Thr Thr Ala Tyr Glu Gly Asn Trp Asn Pro Glu
305                 310                 315                 320
Ala His Pro Pro Leu Ile His His Glu His His Glu Glu Glu Glu Thr
                325                 330                 335
Pro His Ser Thr Ser Thr Ile Gln Ala Thr Pro Ser Ser Thr Thr Glu
            340                 345                 350
Glu Thr Ala Thr Gln Lys Glu Gln Trp Phe Gly Asn Arg Trp His Glu
        355                 360                 365
Gly Tyr Arg Gln Thr Pro Arg Glu Asp Ser His Ser Thr Thr Gly Thr
370                 375                 380
Ala Ala Ala Ser Ala His Thr Ser His Pro Met Gln Gly Arg Thr Thr
385                 390                 395                 400
Pro Ser Pro Glu Asp Ser Ser Trp Thr Asp Phe Phe Asn Pro Ile Ser
                405                 410                 415
His Pro Met Gly Arg Gly His Gln Ala Gly Arg Arg Met Asp Met Asp
            420                 425                 430
Ser Ser His Ser Thr Thr Leu Gln Pro Thr Ala Asn Pro Asn Thr Gly
        435                 440                 445
Leu Val Glu Asp Leu Asp Arg Thr Gly Pro Leu Ser Met Thr Thr Gln
450                 455                 460
Gln Ser Asn Ser Gln Ser Phe Ser Thr Ser His Glu Gly Leu Glu Glu
465                 470                 475                 480
Asp Lys Asp His Pro Thr Thr Ser Thr Leu Thr Ser Ser Asn Arg Asn
                485                 490                 495
Asp Val Thr Gly Gly Arg Arg Asp Pro Asn His Ser Glu Gly Ser Thr
            500                 505                 510
Thr Leu Leu Glu Gly Tyr Thr Ser His Tyr Pro His Thr Lys Glu Ser
        515                 520                 525
Arg Thr Phe Ile Pro Val Thr Ser Ala Lys Thr Gly Ser Phe Gly Val
530                 535                 540
Thr Ala Val Thr Val Gly Asp Ser Asn Ser Asn Val Asn Arg Ser Leu
545                 550                 555                 560
Ser Gly Asp Gln Asp Thr Phe His Pro Ser Gly Ser His Thr Thr
                565                 570                 575
His Gly Ser Glu Ser Asp Gly His Ser His Ser Gln Glu Gly Gly
            580                 585                 590
Ala Asn Thr Thr Ser Gly Pro Ile Arg Thr Pro Gln Ile Pro Glu Trp
        595                 600                 605
Leu Ile Ile Leu Ala Ser Leu Leu Ala Leu Ala Leu Ile Leu Ala Val
610                 615                 620
```

| Cys | Ile | Ala | Val | Asn | Ser | Arg | Arg | Cys | Gly | Gln | Lys | Lys | Leu |
| --- | --- | --- | --- | --- | --- | --- | --- | --- | --- | --- | --- | --- | --- |
| 625 | | | | | 630 | | | | 635 | | | | 640 |

| Val | Ile | Asn | Ser | Gly | Asn | Gly | Ala | Val | Glu | Asp | Arg | Lys | Pro | Ser | Gly |
| --- | --- | --- | --- | --- | --- | --- | --- | --- | --- | --- | --- | --- | --- | --- | --- |
| | | | | 645 | | | | | 650 | | | | | 655 | |

| Leu | Asn | Gly | Glu | Ala | Ser | Lys | Ser | Gln | Glu | Met | Val | His | Leu | Val | Asn |
| --- | --- | --- | --- | --- | --- | --- | --- | --- | --- | --- | --- | --- | --- | --- | --- |
| | | | 660 | | | | | 665 | | | | | 670 | | |

| Lys | Glu | Ser | Ser | Glu | Thr | Pro | Asp | Gln | Phe | Met | Thr | Ala | Asp | Glu | Thr |
| --- | --- | --- | --- | --- | --- | --- | --- | --- | --- | --- | --- | --- | --- | --- | --- |
| | | | 675 | | | | 680 | | | | | 685 | | | |

| Arg | Asn | Leu | Gln | Asn | Val | Asp | Met | Lys | Ile | Gly | Val |
| --- | --- | --- | --- | --- | --- | --- | --- | --- | --- | --- | --- |
| | 690 | | | | | 695 | | | | | 700 |

<210> SEQ ID NO 12
<211> LENGTH: 531
<212> TYPE: DNA
<213> ORGANISM: Homo sapiens

<400> SEQUENCE: 12

```
ggcagggacc cgcagctcag ctacagcaca gatcagcacc atgaagcttc tcacgggcct      60
ggttttctgc tccttggtcc tgggtgtcag cagccgaagc ttcttttcgt tccttggcga     120
ggcttttgat ggggctcggg acatgtggag agcctactct gacatgagag aagccaatta     180
catcggctca gacaaatact ccatgctcgg gggaactat gatgctgcca aaggggacc       240
tgggggtgcc tggctgcag aagtgatcag cgatgccaga gagaatatcc agagattctt      300
tggccatggt gcggaggact cgctggctga tcaggctgcc aatgaatggg caggagtgg      360
caaagacccc aatcacttcc gacctgctgg cctgcctgag aaatactgag cttcctcttc     420
actctgctct caggagatct ggctgtgagg ccctcagggc agggatacaa agcggggaga    480
gggtacacaa tgggtatcta ataaatactt aagaggtgga atttgtggaa a              531
```

<210> SEQ ID NO 13
<211> LENGTH: 678
<212> TYPE: DNA
<213> ORGANISM: Homo sapiens

<400> SEQUENCE: 13

```
ggcagggacc cgcagctcag ctacagcaca gatcaggtga ggagcacacc aaggagtgat      60
ttttaaaact tactctgttt tctcttttccc aacaagatta tcatttcctt taaaaaaaat    120
agttatcctg gggcatacag ccataccatt ctgaaggtgt cttatctcct ctgatctaga    180
gagcaccatg aagcttctca cgggcctggt tttctgctcc ttggtcctgg gtgtcagcag    240
ccgaagcttc ttttcgttcc ttggcgaggc ttttgatggg gctcgggaca tgtggagagc    300
ctactctgac atgagagaag ccaattacat cggctcagac aaatacttcc atgctcgggg    360
gaactatgat gctgccaaaa ggggacctgg ggtgcctgg gctgcagaag tgatcagcga    420
tgccagagag aatatccaga gattctttgg ccatggtgcg gaggactcgc tggctgatca    480
ggctgccaat gaatggggca ggagtggcaa agacccaat cacttccgac ctgctggcct     540
gcctgagaaa tactgagctt cctcttcact ctgctctcag gagatctggc tgtgaggccc    600
tcagggcagg gatacaaagc ggggagaggg tacacaatgg gtatctaata aatacttaag    660
aggtggaatt tgtggaaa                                                   678
```

<210> SEQ ID NO 14
<211> LENGTH: 122
<212> TYPE: PRT
<213> ORGANISM: Homo sapiens

<400> SEQUENCE: 14

```
Met Lys Leu Leu Thr Gly Leu Val Phe Cys Ser Leu Val Leu Gly Val
1               5                   10                  15
Ser Ser Arg Ser Phe Phe Ser Phe Leu Gly Glu Ala Phe Asp Gly Ala
            20                  25                  30
Arg Asp Met Trp Arg Ala Tyr Ser Asp Met Arg Glu Ala Asn Tyr Ile
        35                  40                  45
Gly Ser Asp Lys Tyr Phe His Ala Arg Gly Asn Tyr Asp Ala Ala Lys
    50                  55                  60
Arg Gly Pro Gly Gly Val Trp Ala Ala Glu Ile Ser Asp Ala Arg
65                  70                  75                  80
Glu Asn Ile Gln Arg Phe Phe Gly His Gly Ala Glu Asp Ser Leu Ala
                85                  90                  95
Asp Gln Ala Ala Asn Glu Trp Gly Arg Ser Gly Lys Asp Pro Asn His
            100                 105                 110
Phe Arg Pro Ala Gly Leu Pro Glu Lys Tyr
        115                 120
```

<210> SEQ ID NO 15
<211> LENGTH: 607
<212> TYPE: DNA
<213> ORGANISM: Mus musculus

<400> SEQUENCE: 15

```
atagatcacc agatctgccc aggagacacc aggatgaagc tactcaccag cctggtcttc      60
tgctccctgc tcctgggagt ctgccatgga gggtttttt  catttgttca cgaggctttc     120
caagggctg  gggacatgtg gcgagcctac actgacatga aggaagctaa ctggaaaaac     180
tcagacaaat acttccatgc tcgggggaac tatgatgctg ctcaaagggg tcccggggga     240
gtctgggctg ctgagaaaat cagtgatgga agagaggcct ttcaggaatt cttcggcaga     300
ggacatgagg acaccattgc tgaccaggaa gccaacagac atggccgcag tggcaaagac     360
cccaattact acagacctcc tggactgcct gacaaatact gagcgtcctc ctattagctc     420
agtaggttgt gctgggggcc tgaggtgggg gtctgggctt cttcctacct aggaacactg     480
aagatgctct ctggggaaac attgtatatc tctcatgtgt gtatcccaca agggtttcag     540
aactgagtta ctcttgcagt agtaactgct tgaggaggag agggtaataa acagaaactt     600
ggaagtg                                                                607
```

<210> SEQ ID NO 16
<211> LENGTH: 2053
<212> TYPE: DNA
<213> ORGANISM: Homo sapiens

<400> SEQUENCE: 16

```
aggctcacta taaatagcag ccacctctcc ctggcagaca gggacccgca gctcagctac      60
agcacagatc agcaccatga gcttctcac  gggcctggtt ttctgctcct tggtcctgag     120
tgtcagcagc cgaagcttct tttcgttcct tggcgaggct tttgatgggg ctcgggacat     180
gtggagagcc tactctgaca tgagagaagc caattacatc ggctcagaca atacttcca     240
tgctcggggg aactatgatg ctgccaaaag gggacctggg ggtgcctggg ctgcagaagt     300
gatcagttta ttttcagctg aactgtagag agtgaaggaa gaagcctttt ttcttcactc     360
ctacatgacc caggcattga tccaggcaat gaagattcag tgtaaataac caccactaac     420
aagaccatgg cctttggaac ctgtgctaag aggcatggat gagctccctc agcatgtgga     480
```

| | |
|---|---|
| tggagactga agagaggtct gaaggctcag tgtggtgtct ccattctcta agaagtttgg | 540 |
| aggagaagct ggatacagca aaacagactg agaaggagca gctgttggga aaggaggaaa | 600 |
| actaggaaag catggtgttc cagaatccct gatggagata ttgattagta gtatcagatt | 660 |
| ctgcttagca gttgaggagt tcacctttgg cttaagcaac atggagtcat tgactatctc | 720 |
| gtgaaggtgg ttgcaggaga aggtctggag aactaaatgg agcagtgata agagagaatg | 780 |
| ggagatggta tgataggact cctggacacc ccagacatca atcaaaacac cacagacaag | 840 |
| aaggtgtgga tacaaaaact agcagttaga agaaataata gaaaatgaac tccaactact | 900 |
| tctgaaaaaa aagtaatgag ggcaattaat acattgaaga aagcctcaat aagtacaaca | 960 |
| gtgtagtact gacttatata tagaaaaaac ctgatcagtg gaaccaaatc ctcagaatta | 1020 |
| gacataagtg catatgagaa ttttgtatgt gataaaggtt gtatgttaac gtattaagta | 1080 |
| aaagacggac tattcaacaa atgggattgg tacaactggg tgaccatcta aaataacatc | 1140 |
| atgttgaaaa catactgtat atattacggt aggacaaatt ccaaatatgc taaatattta | 1200 |
| taaacaaata aggaaaatga taataataat attaacatta tctggtgaat ccatggaaaa | 1260 |
| ttcttttata gcccaaagta gggaaagctg caacaacaag gatggaactg gaggtcatta | 1320 |
| tgctaagtga aatcattcag gaacagaaag acaaacatca catgttctca cttatttgtg | 1380 |
| ggatctaaaa atcaaaacaa ttgaattcat ggagatagag aatagaagga tggttaccag | 1440 |
| aggctgggaa gggtagtggg gaggggggga gtgaggggag gtgaggatgg ttaatgagta | 1500 |
| ccaaaaaaat acttagaatg aataagagct agtatttgat agcacaacgg gggactatag | 1560 |
| tcagtaataa tttagctgta cattgtaaaa taaccaaaag agtataattg gattatttgt | 1620 |
| aacacaaagg ataaatgctt gagggatgg atacccaatt ttccatgatg tgattattgc | 1680 |
| gcattgcatg gctgtaccaa aatatctcat gtaccccata attatataca cctactatgt | 1740 |
| acccacaaaa aatttttaaa aaggaatgaa ataaaaacat ttgagtttaa gaaaaccaca | 1800 |
| aaaaaacaaa gtagggaaag ctcttcaaat actatgaaat tgagaagaca actaaagaaa | 1860 |
| atattaataa agacaagaac ataaataatt tctttggcag aacataagcc atcataatca | 1920 |
| gaagataaat aagctgggaa aaatatttgt aactcatatc ctagataaca tactcatttt | 1980 |
| ccctgtatat aaaaagtttc tctaatgtga taaataaaaa cacaataaac cagtaaaaaa | 2040 |
| tgaaaaaaaa aaa | 2053 |

<210> SEQ ID NO 17
<211> LENGTH: 594
<212> TYPE: DNA
<213> ORGANISM: Homo sapiens

<400> SEQUENCE: 17

| | |
|---|---|
| aggctcacta taaatagcag ccacctctcc ctggcagaca gggacccgca gctcagctac | 60 |
| agcacagatc agcaccatga agcttctcac gggcctggtt ttctgctcct tggtcctgag | 120 |
| tgtcagcagc cgaagcttct tttcgttcct tggcgaggct tttgatgggg ctcgggacat | 180 |
| gtggagagcc tactctgaca tgagagaagc caattacatc ggctcagaca aatacttcca | 240 |
| tgctcggggg aactatgatg ctgccaaaag gggacctggg ggtgcctggg ctgcagaagt | 300 |
| gatcagcaat gccagagaga atatccagag actcacaggc cgtggtgcgg aggactcgct | 360 |
| ggccgatcag gctgccaata atggggcag gagtggcaga gaccccaatc acttccgacc | 420 |
| tgctggcctg cctgagaaat actgagcttc ctcttcactc tgctctcagg agacctggct | 480 |

```
atgaggccct cggggcaggg atacaaagtt agtgaggtct atgtccagag aagctgagat      540
atggcatata ataggcatct aataaatgct taagaggtgg aatttgttga aaca            594
```

<210> SEQ ID NO 18
<211> LENGTH: 122
<212> TYPE: PRT
<213> ORGANISM: Homo sapiens

<400> SEQUENCE: 18

```
Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
            20                  25                  30

Arg Asp Met Trp Arg Ala Tyr Ser Asp Met Arg Glu Ala Asn Tyr Ile
        35                  40                  45

Gly Ser Asp Lys Tyr Phe His Ala Arg Gly Asn Tyr Asp Ala Ala Lys
    50                  55                  60

Arg Gly Pro Gly Gly Val Trp Ala Ala Glu Ala Ile Ser Asp Ala Arg
65                  70                  75                  80

Glu Asn Ile Gln Arg Phe Phe Gly His Gly Ala Glu Asp Ser Leu Ala
                85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120
```

<210> SEQ ID NO 19
<211> LENGTH: 610
<212> TYPE: DNA
<213> ORGANISM: Mus musculus

<400> SEQUENCE: 19

```
atagaccacc agatctgccc aggagacacc agcaggatga agctactcac cagcctggtc      60
ttctgctccc tgctcctggg agtctgccat ggagggtttt tttcatttat tggggaggct     120
ttccaagggg ctggagacat gtggcgagcc tacactgaca tgaaggaagc tggctggaaa     180
gatggagaca atacttcca tgctcggggg aactatgatg ctgcccaaag gggtcccggg      240
ggagtctggg ctgctgagaa aatcagtgat gcaagagaga gctttcagga attcttcggc    300
agaggacacg aggacaccat ggctgaccag gaagccaaca catggccg cagtggcaaa       360 gaccccaatt actacagacc tcctggactg cctgccaaat actgagagtc ctcctattag    420
ttcagaaggc tgtgttgggg tcctgagggt ggggtctggg cttcctatct aggaacactg    480
aagatgctct ctggggcaac atagtatacc tctcatgtgt gtatcccaca agggtttcag    540
aatggagtta ctcgagcagt agtaactgct tgaggaggag agggtaataa acaggaactt    600
ggaagtggat                                                             610
```

<210> SEQ ID NO 20
<211> LENGTH: 675
<212> TYPE: DNA
<213> ORGANISM: Homo sapiens

<400> SEQUENCE: 20

```
ggatttaaaa ccgttctccc attaatgcca aagccagcag aggtaccaac tatagctcca      60
cggccagaag ataccagcag ctctgccttt actgaaattt catctggaga aaggtccaca     120
gcacaatgag gcttttcaca ggcattgttt tctgctcctt ggtcatggga gtcaccagtg     180
```

```
aaagctggcg ttcgttttc aaggaggctc tccaagggt tggggacatg ggcagagcct    240
attgggacat aatgatatcc aatcaccaaa attcaaacag atatctctat gctcggggaa    300
actatgatgc tgcccaaaga ggacctgggg gtgtctgggc tgctaaactc atcagccgtt    360
ccagggtcta tcttcaggga ttaatagact gctatttatt tggaaacagc agcactgtat    420
tggaggactc gaagtccaac gagaaagctg aggaatgggg ccggagtggc aaagaccccg    480
accgcttcag acctgacggc ctgcctaaga aatactgagc ttcctgctcc tctgctctca    540
gggaaactgg gctgtgagcc acacacttct ccccccagac agggacacag ggtcactgag    600
ctttgtgtcc ccaggaactg gtatagggca cctagaggtg ttcaataaat gtttgtcaaa    660
ttgaaaaaaa aaaaa    675
```

<210> SEQ ID NO 21
<211> LENGTH: 130
<212> TYPE: PRT
<213> ORGANISM: Homo sapiens

<400> SEQUENCE: 21

```
Met Arg Leu Phe Thr Gly Ile Val Phe Cys Ser Leu Val Met Gly Val
1               5                   10                  15

Thr Ser Glu Ser Trp Arg Ser Phe Phe Lys Glu Ala Leu Gln Gly Val
            20                  25                  30

Gly Asp Met Gly Arg Ala Tyr Trp Asp Ile Met Ile Ser Asn His Gln
        35                  40                  45

Asn Ser Asn Arg Tyr Leu Tyr Ala Arg Gly Asn Tyr Asp Ala Ala Gln
    50                  55                  60

Arg Gly Pro Gly Gly Val Trp Ala Ala Lys Leu Ile Ser Arg Ser Arg
65                  70                  75                  80

Val Tyr Leu Gln Gly Leu Ile Asp Cys Tyr Leu Phe Gly Asn Ser Ser
                85                  90                  95

Thr Val Leu Glu Asp Ser Lys Ser Asn Glu Lys Ala Glu Glu Trp Gly
            100                 105                 110

Arg Ser Gly Lys Asp Pro Asp Arg Phe Arg Pro Asp Gly Leu Pro Lys
        115                 120                 125

Lys Tyr
    130
```

<210> SEQ ID NO 22
<211> LENGTH: 147
<212> TYPE: PRT
<213> ORGANISM: Homo sapiens

<400> SEQUENCE: 22

```
Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95
```

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 23
<211> LENGTH: 938
<212> TYPE: DNA
<213> ORGANISM: Homo sapiens

<400> SEQUENCE: 23

```
gttgactaag tcaataatca gaatcagcag gtttgcagtc agattggcag ggataagcag      60
cctagctcag gagaagtgag tataaaagcc ccaggctggg agcagccatc acagaagtcc     120
actcattctt ggcaggatgg cttctcatcg tctgctcctc ctctgccttg ctggactggt     180
atttgtgtct gaggctggcc ctacgggcac cggtgaatcc aagtgtcctc tgatggtcaa     240
agttctagat gctgtccgag gcagtcctgc catcaatgtg gccgtgcatg tgttcagaaa     300
ggctgctgat gacacctggg agccatttgc ctctgggaaa accagtgagt ctggagagct     360
gcatgggctc acaactgagg aggaatttgt agaagggata tacaaagtgg aaatagacac     420
caaatcttac tggaaggcac ttggcatctc cccattccat gagcatgcag aggtggtatt     480
cacagccaac gactccggcc ccgccgcta caccattgcc gccctgctga gcccctactc     540
ctattccacc acggctgtcg tcaccaatcc caaggaatga gggacttctc ctccagtgga     600
cctgaaggac gagggatggg atttcatgta accaagagta ttccattttt actaaagcag     660
tgttttcacc tcatatgcta tgttagaagt ccaggcagag acaataaaac attcctgtga     720
aaggcacttt tcattccact ttaacttgat tttttaaatt cccttattgt cccttccaaa     780
aaaaagagaa tcaaaatttt acaaagaatc aaaggaattc tagaaagtat ctgggcagaa     840
cgctaggaga gatccaaatt tccattgtct tgcaagcaaa gcacgtatta aatatgatct     900
gcagccatta aaaagacaca ttctgtaaaa aaaaaaaa                             938
```

<210> SEQ ID NO 24
<211> LENGTH: 147
<212> TYPE: PRT
<213> ORGANISM: Mus musculus

<400> SEQUENCE: 24

Met Ala Ser Leu Arg Leu Phe Leu Leu Cys Leu Ala Gly Leu Val Phe
1               5                   10                  15

Val Ser Glu Ala Gly Pro Ala Gly Ala Gly Glu Ser Lys Cys Pro Leu
            20                  25                  30

Met Val Lys Val Leu Asp Ala Val Arg Gly Ser Pro Ala Val Asp Val
        35                  40                  45

Ala Val Lys Val Phe Lys Lys Thr Ser Glu Gly Ser Trp Glu Pro Phe
    50                  55                  60

Ala Ser Gly Lys Thr Ala Glu Ser Gly Glu Leu His Gly Leu Thr Thr
65                  70                  75                  80

Asp Glu Lys Phe Val Glu Gly Val Tyr Arg Val Glu Leu Asp Thr Lys
                85                  90                  95

```
Ser Tyr Trp Lys Thr Leu Gly Ile Ser Pro Phe His Glu Phe Ala Asp
            100                 105                 110

Val Val Phe Thr Ala Asn Asp Ser Gly His Arg His Tyr Thr Ile Ala
        115                 120                 125

Ala Leu Leu Ser Pro Tyr Ser Tyr Ser Thr Thr Ala Val Val Ser Asn
        130                 135                 140

Pro Gln Asn
145

<210> SEQ ID NO 25
<211> LENGTH: 1237
<212> TYPE: DNA
<213> ORGANISM: Mus musculus

<400> SEQUENCE: 25
ctaatctccc taggcaaggt tcatatttgt gtaggttact tattctcctt ttgttgacta      60
agtcaataat cagaatcagc aggtttggag tcagcttggc agggatcagc agcctgggtt     120
ggaaggaggg ggtataaaag ccccttcacc aggagaagcc gtcacacaga tccacaagct     180
cctgacagga tggcttccct tcgactcttc ctcctttgcc tcgctggact ggtatttgtg     240
tctgaagctg gccccgcggg tgctggagaa tccaaatgtc ctctgatggt caaagtcctg     300
gatgctgtcc gaggcagccc tgctgtagac gtggctgtaa aagtgttcaa aaagacctct     360
gagggatcct gggagccctt tgcctctggg aagaccgcgg agtctggaga gctgcacggg     420
ctcaccacag atgagaagtt tgtagaagga gtgtacagag tagaactgga caccaaatcg     480
tactggaaga cacttggcat tccccgttc catgaattcg cggatgtggt tttcacagcc      540
aacgactctg ccatcgcca ctacaccatc gcagccctgc tcagcccata ctcctacagc      600
accacggctg tcgtcagcaa ccccagaat tgagagactc agcccaggag gaccaggatc      660
ttgccaaagc agtagcatcc catttgtacc aaaacagtgt tcttgctcta taaccgtgt      720 tagcagctca ggaagatgcc gtgaagcatt cttattaaac cacctgctat ttcattcaaa     780
ctgtgtttct ttttattc ctcattttc tcccctgctc ctaaaaccca aaatcttcta        840
aagaattcta gaaggtatgc gatcaaactt tttaaagaaa gaaaatactt tttgactcat     900
ggtttaaagg catcctttcc atcttgggga ggtcatgggt gctcctggca acttgcttga     960
ggaagatagg tcagaaagca gagtggacca accgttcaat gttttacaag caaaacatac    1020
actaagcatg gtctgtagct attaaaagca cacaatctga agggctgtag atgcacagta    1080
gtgttttccc agagcatgtt caaaagccct gggttcaatc acaatactga aagtaggcc     1140 aaaaaacatt ctgaaaatga aatatttggg ttttttttta taacctttag tgactaaata    1200
aagacaaatc taagagacta aaaaaaaaaa aaaaaaa                             1237

<210> SEQ ID NO 26
<211> LENGTH: 4563
<212> TYPE: PRT
<213> ORGANISM: Homo sapiens

<400> SEQUENCE: 26

Met Asp Pro Pro Arg Pro Ala Leu Leu Ala Leu Leu Ala Leu Pro Ala
1               5                   10                  15

Leu Leu Leu Leu Leu Leu Ala Gly Ala Arg Ala Glu Glu Glu Met Leu
                20                  25                  30

Glu Asn Val Ser Leu Val Cys Pro Lys Asp Ala Thr Arg Phe Lys His
            35                  40                  45
```

```
Leu Arg Lys Tyr Thr Tyr Asn Tyr Glu Ala Glu Ser Ser Gly Val
 50                  55                  60

Pro Gly Thr Ala Asp Ser Arg Ser Ala Thr Arg Ile Asn Cys Lys Val
 65                  70                  75                  80

Glu Leu Glu Val Pro Gln Leu Cys Ser Phe Ile Leu Lys Thr Ser Gln
                 85                  90                  95

Cys Thr Leu Lys Glu Val Tyr Gly Phe Asn Pro Glu Gly Lys Ala Leu
            100                 105                 110

Leu Lys Lys Thr Lys Asn Ser Glu Glu Phe Ala Ala Met Ser Arg
        115                 120                 125

Tyr Glu Leu Lys Leu Ala Ile Pro Gly Lys Gln Val Phe Leu Tyr
    130                 135                 140

Pro Glu Lys Asp Glu Pro Thr Tyr Ile Leu Asn Ile Lys Arg Gly Ile
145                 150                 155                 160

Ile Ser Ala Leu Leu Val Pro Pro Glu Thr Glu Ala Lys Gln Val
                165                 170                 175

Leu Phe Leu Asp Thr Val Tyr Gly Asn Cys Ser Thr His Phe Thr Val
                180                 185                 190

Lys Thr Arg Lys Gly Asn Val Ala Thr Glu Ile Ser Thr Glu Arg Asp
        195                 200                 205

Leu Gly Gln Cys Asp Arg Phe Lys Pro Ile Arg Thr Gly Ile Ser Pro
    210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
                245                 250                 255

Ala Glu Ala Ile Cys Lys Glu Gln His Leu Phe Leu Pro Phe Ser Tyr
                260                 265                 270

Lys Asn Lys Tyr Gly Met Val Ala Gln Val Thr Gln Thr Leu Lys Leu
        275                 280                 285

Glu Asp Thr Pro Lys Ile Asn Ser Arg Phe Phe Gly Glu Gly Thr Lys
    290                 295                 300

Lys Met Gly Leu Ala Phe Glu Ser Thr Lys Ser Thr Ser Pro Pro Lys
305                 310                 315                 320

Gln Ala Glu Ala Val Leu Lys Thr Leu Gln Glu Leu Lys Lys Leu Thr
                325                 330                 335

Ile Ser Glu Gln Asn Ile Gln Arg Ala Asn Leu Phe Asn Lys Leu Val
                340                 345                 350

Thr Glu Leu Arg Gly Leu Ser Asp Glu Ala Val Thr Ser Leu Leu Pro
        355                 360                 365

Gln Leu Ile Glu Val Ser Ser Pro Ile Thr Leu Gln Ala Leu Val Gln
    370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
                420                 425                 430

Ala Arg Asp Gln Arg Ser Arg Ala Thr Leu Tyr Ala Leu Ser His Ala
        435                 440                 445

Val Asn Asn Tyr His Lys Thr Asn Pro Thr Gly Thr Gln Glu Leu Leu
450                 455                 460
```

```
Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
            485                 490                 495

Gln Thr Met Glu Gln Leu Thr Pro Glu Leu Lys Ser Ser Ile Leu Lys
        500                 505                 510

Cys Val Gln Ser Thr Lys Pro Ser Leu Met Ile Gln Lys Ala Ala Ile
        515                 520                 525

Gln Ala Leu Arg Lys Met Glu Pro Lys Asp Lys Asp Gln Glu Val Leu
    530                 535                 540

Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                565                 570                 575

Ile Val Gln Ile Leu Pro Trp Glu Gln Asn Glu Gln Val Lys Asn Phe
            580                 585                 590

Val Ala Ser His Ile Ala Asn Ile Leu Asn Ser Glu Glu Leu Asp Ile
        595                 600                 605

Gln Asp Leu Lys Lys Leu Val Lys Glu Ala Leu Lys Glu Ser Gln Leu
    610                 615                 620

Pro Thr Val Met Asp Phe Arg Lys Phe Ser Arg Asn Tyr Gln Leu Tyr
625                 630                 635                 640

Lys Ser Val Ser Leu Pro Ser Leu Asp Pro Ala Ser Ala Lys Ile Glu
                645                 650                 655

Gly Asn Leu Ile Phe Asp Pro Asn Asn Tyr Leu Pro Lys Glu Ser Met
            660                 665                 670

Leu Lys Thr Thr Leu Thr Ala Phe Gly Phe Ala Ser Ala Asp Leu Ile
        675                 680                 685

Glu Ile Gly Leu Glu Gly Lys Gly Phe Glu Pro Thr Leu Glu Ala Leu
    690                 695                 700

Phe Gly Lys Gln Gly Phe Phe Pro Asp Ser Val Asn Lys Ala Leu Tyr
705                 710                 715                 720

Trp Val Asn Gly Gln Val Pro Asp Gly Val Ser Lys Val Leu Val Asp
                725                 730                 735

His Phe Gly Tyr Thr Lys Asp Asp Lys His Glu Gln Asp Met Val Asn
            740                 745                 750

Gly Ile Met Leu Ser Val Glu Lys Leu Ile Lys Asp Leu Lys Ser Lys
        755                 760                 765

Glu Val Pro Glu Ala Arg Ala Tyr Leu Arg Ile Leu Gly Glu Glu Leu
    770                 775                 780

Gly Phe Ala Ser Leu His Asp Leu Gln Leu Leu Gly Lys Leu Leu Leu
785                 790                 795                 800

Met Gly Ala Arg Thr Leu Gln Gly Ile Pro Gln Met Ile Gly Glu Val
                805                 810                 815

Ile Arg Lys Gly Ser Lys Asn Asp Phe Phe Leu His Tyr Ile Phe Met
            820                 825                 830

Glu Asn Ala Phe Glu Leu Pro Thr Gly Ala Gly Leu Gln Leu Gln Ile
        835                 840                 845

Ser Ser Ser Gly Val Ile Ala Pro Gly Ala Lys Ala Gly Val Lys Leu
    850                 855                 860

Glu Val Ala Asn Met Gln Ala Glu Leu Val Ala Lys Pro Ser Val Ser
865                 870                 875                 880
```

```
Val Glu Phe Val Thr Asn Met Gly Ile Ile Pro Asp Phe Ala Arg
                885                 890                 895

Ser Gly Val Gln Met Asn Thr Asn Phe Phe His Glu Ser Gly Leu Glu
            900                 905                 910

Ala His Val Ala Leu Lys Ala Gly Lys Leu Lys Phe Ile Ile Pro Ser
            915                 920                 925

Pro Lys Arg Pro Val Lys Leu Leu Ser Gly Gly Asn Thr Leu His Leu
        930                 935                 940

Val Ser Thr Thr Lys Thr Glu Val Ile Pro Leu Ile Glu Asn Arg
945                 950                 955                 960

Gln Ser Trp Ser Val Cys Lys Gln Val Phe Pro Gly Leu Asn Tyr Cys
                965                 970                 975

Thr Ser Gly Ala Tyr Ser Asn Ala Ser Ser Thr Asp Ser Ala Ser Tyr
            980                 985                 990

Tyr Pro Leu Thr Gly Asp Thr Arg Leu Glu Leu Glu Leu Arg Pro Thr
            995                 1000                1005

Gly Glu Ile Glu Gln Tyr Ser Val Ser Ala Thr Tyr Glu Leu Gln
    1010                1015                1020

Arg Glu Asp Arg Ala Leu Val Asp Thr Leu Lys Phe Val Thr Gln
    1025                1030                1035

Ala Glu Gly Ala Lys Gln Thr Glu Ala Thr Met Thr Phe Lys Tyr
    1040                1045                1050

Asn Arg Gln Ser Met Thr Leu Ser Ser Glu Val Gln Ile Pro Asp
    1055                1060                1065

Phe Asp Val Asp Leu Gly Thr Ile Leu Arg Val Asn Asp Glu Ser
    1070                1075                1080

Thr Glu Gly Lys Thr Ser Tyr Arg Leu Thr Leu Asp Ile Gln Asn
    1085                1090                1095

Lys Lys Ile Thr Glu Val Ala Leu Met Gly His Leu Ser Cys Asp
    1100                1105                1110

Thr Lys Glu Glu Arg Lys Ile Lys Gly Val Ile Ser Ile Pro Arg
    1115                1120                1125

Leu Gln Ala Glu Ala Arg Ser Glu Ile Leu Ala His Trp Ser Pro
    1130                1135                1140

Ala Lys Leu Leu Leu Gln Met Asp Ser Ser Ala Thr Ala Tyr Gly
    1145                1150                1155

Ser Thr Val Ser Lys Arg Val Ala Trp His Tyr Asp Glu Glu Lys
    1160                1165                1170

Ile Glu Phe Glu Trp Asn Thr Gly Thr Asn Val Asp Thr Lys Lys
    1175                1180                1185

Met Thr Ser Asn Phe Pro Val Asp Leu Ser Asp Tyr Pro Lys Ser
    1190                1195                1200

Leu His Met Tyr Ala Asn Arg Leu Leu Asp His Arg Val Pro Gln
    1205                1210                1215

Thr Asp Met Thr Phe Arg His Val Gly Ser Lys Leu Ile Val Ala
    1220                1225                1230

Met Ser Ser Trp Leu Gln Lys Ala Ser Gly Ser Leu Pro Tyr Thr
    1235                1240                1245

Gln Thr Leu Gln Asp His Leu Asn Ser Leu Lys Glu Phe Asn Leu
    1250                1255                1260

Gln Asn Met Gly Leu Pro Asp Phe His Ile Pro Glu Asn Leu Phe
    1265                1270                1275
```

```
Leu Lys Ser Asp Gly Arg Val Lys Tyr Thr Leu Asn Lys Asn Ser
    1280                1285                1290

Leu Lys Ile Glu Ile Pro Leu Pro Phe Gly Gly Lys Ser Ser Arg
    1295                1300                1305

Asp Leu Lys Met Leu Glu Thr Val Arg Thr Pro Ala Leu His Phe
    1310                1315                1320

Lys Ser Val Gly Phe His Leu Pro Ser Arg Glu Phe Gln Val Pro
    1325                1330                1335

Thr Phe Thr Ile Pro Lys Leu Tyr Gln Leu Gln Val Pro Leu Leu
    1340                1345                1350

Gly Val Leu Asp Leu Ser Thr Asn Val Tyr Ser Asn Leu Tyr Asn
    1355                1360                1365

Trp Ser Ala Ser Tyr Ser Gly Gly Asn Thr Ser Thr Asp His Phe
    1370                1375                1380

Ser Leu Arg Ala Arg Tyr His Met Lys Ala Asp Ser Val Val Asp
    1385                1390                1395

Leu Leu Ser Tyr Asn Val Gln Gly Ser Gly Glu Thr Thr Tyr Asp
    1400                1405                1410

His Lys Asn Thr Phe Thr Leu Ser Cys Asp Gly Ser Leu Arg His
    1415                1420                1425

Lys Phe Leu Asp Ser Asn Ile Lys Phe Ser His Val Glu Lys Leu
    1430                1435                1440

Gly Asn Asn Pro Val Ser Lys Gly Leu Leu Ile Phe Asp Ala Ser
    1445                1450                1455

Ser Ser Trp Gly Pro Gln Met Ser Ala Ser Val His Leu Asp Ser
    1460                1465                1470

Lys Lys Lys Gln His Leu Phe Val Lys Glu Val Lys Ile Asp Gly
    1475                1480                1485

Gln Phe Arg Val Ser Ser Phe Tyr Ala Lys Gly Thr Tyr Gly Leu
    1490                1495                1500

Ser Cys Gln Arg Asp Pro Asn Thr Gly Arg Leu Asn Gly Glu Ser
    1505                1510                1515

Asn Leu Arg Phe Asn Ser Ser Tyr Leu Gln Gly Thr Asn Gln Ile
    1520                1525                1530

Thr Gly Arg Tyr Glu Asp Gly Thr Leu Ser Leu Thr Ser Thr Ser
    1535                1540                1545

Asp Leu Gln Ser Gly Ile Ile Lys Asn Thr Ala Ser Leu Lys Tyr
    1550                1555                1560

Glu Asn Tyr Glu Leu Thr Leu Lys Ser Asp Thr Asn Gly Lys Tyr
    1565                1570                1575

Lys Asn Phe Ala Thr Ser Asn Lys Met Asp Met Thr Phe Ser Lys
    1580                1585                1590

Gln Asn Ala Leu Leu Arg Ser Glu Tyr Gln Ala Asp Tyr Glu Ser
    1595                1600                1605

Leu Arg Phe Phe Ser Leu Leu Ser Gly Ser Leu Asn Ser His Gly
    1610                1615                1620

Leu Glu Leu Asn Ala Asp Ile Leu Gly Thr Asp Lys Ile Asn Ser
    1625                1630                1635

Gly Ala His Lys Ala Thr Leu Arg Ile Gly Gln Asp Gly Ile Ser
    1640                1645                1650

Thr Ser Ala Thr Thr Asn Leu Lys Cys Ser Leu Leu Val Leu Glu
    1655                1660                1665
```

```
Asn Glu Leu Asn Ala Glu Leu Gly Leu Ser Gly Ala Ser Met Lys
1670                1675                1680

Leu Thr Thr Asn Gly Arg Phe Arg Glu His Asn Ala Lys Phe Ser
1685                1690                1695

Leu Asp Gly Lys Ala Ala Leu Thr Glu Leu Ser Leu Gly Ser Ala
1700                1705                1710

Tyr Gln Ala Met Ile Leu Gly Val Asp Ser Lys Asn Ile Phe Asn
1715                1720                1725

Phe Lys Val Ser Gln Glu Gly Leu Lys Leu Ser Asn Asp Met Met
1730                1735                1740

Gly Ser Tyr Ala Glu Met Lys Phe Asp His Thr Asn Ser Leu Asn
1745                1750                1755

Ile Ala Gly Leu Ser Leu Asp Phe Ser Ser Lys Leu Asp Asn Ile
1760                1765                1770

Tyr Ser Ser Asp Lys Phe Tyr Lys Gln Thr Val Asn Leu Gln Leu
1775                1780                1785

Gln Pro Tyr Ser Leu Val Thr Thr Leu Asn Ser Asp Leu Lys Tyr
1790                1795                1800

Asn Ala Leu Asp Leu Thr Asn Asn Gly Lys Leu Arg Leu Glu Pro
1805                1810                1815

Leu Lys Leu His Val Ala Gly Asn Leu Lys Gly Ala Tyr Gln Asn
1820                1825                1830

Asn Glu Ile Lys His Ile Tyr Ala Ile Ser Ser Ala Ala Leu Ser
1835                1840                1845

Ala Ser Tyr Lys Ala Asp Thr Val Ala Lys Val Gln Gly Val Glu
1850                1855                1860

Phe Ser His Arg Leu Asn Thr Asp Ile Ala Gly Leu Ala Ser Ala
1865                1870                1875

Ile Asp Met Ser Thr Asn Tyr Asn Ser Asp Ser Leu His Phe Ser
1880                1885                1890

Asn Val Phe Arg Ser Val Met Ala Pro Phe Thr Met Thr Ile Asp
1895                1900                1905

Ala His Thr Asn Gly Asn Gly Lys Leu Ala Leu Trp Gly Glu His
1910                1915                1920

Thr Gly Gln Leu Tyr Ser Lys Phe Leu Leu Lys Ala Glu Pro Leu
1925                1930                1935

Ala Phe Thr Phe Ser His Asp Tyr Lys Gly Ser Thr Ser His His
1940                1945                1950

Leu Val Ser Arg Lys Ser Ile Ser Ala Ala Leu Glu His Lys Val
1955                1960                1965

Ser Ala Leu Leu Thr Pro Ala Glu Gln Thr Gly Thr Trp Lys Leu
1970                1975                1980

Lys Thr Gln Phe Asn Asn Asn Glu Tyr Ser Gln Asp Leu Asp Ala
1985                1990                1995

Tyr Asn Thr Lys Asp Lys Ile Gly Val Glu Leu Thr Gly Arg Thr
2000                2005                2010

Leu Ala Asp Leu Thr Leu Leu Asp Ser Pro Ile Lys Val Pro Leu
2015                2020                2025

Leu Leu Ser Glu Pro Ile Asn Ile Ile Asp Ala Leu Glu Met Arg
2030                2035                2040

Asp Ala Val Glu Lys Pro Gln Glu Phe Thr Ile Val Ala Phe Val
2045                2050                2055
```

```
Lys Tyr Asp Lys Asn Gln Asp Val His Ser Ile Asn Leu Pro Phe
2060             2065             2070

Phe Glu Thr Leu Gln Glu Tyr Phe Glu Arg Asn Arg Gln Thr Ile
2075             2080             2085

Ile Val Val Leu Glu Asn Val Gln Arg Asn Leu Lys His Ile Asn
2090             2095             2100

Ile Asp Gln Phe Val Arg Lys Tyr Arg Ala Ala Leu Gly Lys Leu
2105             2110             2115

Pro Gln Gln Ala Asn Asp Tyr Leu Asn Ser Phe Asn Trp Glu Arg
2120             2125             2130

Gln Val Ser His Ala Lys Glu Lys Leu Thr Ala Leu Thr Lys Lys
2135             2140             2145

Tyr Arg Ile Thr Glu Asn Asp Ile Gln Ile Ala Leu Asp Asp Ala
2150             2155             2160

Lys Ile Asn Phe Asn Glu Lys Leu Ser Gln Leu Gln Thr Tyr Met
2165             2170             2175

Ile Gln Phe Asp Gln Tyr Ile Lys Asp Ser Tyr Asp Leu His Asp
2180             2185             2190

Leu Lys Ile Ala Ile Ala Asn Ile Ile Asp Glu Ile Ile Glu Lys
2195             2200             2205

Leu Lys Ser Leu Asp Glu His Tyr His Ile Arg Val Asn Leu Val
2210             2215             2220

Lys Thr Ile His Asp Leu His Leu Phe Ile Glu Asn Ile Asp Phe
2225             2230             2235

Asn Lys Ser Gly Ser Ser Thr Ala Ser Trp Ile Gln Asn Val Asp
2240             2245             2250

Thr Lys Tyr Gln Ile Arg Ile Gln Ile Gln Glu Lys Leu Gln Gln
2255             2260             2265

Leu Lys Arg His Ile Gln Asn Ile Asp Ile Gln His Leu Ala Gly
2270             2275             2280

Lys Leu Lys Gln His Ile Glu Ala Ile Asp Val Arg Val Leu Leu
2285             2290             2295

Asp Gln Leu Gly Thr Thr Ile Ser Phe Glu Arg Ile Asn Asp Val
2300             2305             2310

Leu Glu His Val Lys His Phe Val Ile Asn Leu Ile Gly Asp Phe
2315             2320             2325

Glu Val Ala Glu Lys Ile Asn Ala Phe Arg Ala Lys Val His Glu
2330             2335             2340

Leu Ile Glu Arg Tyr Glu Val Asp Gln Gln Ile Gln Val Leu Met
2345             2350             2355

Asp Lys Leu Val Glu Leu Ala His Gln Tyr Lys Leu Lys Glu Thr
2360             2365             2370

Ile Gln Lys Leu Ser Asn Val Leu Gln Gln Val Lys Ile Lys Asp
2375             2380             2385

Tyr Phe Glu Lys Leu Val Gly Phe Ile Asp Asp Ala Val Lys Lys
2390             2395             2400

Leu Asn Glu Leu Ser Phe Lys Thr Phe Ile Glu Asp Val Asn Lys
2405             2410             2415

Phe Leu Asp Met Leu Ile Lys Lys Leu Lys Ser Phe Asp Tyr His
2420             2425             2430

Gln Phe Val Asp Glu Thr Asn Asp Lys Ile Arg Glu Val Thr Gln
2435             2440             2445
```

Arg Leu Asn Gly Glu Ile Gln Ala Leu Glu Leu Pro Gln Lys Ala
2450                2455                2460

Glu Ala Leu Lys Leu Phe Leu Glu Glu Thr Lys Ala Thr Val Ala
2465                2470                2475

Val Tyr Leu Glu Ser Leu Gln Asp Thr Lys Ile Thr Leu Ile Ile
2480                2485                2490

Asn Trp Leu Gln Glu Ala Leu Ser Ser Ala Ser Leu Ala His Met
2495                2500                2505

Lys Ala Lys Phe Arg Glu Thr Leu Glu Asp Thr Arg Asp Arg Met
2510                2515                2520

Tyr Gln Met Asp Ile Gln Gln Glu Leu Gln Arg Tyr Leu Ser Leu
2525                2530                2535

Val Gly Gln Val Tyr Ser Thr Leu Val Thr Tyr Ile Ser Asp Trp
2540                2545                2550

Trp Thr Leu Ala Ala Lys Asn Leu Thr Asp Phe Ala Glu Gln Tyr
2555                2560                2565

Ser Ile Gln Asp Trp Ala Lys Arg Met Lys Ala Leu Val Glu Gln
2570                2575                2580

Gly Phe Thr Val Pro Glu Ile Lys Thr Ile Leu Gly Thr Met Pro
2585                2590                2595

Ala Phe Glu Val Ser Leu Gln Ala Leu Gln Lys Ala Thr Phe Gln
2600                2605                2610

Thr Pro Asp Phe Ile Val Pro Leu Thr Asp Leu Arg Ile Pro Ser
2615                2620                2625

Val Gln Ile Asn Phe Lys Asp Leu Lys Asn Ile Lys Ile Pro Ser
2630                2635                2640

Arg Phe Ser Thr Pro Glu Phe Thr Ile Leu Asn Thr Phe His Ile
2645                2650                2655

Pro Ser Phe Thr Ile Asp Phe Val Glu Met Lys Val Lys Ile Ile
2660                2665                2670

Arg Thr Ile Asp Gln Met Leu Asn Ser Glu Leu Gln Trp Pro Val
2675                2680                2685

Pro Asp Ile Tyr Leu Arg Asp Leu Lys Val Glu Asp Ile Pro Leu
2690                2695                2700

Ala Arg Ile Thr Leu Pro Asp Phe Arg Leu Pro Glu Ile Ala Ile
2705                2710                2715

Pro Glu Phe Ile Ile Pro Thr Leu Asn Leu Asn Asp Phe Gln Val
2720                2725                2730

Pro Asp Leu His Ile Pro Glu Phe Gln Leu Pro His Ile Ser His
2735                2740                2745

Thr Ile Glu Val Pro Thr Phe Gly Lys Leu Tyr Ser Ile Leu Lys
2750                2755                2760

Ile Gln Ser Pro Leu Phe Thr Leu Asp Ala Asn Ala Asp Ile Gly
2765                2770                2775

Asn Gly Thr Thr Ser Ala Asn Glu Ala Gly Ile Ala Ala Ser Ile
2780                2785                2790

Thr Ala Lys Gly Glu Ser Lys Leu Glu Val Leu Asn Phe Asp Phe
2795                2800                2805

Gln Ala Asn Ala Gln Leu Ser Asn Pro Lys Ile Asn Pro Leu Ala
2810                2815                2820

Leu Lys Glu Ser Val Lys Phe Ser Ser Lys Tyr Leu Arg Thr Glu
2825                2830                2835

-continued

```
His Gly Ser Glu Met Leu Phe Phe Gly Asn Ala Ile Glu Gly Lys
2840            2845                2850

Ser Asn Thr Val Ala Ser Leu His Thr Glu Lys Asn Thr Leu Glu
2855            2860                2865

Leu Ser Asn Gly Val Ile Val Lys Ile Asn Asn Gln Leu Thr Leu
2870            2875                2880

Asp Ser Asn Thr Lys Tyr Phe His Lys Leu Asn Ile Pro Lys Leu
2885            2890                2895

Asp Phe Ser Ser Gln Ala Asp Leu Arg Asn Glu Ile Lys Thr Leu
2900            2905                2910

Leu Lys Ala Gly His Ile Ala Trp Thr Ser Ser Gly Lys Gly Ser
2915            2920                2925

Trp Lys Trp Ala Cys Pro Arg Phe Ser Asp Glu Gly Thr His Glu
2930            2935                2940

Ser Gln Ile Ser Phe Thr Ile Glu Gly Pro Leu Thr Ser Phe Gly
2945            2950                2955

Leu Ser Asn Lys Ile Asn Ser Lys His Leu Arg Val Asn Gln Asn
2960            2965                2970

Leu Val Tyr Glu Ser Gly Ser Leu Asn Phe Ser Lys Leu Glu Ile
2975            2980                2985

Gln Ser Gln Val Asp Ser Gln His Val Gly His Ser Val Leu Thr
2990            2995                3000

Ala Lys Gly Met Ala Leu Phe Gly Glu Gly Lys Ala Glu Phe Thr
3005            3010                3015

Gly Arg His Asp Ala His Leu Asn Gly Lys Val Ile Gly Thr Leu
3020            3025                3030

Lys Asn Ser Leu Phe Phe Ser Ala Gln Pro Phe Glu Ile Thr Ala
3035            3040                3045

Ser Thr Asn Asn Glu Gly Asn Leu Lys Val Arg Phe Pro Leu Arg
3050            3055                3060

Leu Thr Gly Lys Ile Asp Phe Leu Asn Asn Tyr Ala Leu Phe Leu
3065            3070                3075

Ser Pro Ser Ala Gln Gln Ala Ser Trp Gln Val Ser Ala Arg Phe
3080            3085                3090

Asn Gln Tyr Lys Tyr Asn Gln Asn Phe Ser Ala Gly Asn Asn Glu
3095            3100                3105

Asn Ile Met Glu Ala His Val Gly Ile Asn Gly Glu Ala Asn Leu
3110            3115                3120

Asp Phe Leu Asn Ile Pro Leu Thr Ile Pro Glu Met Arg Leu Pro
3125            3130                3135

Tyr Thr Ile Ile Thr Thr Pro Pro Leu Lys Asp Phe Ser Leu Trp
3140            3145                3150

Glu Lys Thr Gly Leu Lys Glu Phe Leu Lys Thr Thr Lys Gln Ser
3155            3160                3165

Phe Asp Leu Ser Val Lys Ala Gln Tyr Lys Lys Asn Lys His Arg
3170            3175                3180

His Ser Ile Thr Asn Pro Leu Ala Val Leu Cys Glu Phe Ile Ser
3185            3190                3195

Gln Ser Ile Lys Ser Phe Asp Arg His Phe Glu Lys Asn Arg Asn
3200            3205                3210

Asn Ala Leu Asp Phe Val Thr Lys Ser Tyr Asn Glu Thr Lys Ile
3215            3220                3225
```

-continued

```
Lys Phe Asp Lys Tyr Lys Ala Glu Lys Ser His Asp Glu Leu Pro
    3230                3235                3240

Arg Thr Phe Gln Ile Pro Gly Tyr Thr Val Pro Val Val Asn Val
3245                3250                3255

Glu Val Ser Pro Phe Thr Ile Glu Met Ser Ala Phe Gly Tyr Val
3260                3265                3270

Phe Pro Lys Ala Val Ser Met Pro Ser Phe Ser Ile Leu Gly Ser
3275                3280                3285

Asp Val Arg Val Pro Ser Tyr Thr Leu Ile Leu Pro Ser Leu Glu
3290                3295                3300

Leu Pro Val Leu His Val Pro Arg Asn Leu Lys Leu Ser Leu Pro
3305                3310                3315

Asp Phe Lys Glu Leu Cys Thr Ile Ser His Ile Phe Ile Pro Ala
3320                3325                3330

Met Gly Asn Ile Thr Tyr Asp Phe Ser Phe Lys Ser Ser Val Ile
3335                3340                3345

Thr Leu Asn Thr Asn Ala Glu Leu Phe Asn Gln Ser Asp Ile Val
3350                3355                3360

Ala His Leu Leu Ser Ser Ser Ser Val Ile Asp Ala Leu Gln
3365                3370                3375

Tyr Lys Leu Glu Gly Thr Thr Arg Leu Thr Arg Lys Arg Gly Leu
3380                3385                3390

Lys Leu Ala Thr Ala Leu Ser Leu Ser Asn Lys Phe Val Glu Gly
3395                3400                3405

Ser His Asn Ser Thr Val Ser Leu Thr Thr Lys Asn Met Glu Val
3410                3415                3420

Ser Val Ala Thr Thr Thr Lys Ala Gln Ile Pro Ile Leu Arg Met
3425                3430                3435

Asn Phe Lys Gln Glu Leu Asn Gly Asn Thr Lys Ser Lys Pro Thr
3440                3445                3450

Val Ser Ser Ser Met Glu Phe Lys Tyr Asp Phe Asn Ser Ser Met
3455                3460                3465

Leu Tyr Ser Thr Ala Lys Gly Ala Val Asp His Lys Leu Ser Leu
3470                3475                3480

Glu Ser Leu Thr Ser Tyr Phe Ser Ile Glu Ser Ser Thr Lys Gly
3485                3490                3495

Asp Val Lys Gly Ser Val Leu Ser Arg Glu Tyr Ser Gly Thr Ile
3500                3505                3510

Ala Ser Glu Ala Asn Thr Tyr Leu Asn Ser Lys Ser Thr Arg Ser
3515                3520                3525

Ser Val Lys Leu Gln Gly Thr Ser Lys Ile Asp Asp Ile Trp Asn
3530                3535                3540

Leu Glu Val Lys Glu Asn Phe Ala Gly Glu Ala Thr Leu Gln Arg
3545                3550                3555

Ile Tyr Ser Leu Trp Glu His Ser Thr Lys Asn His Leu Gln Leu
3560                3565                3570

Glu Gly Leu Phe Phe Thr Asn Gly Glu His Thr Ser Lys Ala Thr
3575                3580                3585

Leu Glu Leu Ser Pro Trp Gln Met Ser Ala Leu Val Gln Val His
3590                3595                3600

Ala Ser Gln Pro Ser Ser Phe His Asp Phe Pro Asp Leu Gly Gln
3605                3610                3615
```

Glu Val Ala Leu Asn Ala Asn Thr Lys Asn Gln Lys Ile Arg Trp
3620                3625                3630

Lys Asn Glu Val Arg Ile His Ser Gly Ser Phe Gln Ser Gln Val
3635                3640                3645

Glu Leu Ser Asn Asp Gln Glu Lys Ala His Leu Asp Ile Ala Gly
3650                3655                3660

Ser Leu Glu Gly His Leu Arg Phe Leu Lys Asn Ile Ile Leu Pro
3665                3670                3675

Val Tyr Asp Lys Ser Leu Trp Asp Phe Leu Lys Leu Asp Val Thr
3680                3685                3690

Thr Ser Ile Gly Arg Arg Gln His Leu Arg Val Ser Thr Ala Phe
3695                3700                3705

Val Tyr Thr Lys Asn Pro Asn Gly Tyr Ser Phe Ser Ile Pro Val
3710                3715                3720

Lys Val Leu Ala Asp Lys Phe Ile Ile Pro Gly Leu Lys Leu Asn
3725                3730                3735

Asp Leu Asn Ser Val Leu Val Met Pro Thr Phe His Val Pro Phe
3740                3745                3750

Thr Asp Leu Gln Val Pro Ser Cys Lys Leu Asp Phe Arg Glu Ile
3755                3760                3765

Gln Ile Tyr Lys Lys Leu Arg Thr Ser Ser Phe Ala Leu Asn Leu
3770                3775                3780

Pro Thr Leu Pro Glu Val Lys Phe Pro Glu Val Asp Val Leu Thr
3785                3790                3795

Lys Tyr Ser Gln Pro Glu Asp Ser Leu Ile Pro Phe Phe Glu Ile
3800                3805                3810

Thr Val Pro Glu Ser Gln Leu Thr Val Ser Gln Phe Thr Leu Pro
3815                3820                3825

Lys Ser Val Ser Asp Gly Ile Ala Ala Leu Asp Leu Asn Ala Val
3830                3835                3840

Ala Asn Lys Ile Ala Asp Phe Glu Leu Pro Thr Ile Ile Val Pro
3845                3850                3855

Glu Gln Thr Ile Glu Ile Pro Ser Ile Lys Phe Ser Val Pro Ala
3860                3865                3870

Gly Ile Val Ile Pro Ser Phe Gln Ala Leu Thr Ala Arg Phe Glu
3875                3880                3885

Val Asp Ser Pro Val Tyr Asn Ala Thr Trp Ser Ala Ser Leu Lys
3890                3895                3900

Asn Lys Ala Asp Tyr Val Glu Thr Val Leu Asp Ser Thr Cys Ser
3905                3910                3915

Ser Thr Val Gln Phe Leu Glu Tyr Glu Leu Asn Val Leu Gly Thr
3920                3925                3930

His Lys Ile Glu Asp Gly Thr Leu Ala Ser Lys Thr Lys Gly Thr
3935                3940                3945

Phe Ala His Arg Asp Phe Ser Ala Glu Tyr Glu Glu Asp Gly Lys
3950                3955                3960

Tyr Glu Gly Leu Gln Glu Trp Glu Gly Lys Ala His Leu Asn Ile
3965                3970                3975

Lys Ser Pro Ala Phe Thr Asp Leu His Leu Arg Tyr Gln Lys Asp
3980                3985                3990

Lys Lys Gly Ile Ser Thr Ser Ala Ala Ser Pro Ala Val Gly Thr
3995                4000                4005

```
Val Gly Met Asp Met Asp Glu Asp Asp Asp Phe Ser Lys Trp Asn
4010                4015                4020

Phe Tyr Tyr Ser Pro Gln Ser Ser Pro Asp Lys Lys Leu Thr Ile
4025                4030                4035

Phe Lys Thr Glu Leu Arg Val Arg Glu Ser Asp Glu Glu Thr Gln
4040                4045                4050

Ile Lys Val Asn Trp Glu Glu Ala Ala Ser Gly Leu Leu Thr
4055                4060                4065

Ser Leu Lys Asp Asn Val Pro Lys Ala Thr Gly Val Leu Tyr Asp
4070                4075                4080

Tyr Val Asn Lys Tyr His Trp Glu His Thr Gly Leu Thr Leu Arg
4085                4090                4095

Glu Val Ser Ser Lys Leu Arg Arg Asn Leu Gln Asn Asn Ala Glu
4100                4105                4110

Trp Val Tyr Gln Gly Ala Ile Arg Gln Ile Asp Asp Ile Asp Val
4115                4120                4125

Arg Phe Gln Lys Ala Ala Ser Gly Thr Thr Gly Thr Tyr Gln Glu
4130                4135                4140

Trp Lys Asp Lys Ala Gln Asn Leu Tyr Gln Glu Leu Leu Thr Gln
4145                4150                4155

Glu Gly Gln Ala Ser Phe Gln Gly Leu Lys Asp Asn Val Phe Asp
4160                4165                4170

Gly Leu Val Arg Val Thr Gln Glu Phe His Met Lys Val Lys His
4175                4180                4185

Leu Ile Asp Ser Leu Ile Asp Phe Leu Asn Phe Pro Arg Phe Gln
4190                4195                4200

Phe Pro Gly Lys Pro Gly Ile Tyr Thr Arg Glu Glu Leu Cys Thr
4205                4210                4215

Met Phe Ile Arg Glu Val Gly Thr Val Leu Ser Gln Val Tyr Ser
4220                4225                4230

Lys Val His Asn Gly Ser Glu Ile Leu Phe Ser Tyr Phe Gln Asp
4235                4240                4245

Leu Val Ile Thr Leu Pro Phe Glu Leu Arg Lys His Lys Leu Ile
4250                4255                4260

Asp Val Ile Ser Met Tyr Arg Glu Leu Leu Lys Asp Leu Ser Lys
4265                4270                4275

Glu Ala Gln Glu Val Phe Lys Ala Ile Gln Ser Leu Lys Thr Thr
4280                4285                4290

Glu Val Leu Arg Asn Leu Gln Asp Leu Leu Gln Phe Ile Phe Gln
4295                4300                4305

Leu Ile Glu Asp Asn Ile Lys Gln Leu Lys Glu Met Lys Phe Thr
4310                4315                4320

Tyr Leu Ile Asn Tyr Ile Gln Asp Glu Ile Asn Thr Ile Phe Ser
4325                4330                4335

Asp Tyr Ile Pro Tyr Val Phe Lys Leu Leu Lys Glu Asn Leu Cys
4340                4345                4350

Leu Asn Leu His Lys Phe Asn Glu Phe Ile Gln Asn Glu Leu Gln
4355                4360                4365

Glu Ala Ser Gln Glu Leu Gln Gln Ile His Gln Tyr Ile Met Ala
4370                4375                4380

Leu Arg Glu Glu Tyr Phe Asp Pro Ser Ile Val Gly Trp Thr Val
4385                4390                4395
```

| | | | | | | | | | | | | |
|---|---|---|---|---|---|---|---|---|---|---|---|---|
| Lys | Tyr | Tyr | Glu | Leu | Glu | Glu | Lys | Ile | Val | Ser | Leu | Ile | Lys | Asn |
| | | | | 4400 | | | 4405 | | | | 4410 | | | |
| Leu | Leu | Val | Ala | Leu | Lys | Asp | Phe | His | Ser | Glu | Tyr | Ile | Val | Ser |
| | 4415 | | | | | 4420 | | | | | 4425 | | | |
| Ala | Ser | Asn | Phe | Thr | Ser | Gln | Leu | Ser | Ser | Gln | Val | Glu | Gln | Phe |
| | 4430 | | | | | 4435 | | | | | 4440 | | | |
| Leu | His | Arg | Asn | Ile | Gln | Glu | Tyr | Leu | Ser | Ile | Leu | Thr | Asp | Pro |
| | 4445 | | | | | 4450 | | | | | 4455 | | | |
| Asp | Gly | Lys | Gly | Lys | Glu | Lys | Ile | Ala | Glu | Leu | Ser | Ala | Thr | Ala |
| | 4460 | | | | | 4465 | | | | | 4470 | | | |
| Gln | Glu | Ile | Ile | Lys | Ser | Gln | Ala | Ile | Ala | Thr | Lys | Lys | Ile | Ile |
| | 4475 | | | | | 4480 | | | | | 4485 | | | |
| Ser | Asp | Tyr | His | Gln | Gln | Phe | Arg | Tyr | Lys | Leu | Gln | Asp | Phe | Ser |
| | 4490 | | | | | 4495 | | | | | 4500 | | | |
| Asp | Gln | Leu | Ser | Asp | Tyr | Tyr | Glu | Lys | Phe | Ile | Ala | Glu | Ser | Lys |
| | 4505 | | | | | 4510 | | | | | 4515 | | | |
| Arg | Leu | Ile | Asp | Leu | Ser | Ile | Gln | Asn | Tyr | His | Thr | Phe | Leu | Ile |
| | 4520 | | | | | 4525 | | | | | 4530 | | | |
| Tyr | Ile | Thr | Glu | Leu | Leu | Lys | Lys | Leu | Gln | Ser | Thr | Thr | Val | Met |
| | 4535 | | | | | 4540 | | | | | 4545 | | | |
| Asn | Pro | Tyr | Met | Lys | Leu | Ala | Pro | Gly | Glu | Leu | Thr | Ile | Ile | Leu |
| | 4550 | | | | | 4555 | | | | | 4560 | | | |

<210> SEQ ID NO 27
<211> LENGTH: 14121
<212> TYPE: DNA
<213> ORGANISM: Homo sapiens

<400> SEQUENCE: 27

| | |
|---|---|
| attcccaccg ggacctgcgg ggctgagtgc ccttctcggt tgctgccgct gaggagcccg | 60 |
| cccagccagc cagggccgcg aggccgaggc caggccgcag cccaggagcc gccccaccgc | 120 |
| agctggcgat ggacccgccg aggcccgcgc tgctggcgct gctggcgctg cctgcgctgc | 180 |
| tgctgctgct gctggcgggc gccagggccg aagaggaaat gctggaaaat gtcagcctgg | 240 |
| tctgtccaaa agatgcgacc cgattcaagc acctccggaa gtacacatac aactatgagg | 300 |
| ctgagagttc cagtggagtc cctgggactg ctgattcaag aagtgccacc aggatcaact | 360 |
| gcaaggttga gctggaggtt ccccagctct gcagcttcat cctgaagacc agccagtgca | 420 |
| ccctgaaaga ggtgtatggc ttcaaccctg agggcaaagc cttgctgaag aaaaccaaga | 480 |
| actctgagga gtttgctgca gccatgtcca ggtatgagct caagctggcc attccagaag | 540 |
| ggaagcaggt tttccttttac ccggagaaag atgaacctac ttacatcctg aacatcaaga | 600 |
| ggggcatcat ttctgccctc ctggttcccc agagacaga agaagccaag caagtgttgt | 660 |
| ttctggatac cgtgtatgga aactgctcca ctcactttac cgtcaagacg aggaagggca | 720 |
| atgtggcaac agaaatatcc actgaaagag acctggggca gtgtgatcgc ttcaagccca | 780 |
| tccgcacagg catcagccca cttgctctca tcaaaggcat gacccgcccc tgtcaactc | 840 |
| tgatcagcag cagccagtcc tgtcagtaca cactggacgc taagaggaag catgtggcag | 900 |
| aagccatctg caaggagcaa cacctcttcc tgcctttctc ctacaagaat aagtatggga | 960 |
| tggtagcaca agtgacacag actttgaaac ttgaagacac accaaagatc aacagccgct | 1020 |
| tctttggtga aggtactaag aagatggggc tcgcatttga gagcaccaaa tccacatcac | 1080 |
| ctccaaagca ggccgaagct gttttgaaga ctctccagga actgaaaaaa ctaaccatct | 1140 |

```
ctgagcaaaa tatccagaga gctaatctct tcaataagct ggttactgag ctgagaggcc   1200
tcagtgatga agcagtcaca tctctcttgc cacagctgat tgaggtgtcc agccccatca   1260
ctttacaagc cttggttcag tgtggacagc ctcagtgctc cactcacatc ctccagtggc   1320
tgaaacgtgt gcatgccaac cccttctga tagatgtggt cacctacctg gtggccctga    1380
tccccgagcc ctcagcacag cagctgcgag agatcttcaa catggcgagg gatcagcgca   1440
gccgagccac cttgtatgcg ctgagccacg cggtcaacaa ctatcataag acaaacccta   1500
cagggaccca ggagctgctg acattgcta attacctgat ggaacagatt caagatgact    1560
gcactgggga tgaagattac acctatttga ttctgcgggt cattggaaat atgggccaaa   1620
ccatggagca gttaactcca gaactcaagt cttcaatcct gaaatgtgtc caaagtacaa   1680
agccatcact gatgatccag aaagctgcca tccaggctct gcggaaaatg gagcctaaag   1740
acaaggacca ggaggttctt cttcagactt tccttgatga tgcttctccg ggagataagc   1800
gactggctgc ctatcttatg ttgatgagga gtccttcaca ggcagatatt aacaaaattg   1860
tccaaattct accatgggaa cagaatgagc aagtgaagaa ctttgtggct tcccatattg   1920
ccaatatctt gaactcagaa gaattggata tccaagatct gaaaaagtta gtgaaagaag   1980
ctctgaaaga atctcaactt ccaactgtca tggacttcag aaaattctct cggaactatc   2040
aactctacaa atctgtttct cttccatcac ttgacccagc ctcagccaaa atagaaggga   2100
atcttatatt tgatccaaat aactaccttc ctaaagaaag catgctgaaa actaccctca   2160
ctgcctttgg atttgcttca gctgacctca tcgagattgg cttggaagga aaaggctttg   2220
agccaacatt ggaagctctt tttgggaagc aaggattttt cccagacagt gtcaacaaag   2280
ctttgtactg ggttaatggt caagttcctg atggtgtctc taaggtctta gtggaccact   2340
ttggctatac caaagatgat aaacatgagc aggatatggt aaatgaaata atgctcagtg   2400
ttgagaagct gattaaagat ttgaaatcca agaagtccc ggaagccaga gcctacctcc    2460
gcatcttggg agaggagctt ggttttgcca gtctccatga cctccagctc ctgggaaagc   2520
tgcttctgat gggtgcccgc actctgcagg ggatccccca tgattggga gaggtcatca    2580 ggaagggctc aaagaatgac ttttttcttc actacatctt catggagaat gcctttgaac   2640
tccccactgg agctggatta cagttgcaaa tatcttcatc tggagtcatt gctcccggag   2700
ccaaggctga gtaaaactg gaagtagcca acatgcaggc tgaactggtg caaaaccct    2760 ccgtgtctgt ggagtttgtg acaaatatgg gcatcatcat tccggacttc gctaggagtg   2820
gggtccagat gaacaccaac ttcttccacg agtcgggtct ggaggctcat gttgccctaa   2880
aagctgggaa gctgaagttt atcattcctt ccccaaagag accagtcaag ctgctcagtg   2940
gaggcaacac attacatttg gtctctacca ccaaaacgga ggtgatccca cctctcattg   3000
agaacaggca gtcctggtca gtttgcaagc aagtctttcc tggcctgaat tactgcacct   3060
caggcgctta ctccaacgcc agctccacag actccgcctc ctactatccg ctgaccgggg   3120
acaccagatt agagctggaa ctgaggccta caggagagat tgagcagtat tctgtcagcg   3180
caacctatga gctccagaga gaggacagag ccttggtgga taccctgaag tttgtaactc   3240
aagcagaagg tgcgaagcag actgaggcta ccatgacatt caaatataat cggcagagta   3300
tgaccttgtc cagtgaagtc caaattccgg attttgatgt tgacctcgga caatcctca    3360 gagttaatga tgaatctact gagggcaaaa cgtcttacag actcacctg gacattcaga    3420 acaagaaaat tactgaggtc gccctcatgg gccacctaag ttgtgacaca aaggaagaaa   3480
gaaaaatcaa gggtgttatt ccatacccc gtttgcaagc agaagccaga agtgagatcc     3540
```

-continued

```
tcgcccactg gtcgcctgcc aaactgcttc tccaaatgga ctcatctgct acagcttatg    3600
gctccacagt ttccaagagg gtggcatggc attatgatga agagaagatt gaatttgaat    3660
ggaacacagg caccaatgta gataccaaaa aaatgacttc caatttccct gtggatctct    3720
ccgattatcc taagagcttg catatgtatg ctaatagact cctggatcac agagtccctc    3780
aaacagacat gactttccgg cacgtgggtt ccaaattaat agttgcaatg agctcatggc    3840
ttcagaaggc atctgggagt cttccttata cccagacttt gcaagaccac ctcaatagcc    3900
tgaaggagtt caacctccag aacatgggat tgccagactt ccacatccca gaaaacctct    3960
tcttaaaaag cgatggccgg gtcaaatata ccttgaacaa gaacagtttg aaaattgaga    4020
ttcctttgcc ttttggtggc aaatcctcca gagatctaaa gatgttagag actgttagga    4080
caccagccct ccacttcaag tctgtgggat tccatctgcc atctcgagag ttccaagtcc    4140
ctacttttac cattcccaag ttgtatcaac tgcaagtgcc tctcctgggt gttctagacc    4200
tctccacgaa tgtctacagc aacttgtaca actggtccgc ctcctacagt ggtggcaaca    4260
ccagcacaga ccatttcagc cttcgggctc gttaccacat gaaggctgac tctgtggttg    4320
acctgctttc ctacaatgtg caaggatctg gagaacaac atatgaccac aagaatacgt      4380
tcacactatc atgtgatggg tctctacgcc acaaatttct agattcgaat atcaaattca    4440
gtcatgtaga aaaacttgga aacaacccag tctcaaaagg tttactaata ttcgatgcat    4500
ctagttcctg gggaccacag atgtctgctt cagttcattt ggactccaaa agaaacagc    4560
atttgtttgt caaagaagtc aagattgatg ggcagttcag agtctcttcg ttctatgcta    4620
aaggcacata tggcctgtct tgtcagaggg atcctaacac tggccggctc aatggagagt    4680
ccaacctgag gtttaactcc tcctacctcc aaggcaccaa ccagataaca ggaagatatg    4740
aagatggaac cctctcccct cacctccacct ctgatctgca aagtggcatc attaaaaata    4800
ctgcttccct aaagtatgag aactacgagc tgactttaaa atctgacacc aatgggaagt    4860
ataagaactt tgccacttct aacaagatgg atatgacctt ctctaagcaa aatgcactgc    4920
tgcgttctga atatcaggct gattacgagt cattgaggtt cttcagcctg ctttctggat    4980
cactaaattc ccatggtctt gagttaaatg ctgacatctt aggcactgac aaaattaata    5040
gtggtgctca aaggcgaca ctaaggattg gccaagatgg aatatctacc agtgcaacga      5100
ccaacttgaa gtgtagtctc ctggtgctgg agaatgagct gaatgcagag cttgcctctc    5160
ctggggcatc tatgaaatta caacaaatg gccgcttcag ggaacacaat gcaaaattca      5220
gtctggatgg gaaagccgcc ctcacagagc tatcactggg aagtgcttat caggccatga    5280
ttctgggtgt cgacagcaaa aacatttttca acttcaaggt cagtcaagaa ggacttaagc    5340
tctcaaatga catgatgggc tcatatgctg aaatgaaatt tgaccacaca aacagtctga    5400
acattgcagg cttatcactg gacttctctt caaaacttga acacatttac agctctgaca    5460
agttttataa gcaaactgtt aatttacagc tacagcccta ttctctggta actactttaa    5520
acagtgacct gaaatacaat gctctggatc tcaccaacaa tgggaaacta cggctagaac    5580
ccctgaagct gcatgtggct ggtaacctaa aaggagccta ccaaaataat gaaataaaac    5640
acatctatgc catctcttct gctgccttat cagcaagcta taaagcagac actgttgcta    5700
aggttcaggg tgtggagttt agccatcggc tcaacacaga catcgctggg ctggcttcag    5760
ccattgacat gagcacaaac tataattcag actcactgca tttcagcaat gtcttccgtt    5820
ctgtaatggc cccgtttacc atgaccatcg atgcacatac aaatggcaat gggaaactcg    5880
ctctctgggg agaacatact gggcagctgt atagcaaatt cctgttgaaa gcagaacctc    5940
```

-continued

```
tggcatttac tttctctcat gattacaaag gctccacaag tcatcatctc gtgtctagga      6000
aaagcatcag tgcagctctt gaacacaaag tcagtgccct gcttactcca gctgagcaga      6060
caggcacctg gaaactcaag acccaattta acaacaatga atacagccag gacttggatg      6120
cttacaacac taaagataaa attggcgtgg agcttactgg acgaactctg gctgacctaa      6180
ctctactaga ctccccaatt aaagtgccac ttttactcag tgagcccatc aatatcattg      6240
atgctttaga gatgagagat gccgttgaga agccccaaga atttacaatt gttgcttttg      6300
taaagtatga taaaaaccaa gatgttcact ccattaacct cccattttt gagaccttgc       6360 aagaatattt tgagaggaat cgacaaacca ttatagttgt actggaaaac gtacagagaa      6420
acctgaagca catcaatatt gatcaatttg taagaaaata cagagcagcc ctgggaaaac      6480
tcccacagca agctaatgat tatctgaatt cattcaattg ggagagacaa gtttcacatg      6540
ccaaggagaa actgactgct ctcacaaaaa agtatagaat tacagaaaat gatatacaaa      6600
ttgcattaga tgatgccaaa atcaacttta atgaaaaact atctcaactg cagacatata      6660
tgatacaatt tgatcagtat attaaagata gttatgattt acatgatttg aaaatagcta      6720
ttgctaatat tattgatgaa atcattgaaa aattaaaaag tcttgatgag cactatcata      6780
tccgtgtaaa tttagtaaaa acaatccatg atctacattt gtttattgaa atattgatt       6840 ttaacaaaag tggaagtagt actgcatcct ggattcaaaa tgtggatact aagtaccaaa      6900
tcagaatcca gatacaagaa aaactgcagc agcttaagag acacatacag aatatagaca      6960
tccagcacct agctggaaag ttaaaacaac acattgaggc tattgatgtt agagtgcttt      7020
tagatcaatt gggaactaca atttcatttg aagaataaa tgacgttctt gagcatgtca       7080
aacactttgt tataaatctt attggggatt ttgaagtagc tgagaaaatc aatgccttca      7140
gagccaaagt ccatgagtta atcgagaggt atgaagtaga ccaacaaatc caggtttaa       7200 tggataaatt agtagagttg gcccaccaat acaagttgaa ggagactatt cagaagctaa      7260
gcaatgtcct acaacaagtt aagataaaag attactttga gaaattggtt ggatttattg      7320
atgatgctgt caagaagctt aatgaattat cttttaaaac attcattgaa gatgttaaca      7380
aattccttga catgttgata aagaaattaa agtcatttga ttaccaccag tttgtagatg      7440
aaaccaatga caaaatccgt gaggtgactc agagactcaa tggtgaaatt caggctctgg      7500
aactaccaca aaaagctgaa gcattaaaac tgttttaga ggaaaccaag gccacagttg       7560
cagtgtatct ggaaagccta caggacacca aaataacctt aatcatcaat tggttacagg      7620
aggctttaag ttcagcatct ttggctcaca tgaaggccaa attccgagag accctagaag      7680
atacacgaga ccgaatgtat caaatggaca ttcagcagga acttcaacga tacctgtctc      7740
tggtaggcca ggtttatagc acacttgtca cctacatttc tgattggtgg actcttgctg      7800
ctaagaacct tactgacttt gcagagcaat attctatcca agattgggct aaacgtatga      7860
aagcattggt agagcaaggg ttcactgttc ctgaaatcaa gaccatcctt gggaccatgc      7920
ctgcctttga agtcagtctt caggctcttc agaaagctac cttccagaca cctgatttta      7980 tagtcccct aacagatttg aggattccat cagttcagat aaacttcaaa gacttaaaaa       8040
atataaaaat cccatccagg ttttccacac cagaatttac catccttaac accttccaca      8100
ttccttcctt tacaattgac tttgtagaaa tgaaagtaaa gatcatcaga accattgacc      8160
agatgctgaa cagtgagctg cagtggcccg ttccagatat atatctcagg gatctgaagg      8220
tggaggacat tcctctagcg agaatcaccc tgccagactt ccgttaccca gaaatcgcaa      8280
ttccagaatt cataatccca actctcaacc ttaatgattt tcaagttcct gaccttcaca      8340
```

```
taccagaatt ccagcttccc cacatctcac acacaattga agtacctact tttggcaagc    8400
tatacagtat tctgaaaatc caatctcctc ttttcacatt agatgcaaat gctgacatag    8460
ggaatggaac cacctcagca aacgaagcag gtatcgcagc ttccatcact gccaaaggag    8520
agtccaaatt agaagttctc aattttgatt ttcaagcaaa tgcacaactc tcaaacccta    8580
agattaatcc gctggctctg aaggagtcag tgaagttctc cagcaagtac ctgagaacgg    8640
agcatgggag tgaaatgctg ttttttggaa atgctattga gggaaaatca aacacagtgg    8700
caagtttaca cacagaaaaa aatacactgg agcttagtaa tggagtgatt gtcaagataa    8760
acaatcagct taccctggat agcaacacta aatacttcca caattgaac atccccaaac     8820 tggacttctc tagtcaggct gacctgcgca acgagatcaa gacactgttg aaagctggcc    8880
acatagcatg gacttcttct ggaaaagggt catggaaatg gcctgcccc agattctcag     8940 atgagggaac acatgaatca caaattagtt tcaccataga aggacccctc acttcctttg    9000
gactgtccaa taagatcaat agcaaacacc taagagtaaa ccaaaacttg gtttatgaat    9060
ctggctccct caacttttct aaacttgaaa ttcaatcaca agtcgattcc cagcatgtgg    9120
gccacagtgt tctaactgct aaaggcatgg cactgtttgg agaagggaag gcagagttta    9180
ctgggaggca tgatgctcat ttaaatgaaa aggttattgg aactttgaaa aattctcttt    9240
tcttttcagc ccagccattt gagatcacgg catccacaaa caatgaaggg aatttgaaag    9300
ttcgttttcc attaaggtta acagggaaga tagacttcct gaataactat gcactgtttc    9360
tgagtcccag tgcccagcaa gcaagttggc aagtaagtgc taggttcaat cagtataagt    9420
acaaccaaaa tttctctgct ggaaacaacg agaacattat ggaggcccat gtaggaataa    9480
atggagaagc aaatctggat ttcttaaaca ttccttttaac aattcctgaa atgcgtctac    9540
cttacacaat aatcacaact cctccactga aagattctc tctatgggaa aaaacaggct     9600
tgaaggaatt cttgaaaacg acaaagcaat catttgattt aagtgtaaaa gctcagtata    9660
agaaaaacaa acacaggcat tccatcacaa atccttggc tgtgctttgt gagtttatca     9720
gtcagagcat caaatccttt gacaggcatt ttgaaaaaaa cagaaacaat gcattagatt    9780
ttgtcaccaa atcctataat gaaacaaaaa ttaagtttga taagtacaaa gctgaaaaat    9840
ctcacgacga gctccccagg accttcaaa ttcctggata cactgttcca gttgtcaatg     9900
ttgaagtgtc tccattcacc atagagatgt cggcattcgg ctatgtgttc ccaaaagcag    9960
tcagcatgcc tagtttctcc atcctaggtt ctgacgtccg tgtgccttca tacacattaa    10020
tcctgccatc attagagctg ccagtccttc atgtccctag aaatctcaag ctttctcttc    10080
cagatttcaa ggaattgtgt accataagcc atattttat tcctgccatg gcaatatta     10140 cctatgattt ctccttaaa tcaagtgtca tcacactgaa taccaatgct gaacttttta    10200
accagtcaga tattgttgct catctccttt cttcatcttc atctgtcatt gatgcactgc    10260
agtacaaatt agagggcacc acaagattga caagaaaaag gggattgaag ttagccacag    10320
ctctgtctct gagcaacaaa tttgtggagg gtagtcataa cagtactgtg agcttaacca    10380
cgaaaaatat ggaagtgtca gtggcaacaa ccacaaaagc ccaaattcca attttgagaa    10440
tgaatttcaa gcaagaactt aatgaaaata ccaagtcaaa acctactgtc tcttcctcca    10500
tggaatttaa gtatgatttc aattcttcaa tgctgtactc taccgctaaa ggagcagttg    10560
accacaagct tagcttggaa agcctcacct cttactttc cattgagtca tctaccaaag    10620
gagatgtcaa gggttcggtt cttctctcggg aatattcagg aactattgct agtgaggcca    10680
acacttactt gaattccaag agcacacggt cttcagtgaa gctgcagggc acttccaaaa    10740
```

```
ttgatgatat ctggaacctt gaagtaaaag aaaattttgc tggagaagcc acactccaac    10800
gcatatattc cctctgggag cacagtacga aaaaccactt acagctagag ggcctctttt    10860
tcaccaacgg agaacataca agcaaagcca ccctggaact ctctccatgg caaatgtcag    10920
ctcttgttca ggtccatgca agtcagccca gttccttcca tgatttccct gaccttggcc    10980
aggaagtggc cctgaatgct aacactaaga accagaagat cagatggaaa aatgaagtcc    11040
ggattcattc tgggtctttc cagagccagg tcgagctttc caatgaccaa gaaaaggcac    11100
accttgacat tgcaggatcc ttagaaggac acctaaggtt cctcaaaaat atcatcctac    11160
cagtctatga caagagctta tgggattttcc taaagctgga tgtaaccacc agcattggta    11220
ggagacagca tcttcgtgtt tcaactgcct tgtgtacac caaaaacccc aatggctatt    11280
cattctccat ccctgtaaaa gttttggctg ataaattcat tattcctggg ctgaaactaa    11340
atgatctaaa ttcagttctt gtcatgccta cgttccatgt cccatttaca gatcttcagg    11400
ttccatcgtg caaacttgac ttcagagaaa tacaaatcta taagaagctg agaacttcat    11460
catttgccct caacctacca acactccccg aggtaaaatt ccctgaagtt gatgtgttaa    11520
caaaatattc tcaaccagaa gactccttga ttcccttttt tgagataacc gtgcctgaat    11580
ctcagttaac tgtgtcccag ttcacgcttc caaaaagtgt ttcagatggc attgctgctt    11640
tggatctaaa tgcagtagcc aacaagatcg cagactttga gttgcccacc atcatcgtgc    11700
ctgagcagac cattgagatt ccctccatta agttctctgt acctgctgga attgtcattc    11760
cttcctttca agcactgact gcacgctttg aggtagactc tcccgtgtat aatgccactt    11820
ggagtgccag tttgaaaaac aaagcagatt atgttgaaac agtcctggat tccacatgca    11880
gctcaaccgt acagttccta gaatatgaac taaatgtttt gggaacacac aaaatcgaag    11940
atggtacgtt agcctctaag actaaaggaa catttgcaca ccgtgacttc agtgcagaat    12000
atgaagaaga tggcaaatat gaaggacttc aggaatggga aggaaaagcg cacctcaata    12060
tcaaaagccc agcgttcacc gatctccatc tgcgctacca gaaagacaag aaaggcatct    12120
ccacctcagc agcctcccca gccgtaggca ccgtgggcat ggatatggat gaagatgacg    12180 actttctaa atggaacttc tactacagcc ctcagtcctc tccagataaa aaactcacca    12240
tattcaaaac tgagttgagg gtccgggaat ctgatgagga aactcagatc aaagttaatt    12300
gggaagaaga ggcagcttct ggcttgctaa cctctctgaa agacaacgtg cccaaggcca    12360
caggggtcct ttatgattat gtcaacaagt accactggga acacacaggg ctcaccctga    12420
gagaagtgtc ttcaaagctg agaagaaatc tgcagaacaa tgctgagtgg gttatcaag    12480 gggccattag gcaaattgat gatatcgacg tgaggttcca gaaagcagcc agtggcacca    12540
ctgggaccta ccaagagtgg aaggacaagg cccagaatct gtaccaggaa ctgttgactc    12600
aggaaggcca agccagtttc cagggactca aggataacgt gtttgatggc ttggtacgag    12660
ttactcaaga attccatatg aaagtcaagc atctgattga ctcactcatt gattttctga    12720
acttccccag attccagtt ccggggaaac ctggatatat cactagggag aactttgca    12780 ctatgttcat aagggaggta gggacggtac tgtcccaggt atattcgaaa gtccataatg    12840
gttcagaaat actgttttcc tatttccaag acctagtgat tacacttcct ttcgagttaa    12900
ggaaacataa actaatagat gtaatctcga tgtatagga actgttgaaa gatttatcaa    12960
aagaagccca agaggtattt aaagccattc agtctctcaa gaccacagag gtgctacgta    13020
atcttcagga ccttttacaa ttcatttttcc aactaataga agataacatt aaacagctga    13080
aagagatgaa atttacttat cttattaatt atatccaaga tgagatcaac acaatcttca    13140
```

```
gtgattatat cccatatgtt tttaaattgt tgaaagaaaa cctatgcctt aatcttcata    13200
agttcaatga atttattcaa aacgagcttc aggaagcttc tcaagagtta cagcagatcc    13260
atcaatacat tatggcccct cgtgaagaat attttgatcc aagtatagtt ggctggacag    13320
tgaaatatta tgaacttgaa gaaagatag tcagtctgat caagaacctg ttagttgctc     13380
ttaaggactt ccattctgaa tatattgtca gtgcctctaa ctttacttcc caactctcaa    13440
gtcaagttga gcaatttctg cacagaaata ttcaggaata tcttagcatc cttaccgatc    13500
cagatggaaa agggaaagag aagattgcag agctttctgc cactgctcag gaaataatta    13560
aaagccaggc cattgcgacg aagaaaataa tttctgatta ccaccagcag tttagatata    13620
aactgcaaga ttttcagac caactctctg attactatga aaaatttatt gctgaatcca     13680
aaagattgat tgacctgtcc attcaaaact accacacatt tctgatatac atcacggagt    13740
tactgaaaaa gctgcaatca accacagtca tgaacccta catgaagctt gctccaggag     13800
aacttactat catcctctaa tttttaaaa gaaatcttca tttattcttc ttttccaatt     13860
gaactttcac atagcacaga aaaaattcaa actgcctata ttgataaaac catacagtga    13920
gccagccttg cagtaggcag tagactataa gcagaagcac atatgaactg gacctgcacc    13980
aaagctggca ccagggctcg gaaggtctct gaactcagaa ggatggcatt ttttgcaagt    14040
taaagaaaat caggatctga gttatttgc taaacttggg ggaggaggaa caaataaatg      14100
gagtctttat tgtgtatcat a                                              14121

<210> SEQ ID NO 28
<211> LENGTH: 4505
<212> TYPE: PRT
<213> ORGANISM: Mus musculus

<400> SEQUENCE: 28

Met Gly Pro Arg Lys Pro Ala Leu Arg Thr Pro Leu Leu Leu Phe
1               5                   10                  15

Leu Leu Leu Phe Leu Asp Thr Ser Val Trp Ala Gln Asp Glu Val Leu
                20                  25                  30

Glu Asn Leu Ser Phe Ser Cys Pro Lys Asp Ala Thr Arg Phe Lys His
            35                  40                  45

Leu Arg Lys Tyr Val Tyr Asn Tyr Glu Ala Glu Ser Ser Ser Gly Val
        50                  55                  60

Gln Gly Thr Ala Asp Ser Arg Ser Ala Thr Lys Ile Asn Cys Lys Val
65                  70                  75                  80

Glu Leu Glu Val Pro Gln Ile Cys Gly Phe Ile Met Arg Thr Asn Gln
                85                  90                  95

Cys Thr Leu Lys Glu Val Tyr Gly Phe Asn Pro Glu Gly Lys Ala Leu
            100                 105                 110

Met Lys Lys Thr Lys Asn Ser Glu Glu Phe Ala Ala Ala Met Ser Arg
        115                 120                 125

Tyr Glu Leu Lys Leu Ala Ile Pro Glu Gly Lys Gln Ile Val Leu Tyr
    130                 135                 140

Pro Asp Lys Asp Glu Pro Lys Tyr Ile Leu Asn Ile Lys Arg Gly Ile
145                 150                 155                 160

Ile Ser Ala Leu Leu Val Pro Pro Glu Thr Glu Glu Asp Gln Gln Glu
                165                 170                 175

Leu Phe Leu Asp Thr Val Tyr Gly Asn Cys Ser Thr Gln Val Thr Val
            180                 185                 190
```

-continued

```
Asn Ser Arg Lys Gly Thr Val Pro Thr Glu Met Ser Thr Glu Arg Asn
            195                 200                 205

Leu Gln Gln Cys Asp Gly Phe Gln Pro Ile Ser Thr Ser Val Ser Pro
    210                 215                 220

Leu Ala Leu Ile Lys Gly Leu Val His Pro Leu Ser Thr Leu Ile Ser
225                 230                 235                 240

Ser Ser Gln Thr Cys Gln Tyr Thr Leu Asp Pro Lys Arg Lys His Val
                245                 250                 255

Ser Glu Ala Val Cys Asp Glu Gln His Leu Phe Leu Pro Phe Ser Tyr
            260                 265                 270

Lys Asn Lys Tyr Gly Ile Met Thr Arg Val Thr Gln Lys Leu Ser Leu
        275                 280                 285

Glu Asp Thr Pro Lys Ile Asn Ser Arg Phe Phe Ser Glu Gly Thr Asn
    290                 295                 300

Arg Met Gly Leu Ala Phe Glu Ser Thr Lys Ser Thr Ser Ser Pro Lys
305                 310                 315                 320

Gln Ala Asp Ala Val Leu Lys Thr Leu Gln Glu Leu Lys Lys Leu Ser
                325                 330                 335

Ile Ser Glu Gln Asn Ala Gln Arg Ala Asn Leu Phe Asn Lys Leu Val
            340                 345                 350

Thr Glu Leu Arg Gly Leu Thr Gly Glu Ala Ile Thr Ser Leu Leu Pro
        355                 360                 365

Gln Leu Ile Glu Val Ser Ser Pro Ile Thr Leu Gln Ala Leu Val Gln
    370                 375                 380

Cys Gly Gln Pro Gln Cys Tyr Thr His Ile Leu Gln Trp Leu Lys Thr
385                 390                 395                 400

Glu Lys Ala His Pro Leu Leu Val Asp Ile Val Thr Tyr Leu Met Ala
                405                 410                 415

Leu Ile Pro Asn Pro Ser Thr Gln Arg Leu Gln Glu Ile Phe Asn Thr
            420                 425                 430

Ala Lys Glu Gln Gln Ser Arg Ala Thr Leu Tyr Ala Leu Ser His Ala
        435                 440                 445

Val Asn Ser Tyr Phe Asp Val Asp His Ser Arg Ser Pro Val Leu Gln
    450                 455                 460

Asp Ile Ala Gly Tyr Leu Leu Lys Gln Ile Asp Asn Glu Cys Thr Gly
465                 470                 475                 480

Asn Glu Asp His Thr Phe Leu Ile Leu Arg Val Ile Gly Asn Met Gly
                485                 490                 495

Arg Thr Met Glu Gln Val Met Pro Ala Leu Lys Ser Ser Val Leu Ser
            500                 505                 510

Cys Val Arg Ser Thr Lys Pro Ser Leu Leu Ile Gln Lys Ala Ala Leu
        515                 520                 525

Gln Ala Leu Arg Lys Met Glu Leu Glu Asp Glu Val Arg Thr Ile Leu
    530                 535                 540

Phe Asp Thr Phe Val Asn Gly Val Ala Pro Val Glu Lys Arg Leu Ala
545                 550                 555                 560

Ala Tyr Leu Leu Leu Met Lys Asn Pro Ser Ser Asp Ile Asn Lys
                565                 570                 575

Ile Ala Gln Leu Leu Gln Trp Glu Gln Ser Glu Gln Val Lys Asn Phe
            580                 585                 590

Val Ala Ser His Ile Ala Asn Ile Leu Asn Ser Glu Glu Leu Tyr Val
        595                 600                 605
```

```
Gln Asp Leu Lys Val Leu Ile Lys Asn Ala Leu Glu Asn Ser Gln Phe
    610                 615                 620

Pro Thr Ile Met Asp Phe Arg Lys Phe Ser Arg Asn Tyr Gln Ile Ser
625                 630                 635                 640

Lys Ser Ala Ser Leu Pro Met Phe Asp Pro Val Ser Val Lys Ile Glu
                645                 650                 655

Gly Asn Leu Ile Phe Asp Pro Ser Ser Tyr Leu Pro Arg Glu Ser Leu
                660                 665                 670

Leu Lys Thr Thr Leu Thr Val Phe Gly Leu Ala Ser Leu Asp Leu Phe
            675                 680                 685

Glu Ile Gly Leu Glu Gly Lys Gly Phe Glu Pro Thr Leu Glu Ala Leu
        690                 695                 700

Phe Gly Lys Gln Gly Phe Phe Pro Asp Ser Val Asn Lys Ala Leu Tyr
705                 710                 715                 720

Trp Val Asn Gly Arg Val Pro Asp Gly Val Ser Lys Val Leu Val Asp
                725                 730                 735

His Phe Gly Tyr Thr Thr Asp Gly Lys His Glu Gln Asp Met Val Asn
            740                 745                 750

Gly Ile Met Pro Ile Val Asp Lys Leu Ile Lys Asp Leu Lys Ser Lys
        755                 760                 765

Glu Ile Pro Glu Ala Arg Ala Tyr Leu Arg Ile Leu Gly Lys Glu Leu
770                 775                 780

Ser Phe Val Arg Leu Gln Asp Leu Gln Val Leu Gly Lys Leu Leu Leu
785                 790                 795                 800

Ser Gly Ala Gln Thr Leu Gln Gly Ile Pro Gln Met Val Val Gln Ala
                805                 810                 815

Ile Arg Glu Gly Ser Lys Asn Asp Leu Phe Leu His Tyr Ile Phe Met
                820                 825                 830

Asp Asn Ala Phe Glu Leu Pro Thr Gly Ala Gly Leu Gln Leu Gln Val
            835                 840                 845

Ser Ser Ser Gly Val Phe Thr Pro Gly Ile Lys Ala Gly Val Arg Leu
850                 855                 860

Glu Leu Ala Asn Ile Gln Ala Glu Leu Val Ala Lys Pro Ser Val Ser
865                 870                 875                 880

Leu Glu Phe Val Thr Asn Met Gly Ile Ile Pro Asp Phe Ala Lys
                885                 890                 895

Ser Ser Val Gln Met Asn Thr Asn Phe Phe His Glu Ser Gly Leu Glu
                900                 905                 910

Ala Arg Val Ala Leu Lys Ala Gly Gln Leu Lys Val Ile Ile Pro Ser
            915                 920                 925

Pro Lys Arg Pro Val Lys Leu Phe Ser Gly Ser Asn Thr Leu His Leu
        930                 935                 940

Val Ser Thr Thr Lys Thr Glu Val Ile Pro Leu Val Glu Asn Arg
945                 950                 955                 960

Gln Ser Trp Ser Thr Cys Lys Pro Leu Phe Thr Gly Met Asn Tyr Cys
                965                 970                 975

Thr Thr Gly Ala Tyr Ser Asn Ala Ser Ser Thr Glu Ser Ala Ser Tyr
            980                 985                 990

Tyr Pro Leu Thr Gly Asp Thr Arg  Tyr Glu Leu Glu Leu Arg Pro Thr
        995                1000                1005

Gly Glu  Val Glu Gln Tyr Ser  Ala Thr Ala Thr Tyr  Glu Leu Leu
    1010                1015                1020
```

-continued

```
Lys Glu Asp Lys Ser Leu Val Asp Thr Leu Lys Phe Leu Val Gln
1025                1030                1035

Ala Glu Gly Val Gln Gln Ser Glu Ala Thr Val Leu Phe Lys Tyr
1040                1045                1050

Asn Arg Arg Ser Arg Thr Leu Ser Ser Glu Val Leu Ile Pro Gly
1055                1060                1065

Phe Asp Val Asn Phe Gly Thr Ile Leu Arg Val Asn Asp Glu Ser
1070                1075                1080

Ala Lys Asp Lys Asn Thr Tyr Lys Leu Ile Leu Asp Ile Gln Asn
1085                1090                1095

Lys Lys Ile Thr Glu Val Ser Leu Val Gly His Leu Ser Tyr Asp
1100                1105                1110

Lys Lys Gly Asp Gly Lys Ile Lys Gly Val Val Ser Ile Pro Arg
1115                1120                1125

Leu Gln Ala Glu Ala Arg Ser Glu Val His Thr His Trp Ser Ser
1130                1135                1140

Thr Lys Leu Leu Phe Gln Met Asp Ser Ser Ala Thr Ala Tyr Gly
1145                1150                1155

Ser Thr Ile Ser Lys Arg Val Thr Trp Arg Tyr Asp Asn Glu Ile
1160                1165                1170

Ile Glu Phe Asp Trp Asn Thr Gly Thr Asn Val Asp Thr Lys Lys
1175                1180                1185

Val Ala Ser Asn Phe Pro Val Asp Leu Ser His Tyr Pro Arg Met
1190                1195                1200

Leu His Glu Tyr Ala Asn Gly Leu Leu Asp His Arg Val Pro Gln
1205                1210                1215

Thr Asp Val Thr Phe Arg Asp Met Gly Ser Lys Leu Ile Val Ala
1220                1225                1230

Thr Asn Thr Trp Leu Gln Met Ala Thr Arg Gly Leu Pro Tyr Pro
1235                1240                1245

Gln Thr Leu Gln Asp His Leu Asn Ser Leu Ser Glu Leu Asn Leu
1250                1255                1260

Leu Lys Met Gly Leu Ser Asp Phe His Ile Pro Asp Asn Leu Phe
1265                1270                1275

Leu Lys Thr Asp Gly Arg Val Lys Tyr Thr Met Asn Arg Asn Lys
1280                1285                1290

Ile Asn Ile Asp Ile Pro Leu Pro Leu Gly Gly Lys Ser Ser Lys
1295                1300                1305

Asp Leu Lys Met Pro Glu Ser Val Arg Thr Pro Ala Leu Asn Phe
1310                1315                1320

Lys Ser Val Gly Phe His Leu Pro Ser Arg Glu Val Gln Val Pro
1325                1330                1335

Thr Phe Thr Ile Pro Lys Thr His Gln Leu Gln Val Pro Leu Leu
1340                1345                1350

Gly Val Leu Asp Leu Ser Thr Asn Val Tyr Ser Asn Leu Tyr Asn
1355                1360                1365

Trp Ser Ala Ser Tyr Thr Gly Gly Asn Thr Ser Arg Asp His Phe
1370                1375                1380

Ser Leu Gln Ala Gln Tyr Arg Met Lys Thr Asp Ser Val Val Asp
1385                1390                1395

Leu Phe Ser Tyr Ser Val Gln Gly Ser Gly Glu Thr Thr Tyr Asp
1400                1405                1410
```

```
Ser Lys Asn Thr Phe Thr Leu Ser Cys Asp Gly Ser Leu His His
1415                1420                1425

Lys Phe Leu Asp Ser Lys Phe Lys Val Ser His Val Glu Lys Phe
1430                1435                1440

Gly Asn Ser Pro Val Ser Lys Gly Leu Leu Thr Phe Glu Thr Ser
1445                1450                1455

Ser Ala Leu Gly Pro Gln Met Ser Ala Thr Val His Leu Asp Ser
1460                1465                1470

Lys Lys Lys Gln His Leu Tyr Val Lys Asp Ile Lys Val Asp Gly
1475                1480                1485

Gln Phe Arg Ala Ser Ser Phe Tyr Ala Gln Gly Lys Tyr Gly Leu
1490                1495                1500

Ser Cys Glu Arg Asp Val Thr Thr Gly Gln Leu Ser Gly Glu Ser
1505                1510                1515

Asn Met Arg Phe Asn Ser Thr Tyr Phe Gln Gly Thr Asn Gln Ile
1520                1525                1530

Val Gly Met Tyr Gln Asp Gly Ala Leu Ser Ile Thr Ser Thr Ser
1535                1540                1545

Asp Leu Gln Asp Gly Ile Phe Lys Asn Thr Ala Ser Leu Lys Tyr
1550                1555                1560

Glu Asn Tyr Glu Leu Thr Leu Lys Ser Asp Ser Ser Gly Gln Tyr
1565                1570                1575

Glu Asn Phe Ala Ala Ser Asn Lys Leu Asp Val Thr Phe Ser Thr
1580                1585                1590

Gln Ser Ala Leu Leu Arg Ser Glu His Gln Ala Asn Tyr Lys Ser
1595                1600                1605

Leu Arg Leu Val Thr Leu Leu Ser Gly Ser Leu Thr Ser Gln Gly
1610                1615                1620

Val Glu Leu Asn Ala Asp Ile Leu Gly Thr Asp Lys Ile Asn Thr
1625                1630                1635

Gly Ala His Lys Ala Thr Leu Lys Ile Ala Arg Asp Gly Leu Ser
1640                1645                1650

Thr Ser Ala Thr Thr Asn Leu Lys Tyr Ser Pro Leu Leu Leu Glu
1655                1660                1665

Asn Glu Leu Asn Ala Glu Leu Gly Leu Ser Gly Ala Ser Met Lys
1670                1675                1680

Leu Ser Thr Asn Gly Arg Phe Lys Glu His His Ala Lys Phe Ser
1685                1690                1695

Leu Asp Gly Arg Ala Ala Leu Thr Glu Val Ser Leu Gly Ser Ile
1700                1705                1710

Tyr Gln Ala Met Ile Leu Gly Ala Asp Ser Lys Asn Ile Phe Asn
1715                1720                1725

Phe Lys Leu Ser Arg Glu Gly Leu Arg Leu Ser Asn Asp Leu Met
1730                1735                1740

Gly Ser Tyr Ala Glu Met Lys Leu Asp His Thr His Ser Leu Asn
1745                1750                1755

Ile Ala Gly Leu Ser Leu Asp Phe Phe Ser Lys Met Asp Asn Ile
1760                1765                1770

Tyr Ser Gly Asp Lys Phe Tyr Lys Gln Asn Phe Asn Leu Gln Leu
1775                1780                1785

Gln Pro Tyr Ser Phe Ile Thr Thr Leu Ser Asn Asp Leu Arg Tyr
1790                1795                1800
```

-continued

```
Gly Ala Leu Asp Leu Thr Asn Asn Gly Arg Phe Arg Leu Glu Pro
    1805                1810                1815
Leu Lys Leu Asn Val Gly Gly Asn Phe Lys Gly Thr Tyr Gln Asn
    1820                1825                1830
Asn Glu Leu Lys His Ile Tyr Thr Ile Ser Tyr Thr Asp Leu Val
    1835                1840                1845
Val Ala Ser Tyr Arg Ala Asp Thr Val Ala Lys Val Gln Gly Val
    1850                1855                1860
Glu Phe Ser His Arg Leu Asn Ala Asp Ile Glu Gly Leu Thr Ser
    1865                1870                1875
Ser Val Asp Val Thr Thr Ser Tyr Asn Ser Asp Pro Leu His Phe
    1880                1885                1890
Asn Asn Val Phe His Phe Ser Leu Ala Pro Phe Thr Leu Gly Ile
    1895                1900                1905
Asp Thr His Thr Ser Gly Asp Gly Lys Leu Ser Phe Trp Gly Glu
    1910                1915                1920
His Thr Gly Gln Leu Tyr Ser Lys Phe Leu Leu Lys Ala Glu Pro
    1925                1930                1935
Leu Ala Leu Ile Val Ser His Asp Tyr Lys Gly Ser Thr Ser His
    1940                1945                1950
Ser Leu Pro Tyr Glu Ser Ser Ile Ser Thr Ala Leu Glu His Thr
    1955                1960                1965
Val Ser Ala Leu Leu Thr Pro Ala Glu Gln Thr Ser Thr Trp Lys
    1970                1975                1980
Phe Lys Thr Lys Leu Asn Asp Lys Val Tyr Ser Gln Asp Phe Glu
    1985                1990                1995
Ala Tyr Asn Thr Lys Asp Lys Ile Gly Val Glu Leu Ser Gly Arg
    2000                2005                2010
Ala Asp Leu Ser Gly Leu Tyr Ser Pro Ile Lys Leu Pro Phe Phe
    2015                2020                2025
Tyr Ser Glu Pro Val Asn Val Leu Asn Gly Leu Glu Val Asn Asp
    2030                2035                2040
Ala Val Asp Lys Pro Gln Glu Phe Thr Ile Ile Ala Val Val Lys
    2045                2050                2055
Tyr Asp Lys Asn Gln Asp Val His Thr Ile Asn Leu Pro Phe Phe
    2060                2065                2070
Lys Ser Leu Pro Asp Tyr Leu Glu Arg Asn Arg Arg Gly Met Ile
    2075                2080                2085
Ser Leu Leu Glu Ala Met Arg Gly Glu Leu Gln Arg Leu Ser Val
    2090                2095                2100
Asp Gln Phe Val Arg Lys Tyr Arg Ala Ala Leu Ser Arg Leu Pro
    2105                2110                2115
Gln Gln Ile His His Tyr Leu Asn Ala Ser Asp Trp Glu Arg Gln
    2120                2125                2130
Val Ala Gly Ala Lys Glu Lys Ile Thr Ser Phe Met Glu Asn Tyr
    2135                2140                2145
Arg Ile Thr Asp Asn Asp Val Leu Ile Ala Ile Asp Ser Ala Lys
    2150                2155                2160
Ile Asn Phe Asn Glu Lys Leu Ser Gln Leu Glu Thr Tyr Ala Ile
    2165                2170                2175
Gln Phe Asp Gln Tyr Ile Lys Asp Asn Tyr Asp Pro His Asp Leu
    2180                2185                2190
```

```
Lys Arg Thr Ile Ala Glu Ile Ile Asp Arg Ile Ile Glu Lys Leu
    2195                2200                2205

Lys Ile Leu Asp Glu Gln Tyr His Ile Arg Val Asn Leu Ala Lys
    2210                2215                2220

Ser Ile His Asn Leu Tyr Leu Phe Val Glu Asn Val Asp Leu Asn
    2225                2230                2235

Gln Val Ser Ser Ser Asn Thr Ser Trp Ile Gln Asn Val Asp Ser
    2240                2245                2250

Asn Tyr Gln Val Arg Ile Gln Ile Gln Glu Lys Leu Gln Gln Leu
    2255                2260                2265

Arg Thr Gln Ile Gln Asn Ile Asp Ile Gln Gln Leu Ala Ala Glu
    2270                2275                2280

Val Lys Arg Gln Met Asp Ala Ile Asp Val Thr Met His Leu Asp
    2285                2290                2295

Gln Leu Arg Thr Ala Ile Leu Phe Gln Arg Ile Ser Asp Ile Ile
    2300                2305                2310

Asp Arg Val Lys Tyr Phe Val Met Asn Leu Ile Glu Asp Phe Lys
    2315                2320                2325

Val Thr Glu Lys Ile Asn Thr Phe Arg Val Ile Val Arg Glu Leu
    2330                2335                2340

Ile Glu Lys Tyr Glu Val Asp Gln His Ile Gln Val Leu Met Asp
    2345                2350                2355

Lys Ser Val Glu Leu Ala His Arg Tyr Ser Leu Ser Glu Pro Leu
    2360                2365                2370

Gln Lys Leu Ser Asn Val Leu Gln Arg Ile Glu Ile Lys Asp Tyr
    2375                2380                2385

Tyr Glu Lys Leu Val Gly Phe Ile Asp Asp Thr Val Glu Trp Leu
    2390                2395                2400

Lys Ala Leu Ser Phe Lys Asn Thr Ile Glu Glu Leu Asn Arg Leu
    2405                2410                2415

Thr Asp Met Leu Val Lys Lys Leu Lys Ala Phe Asp Tyr His Gln
    2420                2425                2430

Phe Val Asp Lys Thr Asn Ser Lys Ile Arg Glu Met Thr Gln Arg
    2435                2440                2445

Ile Asn Ala Glu Ile Gln Ala Leu Lys Leu Pro Gln Lys Met Glu
    2450                2455                2460

Ala Leu Lys Leu Leu Val Glu Asp Phe Lys Thr Thr Val Ser Asn
    2465                2470                2475

Ser Leu Glu Arg Leu Lys Asp Thr Lys Val Thr Val Val Ile Asp
    2480                2485                2490

Trp Leu Gln Asp Ile Leu Thr Gln Met Lys Asp His Phe Gln Asp
    2495                2500                2505

Thr Leu Glu Asp Val Arg Asp Arg Ile Tyr Gln Met Asp Ile Gln
    2510                2515                2520

Arg Glu Leu Glu His Phe Leu Ser Leu Val Asn Gln Val Tyr Ser
    2525                2530                2535

Thr Leu Val Thr Tyr Met Ser Asp Trp Trp Thr Leu Thr Ala Lys
    2540                2545                2550

Asn Ile Thr Asp Phe Ala Glu Gln Tyr Ser Ile Gln Asn Trp Ala
    2555                2560                2565

Glu Ser Ile Lys Val Leu Val Glu Gln Gly Phe Ile Val Pro Glu
    2570                2575                2580
```

```
Met Gln Thr Phe Leu Trp Thr Met Pro Ala Phe Glu Val Ser Leu
2585                2590                2595

Arg Ala Leu Gln Glu Gly Asn Phe Gln Thr Pro Val Phe Ile Val
2600                2605                2610

Pro Leu Thr Asp Leu Arg Ile Pro Ser Ile Arg Ile Asn Phe Lys
2615                2620                2625

Met Leu Lys Asn Ile Lys Ile Pro Leu Arg Phe Ser Thr Pro Glu
2630                2635                2640

Phe Thr Leu Leu Asn Thr Phe His Val His Ser Phe Thr Ile Asp
2645                2650                2655

Leu Leu Glu Ile Lys Ala Lys Ile Ile Arg Thr Ile Asp Gln Ile
2660                2665                2670

Leu Ser Ser Glu Leu Gln Trp Pro Leu Pro Glu Met Tyr Leu Arg
2675                2680                2685

Asp Leu Asp Val Val Asn Ile Pro Leu Ala Arg Leu Thr Leu Pro
2690                2695                2700

Asp Phe His Val Pro Glu Ile Thr Ile Pro Glu Phe Thr Ile Pro
2705                2710                2715

Asn Val Asn Leu Lys Asp Leu His Val Pro Asp Leu His Ile Pro
2720                2725                2730

Glu Phe Gln Leu Pro His Leu Ser His Thr Ile Glu Ile Pro Ala
2735                2740                2745

Phe Gly Lys Leu His Ser Ile Leu Lys Ile Gln Ser Pro Leu Phe
2750                2755                2760

Ile Leu Asp Ala Asn Ala Asn Ile Gln Asn Val Thr Thr Ser Gly
2765                2770                2775

Asn Lys Ala Glu Ile Val Ala Ser Val Thr Ala Lys Gly Glu Ser
2780                2785                2790

Gln Phe Glu Ala Leu Asn Phe Asp Phe Gln Ala Gln Ala Gln Phe
2795                2800                2805

Leu Glu Leu Asn Pro His Pro Pro Val Leu Lys Glu Ser Met Asn
2810                2815                2820

Phe Ser Ser Lys His Val Arg Met Glu His Glu Gly Glu Ile Val
2825                2830                2835

Phe Asp Gly Lys Ala Ile Glu Gly Lys Ser Asp Thr Val Ala Ser
2840                2845                2850

Leu His Thr Glu Lys Asn Glu Val Glu Phe Asn Asn Gly Met Thr
2855                2860                2865

Val Lys Val Asn Asn Gln Leu Thr Leu Asp Ser His Thr Lys Tyr
2870                2875                2880

Phe His Lys Leu Ser Val Pro Arg Leu Asp Phe Ser Ser Lys Ala
2885                2890                2895

Ser Leu Asn Asn Glu Ile Lys Thr Leu Leu Glu Ala Gly His Val
2900                2905                2910

Ala Leu Thr Ser Ser Gly Thr Gly Ser Trp Asn Trp Ala Cys Pro
2915                2920                2925

Asn Phe Ser Asp Glu Gly Ile His Ser Ser Gln Ile Ser Phe Thr
2930                2935                2940

Val Asp Gly Pro Ile Ala Phe Val Gly Leu Ser Asn Asn Ile Asn
2945                2950                2955

Gly Lys His Leu Arg Val Ile Gln Lys Leu Thr Tyr Glu Ser Gly
2960                2965                2970
```

-continued

Phe Leu Asn Tyr Ser Lys Phe Glu Val Glu Ser Lys Val Glu Ser
2975                2980                2985

Gln His Val Gly Ser Ser Ile Leu Thr Ala Asn Gly Arg Ala Leu
2990                2995                3000

Leu Lys Asp Ala Lys Ala Glu Met Thr Gly Glu His Asn Ala Asn
3005                3010                3015

Leu Asn Gly Lys Val Ile Gly Thr Leu Lys Asn Ser Leu Phe Phe
3020                3025                3030

Ser Ala Gln Pro Phe Glu Ile Thr Ala Ser Thr Asn Asn Glu Gly
3035                3040                3045

Asn Leu Lys Val Gly Phe Pro Leu Lys Leu Thr Gly Lys Ile Asp
3050                3055                3060

Phe Leu Asn Asn Tyr Ala Leu Phe Leu Ser Pro Arg Ala Gln Gln
3065                3070                3075

Ala Ser Trp Gln Ala Ser Thr Arg Phe Asn Gln Tyr Lys Tyr Asn
3080                3085                3090

Gln Asn Phe Ser Ala Ile Asn Asn Glu His Asn Ile Glu Ala Ser
3095                3100                3105

Ile Gly Met Asn Gly Asp Ala Asn Leu Asp Phe Leu Asn Ile Pro
3110                3115                3120

Leu Thr Ile Pro Glu Ile Asn Leu Pro Tyr Thr Glu Phe Lys Thr
3125                3130                3135

Pro Leu Leu Lys Asp Phe Ser Ile Trp Glu Glu Thr Gly Leu Lys
3140                3145                3150

Glu Phe Leu Lys Thr Thr Lys Gln Ser Phe Asp Leu Ser Val Lys
3155                3160                3165

Ala Gln Tyr Lys Lys Asn Ser Asp Lys His Ser Ile Val Val Pro
3170                3175                3180

Leu Gly Met Phe Tyr Glu Phe Ile Leu Asn Asn Val Asn Ser Trp
3185                3190                3195

Asp Arg Lys Phe Glu Lys Val Arg Asn Asn Ala Leu His Phe Leu
3200                3205                3210

Thr Thr Ser Tyr Asn Glu Ala Lys Ile Lys Val Asp Lys Tyr Lys
3215                3220                3225

Thr Glu Asn Ser Leu Asn Gln Pro Ser Gly Thr Phe Gln Asn His
3230                3235                3240

Gly Tyr Thr Ile Pro Val Val Asn Ile Glu Val Ser Pro Phe Ala
3245                3250                3255

Val Glu Thr Leu Ala Ser Ser His Val Ile Pro Thr Ala Ile Ser
3260                3265                3270

Thr Pro Ser Val Thr Ile Pro Gly Pro Asn Ile Met Val Pro Ser
3275                3280                3285

Tyr Lys Leu Val Leu Pro Pro Leu Glu Leu Pro Val Phe His Gly
3290                3295                3300

Pro Gly Asn Leu Phe Lys Phe Phe Leu Pro Asp Phe Lys Gly Phe
3305                3310                3315

Asn Thr Ile Asp Asn Ile Tyr Ile Pro Ala Met Gly Asn Phe Thr
3320                3325                3330

Tyr Asp Phe Ser Phe Lys Ser Ser Val Ile Thr Leu Asn Thr Asn
3335                3340                3345

Ala Gly Leu Tyr Asn Gln Ser Asp Ile Val Ala His Phe Leu Ser
3350                3355                3360

```
Ser Ser Ser Phe Val Thr Asp Ala Leu Gln Tyr Lys Leu Glu Gly
    3365             3370                 3375

Thr Ser Arg Leu Met Arg Lys Arg Gly Leu Lys Leu Ala Thr Ala
    3380             3385                 3390

Val Ser Leu Thr Asn Lys Phe Val Lys Gly Ser His Asp Ser Thr
    3395             3400                 3405

Ile Ser Leu Thr Lys Lys Asn Met Glu Ala Ser Val Arg Thr Thr
    3410             3415                 3420

Ala Asn Leu His Ala Pro Ile Phe Ser Met Asn Phe Lys Gln Glu
    3425             3430                 3435

Leu Asn Gly Asn Thr Lys Ser Lys Pro Thr Val Ser Ser Ser Ile
    3440             3445                 3450

Glu Leu Asn Tyr Asp Phe Asn Ser Ser Lys Leu His Ser Thr Ala
    3455             3460                 3465

Thr Gly Gly Ile Asp His Lys Phe Ser Leu Glu Ser Leu Thr Ser
    3470             3475                 3480

Tyr Phe Ser Ile Glu Ser Phe Thr Lys Gly Asn Ile Lys Ser Ser
    3485             3490                 3495

Phe Leu Ser Gln Glu Tyr Ser Gly Ser Val Ala Asn Glu Ala Asn
    3500             3505                 3510

Val Tyr Leu Asn Ser Lys Gly Thr Arg Ser Ser Val Arg Leu Gln
    3515             3520                 3525

Gly Ala Ser Lys Val Asp Gly Ile Trp Asn Val Glu Val Gly Glu
    3530             3535                 3540

Asn Phe Ala Gly Glu Ala Thr Leu Gln Arg Ile Tyr Thr Thr Trp
    3545             3550                 3555

Glu His Asn Met Lys Asn His Leu Gln Val Tyr Ser Tyr Phe Phe
    3560             3565                 3570

Thr Lys Gly Lys Gln Thr Cys Arg Ala Thr Leu Glu Leu Ser Pro
    3575             3580                 3585

Trp Thr Met Ser Thr Leu Leu Gln Val His Val Ser Gln Leu Ser
    3590             3595                 3600

Ser Leu Leu Asp Leu His His Phe Asp Gln Glu Val Ile Leu Lys
    3605             3610                 3615

Ala Asn Thr Lys Asn Gln Lys Ile Ser Trp Lys Gly Gly Val Gln
    3620             3625                 3630

Val Glu Ser Arg Val Leu Gln His Asn Ala Gln Phe Ser Asn Asp
    3635             3640                 3645

Gln Glu Glu Ile Arg Leu Asp Leu Ala Gly Ser Leu Asp Gly Gln
    3650             3655                 3660

Leu Trp Asp Leu Glu Ala Ile Phe Leu Pro Val Tyr Gly Lys Ser
    3665             3670                 3675

Leu Gln Glu Leu Leu Gln Met Asp Gly Lys Arg Gln Tyr Leu Gln
    3680             3685                 3690

Ala Ser Thr Ser Leu Leu Tyr Thr Lys Asn Pro Asn Gly Tyr Leu
    3695             3700                 3705

Leu Ser Leu Pro Val Gln Glu Leu Ala Asp Arg Phe Ile Ile Pro
    3710             3715                 3720

Gly Ile Lys Leu Asn Asp Phe Ser Gly Val Lys Ile Tyr Lys Lys
    3725             3730                 3735

Leu Ser Thr Ser Pro Phe Ala Leu Asn Leu Thr Met Leu Pro Lys
    3740             3745                 3750
```

-continued

Val Lys Phe Pro Gly Ile Asp Leu Leu Thr Gln Tyr Ser Thr Pro
3755              3760              3765

Glu Gly Ser Ser Val Pro Ile Phe Glu Ala Thr Ile Pro Glu Ile
3770              3775              3780

His Leu Thr Val Ser Gln Phe Thr Leu Pro Lys Ser Leu Pro Val
3785              3790              3795

Gly Asn Thr Val Phe Asp Leu Asn Lys Leu Ala Asn Met Ile Ala
3800              3805              3810

Asp Val Asp Leu Pro Ser Val Thr Leu Pro Glu Gln Thr Ile Val
3815              3820              3825

Ile Pro Pro Leu Glu Phe Ser Val Pro Ala Gly Ile Phe Ile Pro
3830              3835              3840

Phe Phe Gly Glu Leu Thr Ala Arg Ala Gly Met Ala Ser Pro Leu
3845              3850              3855

Tyr Asn Val Thr Trp Ser Ala Gly Trp Lys Thr Lys Ala Asp His
3860              3865              3870

Val Glu Thr Phe Leu Asp Ser Met Cys Thr Ser Thr Leu Gln Phe
3875              3880              3885

Leu Glu Tyr Ala Leu Lys Val Val Glu Thr His Lys Ile Glu Glu
3890              3895              3900

Asp Leu Leu Thr Tyr Asn Ile Lys Gly Thr Leu Gln His Cys Asp
3905              3910              3915

Phe Asn Val Glu Tyr Asn Glu Asp Gly Leu Phe Lys Gly Leu Trp
3920              3925              3930

Asp Trp Gln Gly Glu Ala His Leu Asp Ile Thr Ser Pro Ala Leu
3935              3940              3945

Thr Asp Phe His Leu Tyr Tyr Lys Glu Asp Lys Thr Ser Leu Ser
3950              3955              3960

Ala Ser Ala Ala Ser Ser Thr Ile Gly Thr Val Gly Leu Asp Ser
3965              3970              3975

Ser Thr Asp Asp Gln Ser Val Glu Leu Asn Val Tyr Phe His Pro
3980              3985              3990

Gln Ser Pro Pro Glu Lys Lys Leu Ser Ile Phe Lys Thr Glu Trp
3995              4000              4005

Arg Tyr Lys Glu Ser Asp Gly Glu Arg Tyr Ile Lys Ile Asn Trp
4010              4015              4020

Glu Glu Glu Ala Ala Ser Arg Leu Leu Gly Ser Leu Lys Ser Asn
4025              4030              4035

Val Pro Lys Ala Ser Lys Ala Ile Tyr Asp Tyr Ala Asn Lys Tyr
4040              4045              4050

His Leu Glu Tyr Val Ser Ser Glu Leu Arg Lys Ser Leu Gln Val
4055              4060              4065

Asn Ala Glu His Ala Arg Arg Met Val Asp Glu Met Asn Met Ser
4070              4075              4080

Phe Gln Arg Val Ala Arg Asp Thr Tyr Gln Asn Leu Tyr Glu Glu
4085              4090              4095

Met Leu Ala Gln Lys Ser Leu Ser Ile Pro Glu Asn Leu Lys Lys
4100              4105              4110

Arg Val Leu Asp Ser Ile Val His Val Thr Gln Lys Tyr His Met
4115              4120              4125

Ala Val Met Trp Leu Met Asp Ser Phe Ile His Phe Leu Lys Phe
4130              4135              4140

```
Asn Arg Val Gln Phe Pro Gly Tyr Ala Gly Thr Tyr Thr Val Asp
4145                4150                4155

Glu Leu Tyr Thr Ile Val Met Lys Glu Thr Lys Ser Leu Ser
4160                4165                4170

Gln Leu Phe Asn Gly Leu Gly Asn Leu Leu Ser Tyr Val Gln Asn
4175                4180                4185

Gln Val Glu Lys Ser Arg Leu Ile Asn Asp Ile Thr Phe Lys Cys
4190                4195                4200

Pro Phe Phe Ser Lys Pro Cys Lys Leu Lys Asp Leu Ile Leu Ile
4205                4210                4215

Phe Arg Glu Glu Leu Asn Ile Leu Ser Asn Ile Gly Gln Gln Asp
4220                4225                4230

Ile Lys Phe Thr Thr Ile Leu Ser Ser Leu Gln Gly Phe Leu Glu
4235                4240                4245

Arg Val Leu Asp Ile Ile Glu Glu Gln Ile Lys Cys Leu Lys Asp
4250                4255                4260

Asn Glu Ser Thr Cys Val Ala Asp His Ile Asn Met Val Phe Lys
4265                4270                4275

Ile Gln Val Pro Tyr Ala Phe Lys Ser Leu Arg Glu Asp Ile Tyr
4280                4285                4290

Phe Val Leu Gly Glu Phe Asn Asp Phe Leu Gln Ser Ile Leu Gln
4295                4300                4305

Glu Gly Ser Tyr Lys Leu Gln Gln Val His Gln Tyr Met Lys Ala
4310                4315                4320

Leu Arg Glu Glu Tyr Phe Asp Pro Ser Met Val Gly Trp Thr Val
4325                4330                4335

Lys Tyr Tyr Glu Ile Glu Glu Asn Met Val Glu Leu Ile Lys Thr
4340                4345                4350

Leu Leu Val Ser Phe Arg Asp Val Tyr Ser Glu Tyr Ser Val Thr
4355                4360                4365

Ala Ala Asp Phe Ala Ser Lys Met Ser Thr Gln Val Glu Gln Phe
4370                4375                4380

Val Ser Arg Asp Ile Arg Glu Tyr Leu Ser Met Leu Thr Asp Ile
4385                4390                4395

Asn Gly Lys Trp Met Glu Lys Ile Ala Glu Leu Ser Ile Val Ala
4400                4405                4410

Lys Glu Thr Met Lys Ser Trp Val Thr Ala Val Ala Lys Ile Met
4415                4420                4425

Ser Asp Tyr Pro Gln Gln Phe His Ser Asn Leu Gln Asp Phe Ser
4430                4435                4440

Asp Gln Leu Ser Ser Tyr Tyr Glu Lys Phe Val Gly Glu Ser Thr
4445                4450                4455

Arg Leu Ile Asp Leu Ser Ile Gln Asn Tyr His Val Phe Leu Arg
4460                4465                4470

Tyr Ile Thr Glu Leu Leu Arg Lys Leu Gln Val Ala Thr Ala Asn
4475                4480                4485

Asn Val Ser Pro Tyr Ile Lys Leu Ala Gln Gly Glu Leu Met Ile
4490                4495                4500

Thr Phe
4505
```

```
<210> SEQ ID NO 29
<211> LENGTH: 13931
<212> TYPE: DNA
<213> ORGANISM: Mus musculus

<400> SEQUENCE: 29
tacctgcctg agctccgcct ccgaagaccc tgtagagcaa gcagcagggg ctaggcccgt      60
ggccaggcca cagccaggaa gccaccccac catccatccg ccatgggccc acgaaagcct     120
gccctgcgga cgccgttact gctgctgttc ctgctactgt tcttggacac cagcgtctgg     180
gctcaagatg aagtcctgga aaacttaagc ttcagctgtc aaaagatgc aactcgattc      240 aagcacctcc gaaagtacgt gtacaactat gaagctgaaa gttccagcgg tgtccagggc     300
acagctgact ccagaagcgc caccaagatc aactgtaagg tagagctgga ggtcccccaa     360
atctgtggtt tcatcatgag gaccaaccag tgtaccctta agaggtgta tggcttcaac      420 cctgagggca aggccttgat gaagaaaacc aagaactctg aagagtttgc agctgccatg     480
tccaggtacg aactcaagct ggccattcct gaagggaaac aaattgttct ttaccctgac     540
aaggatgaac ctaaatatat cctgaacatc aagaggggca tcatctctgc tcttctggtt     600
cccccagaga cagaagagga ccaacaagag ttgttcctgg ataccgtgta tggaaactgc     660
tcaactcagg ttaccgtgaa ttcaagaaag gaaccgtac caacagaaat gtccacagag      720
agaaacctgc agcaatgtga cggcttccag cccatcagta agtgtcag ccctctcgct       780 ctcatcaaag gcctggtcca ccccttgtca actcttatca gcagcagcca aacttgccag     840
tacacccctg gatcctaagag gaagcatgtg tctgaagctg tctgtgatga gcagcatctt     900
ttcctgcctt tctcctacaa gaataagtat gggatcatga cacgtgttac acagaaactg     960
agtcttgaag acacacctaa gatcaacagt cgcttcttca gtgaaggtac caaccggatg    1020
ggtctggcct ttgagagcac caagtccacg tcatccccaa agcaggctga tgctgttttg    1080 aagaccttc aagaactgaa aaaattgtcc atctcagagc agaatgctca gagagcaaat     1140
ctcttcaata aactggttac tgagctgaga ggcctcactg gtgaagcaat cacatccctc    1200
ttgccacagc tgattgaagt gtccagcccc atcactttac aagccttggt tcagtgtgga    1260
cagccacagt gctatactca catcctccag tggctgaaaa ctgagaaggc tcacccctc    1320 ctggttgaca ttgtcaccta cctgatggct ctgatcccaa atccctcaac acagaggctg    1380
caggaaatct ttaatactgc caaggagcag cagagccgag ccactctgta tgcactgagc    1440
cacgcagtta acagctattt tgatgtggac cattcaagga gcccagttct gcaggatatc    1500
gctggttacc tgttgaaaca gatcgacaat gaatgcacgg gcaatgaaga ccacaccttc    1560
ttgattctga gggtcattgg aaatatggga agaaccatgg aacaagtaat gccagccctc    1620
aagtcctcag tcctgagctg tgtacgaagt acaaaaccat ctctgctgat tcagaaagct    1680
gctctccagg ccctgaggaa gatggaactg gaagatgagg tccggacgat cctttttgat    1740
acatttgtaa atggtgtcgc tcccgtggag aagagactgg ctgcctatct cttgctgatg    1800 aagaacccttt cctcatcaga tattaacaaa attgcccaac ttctccaatg ggaacagagt    1860
gagcaggtga gaacttcgt ggcatctcac attgccaaca tcttgaactc ggaagaactg    1920
tatgtccaag atctgaaagt tttgatcaaa aatgctctgg agaattctca atttccaacg    1980
atcatggact tcagaaaatt ttcccgaaac tatcagattt ccaaatctgc ttctctccca    2040
atgttcgacc cagtctcagt caaaatgaa gggaatctta tatttgatcc aagcagttat    2100
cttcccagag aaagcttgct gaaaacaacc ctcacagtct ttggacttgc ttcacttgat    2160
```

```
ctctttgaga ttggtttaga aggaaaaggg tttgagccaa cactagaagc tcttttggt    2220
aagcaaggat tcttcccaga cagtgtcaac aaggctttgt attgggtcaa tggccgagtt    2280
ccagatggtg tctccaaggt cttggtggac cactttggct atactacaga tggcaagcat    2340
gaacaggaca tggtgaatgg aatcatgccc attgtggaca agttgatcaa agatctgaaa    2400
tctaaagaaa ttcctgaagc cagggcctat ctccgcatcc taggaaaaga gctaagcttt    2460
gtcagactcc aagacctcca agtcctgggg aagctgttgc tgagtggtgc acaaactttg    2520
cagggaatcc cccagatggt tgtacaggcc atcagagaag ggtcaaagaa tgacttgttt    2580
ctccactaca tcttcatgga caatgccttt gagctcccca ctggagcagg gttacagctg    2640
caagtgtcct cgtctggagt cttcacccc gggatcaagg ctggtgtaag actggaatta    2700
gccaacatac aggcagagct agtggcaaag ccctctgtgt ccttggagtt tgtgacaaat    2760
atgggcatca tcatcccaga cttcgctaag agcagtgtcc agatgaacac caacttcttc    2820
cacgagtcag gcctggaggc gcgagtggcc ctgaaggctg ggcagctgaa ggtcatcatt    2880
ccttctccaa agaggccagt caagctgttc agtggcagca acactgca tctggtctct    2940
accaccaaaa cagaagtgat cccacctctg gttgagaaca ggcagtcctg gtcaacttgc    3000
aagcctctct tcactggaat gaactactgt accacaggag cttactccaa cgccagctcc    3060
acggagtctg cctcttacta cccactgaca ggggacacaa ggtatgagct ggagctgagg    3120
cccacgggag aagtggagca gtattctgcc actgcaacct atgaactcct aaaagaggac    3180
aagtctttgg ttgacacatt gaagttccta gttcaagcag aaggagtgca gcagtctgaa    3240
gctactgtac tgttcaaata taatcggaga agcaggacct tatctagtga agtcctaatt    3300
ccagggtttg atgtcaactt cgggacaata ctaagagtta tgatgaatc tgctaaggac    3360
aaaaacactt acaaactcat cctggacatt cagaacaaga aaatcactga ggtctctctc    3420
gtgggccact tgagttatga taaaaaggga gatggcaaga tcaaggtgt tgtttccata    3480
ccacgtttgc aagcagaagc caggagtgag gtccacaccc actggtcctc caccaaactg    3540
ctcttccaaa tggactcatc tgctacagct tacggctcaa caatttccaa gagagtgaca    3600
tggcgttacg ataatgagat aatagaattt gattggaaca cgggaaccaa tgtggatacc    3660
aaaaaagtgg cctccaattt ccctgtggat cttttcccatt atcctagaat gttgcatgag    3720
tatgccaatg gtctcctgga tcacagagtc cctcaaacag atgtgacttt tcgggacatg    3780
ggttccaaat taattgttgc aacaaacaca tggcttcaga tggcaaccag gggtcttcct    3840
taccccaaa ctctacagga tcacctcaat agcctctcag agttgaacct cctgaaaatg    3900
ggactgtctg acttccatat tccagacaac ctcttcctaa agactgatgg cagagtcaaa    3960
tacacaatga acaggaacaa aataaacatt gacatccctt tgcctttggg tggcaagtct    4020
tcaaaagacc tcaagatgcc agagagtgtg aggacaccag ccctcaactt caagtctgtg    4080
ggattccatc tgccatctcg agaggtccag gtccccactt ttacaatccc caagacacat    4140
cagcttcaag tgcctctctt gggtgttcta gacctttcca caaatgtcta cagcaatttg    4200
tacaactggt cagcctccta cactggtggc aacaccagca gagaccactt cagccttcag    4260
gctcagtacc gcatgaagac tgactctgtg gttgacctgt tttcctacag tgtgcaagga    4320
tctggagaaa caacatatga cagcaagaac acatttacat tgtcctgtga tggatctcta    4380
caccataaat ttctagactc aaaattcaaa gtcagccacg tagaaaaatt tggaaacagc    4440
ccagtctcaa aaggtttact aacatttgaa acatctagtg ccttgggacc acagatgtct    4500
gctactgttc acctagactc aaaaaagaaa caacatctat acgtcaaaga tatcaaggtt    4560
```

```
gatggacagt tcagagcttc ttcattttat gctcaaggca aatatggcct gtcttgtgag    4620
agagatgtta caactggcca gctgagcggc gaatccaaca tgagatttaa ctccacctac    4680
ttccagggca ccaaccagat cgtgggaatg taccaggatg gagccctgtc catcacctcc    4740
acttctgacc tgcaagatgg catattcaag aacacagctt ccttgaaata tgaaaactat    4800
gagctgactc tgaaatctga tagcagtggg cagtatgaga acttcgctgc ttccaacaag    4860
ctggatgtga ccttctctac gcaaagtgca ctgctgcgtt ctgaacacca ggccaattac    4920
aagtccctga ggcttgtcac ccttctttca ggatccctca cttcccaggg tgtagaatta    4980
aatgctgaca tcttgggcac agacaaaatt aatactggtg ctcacaaggc aacactaaag    5040
attgcacgtg atggactatc aaccagtgcg accaccaact tgaagtacag ccccctgctg    5100
ctggagaatg agttgaatgc agagcttggg ctctctgggg catccatgaa attatcaaca    5160
aacggccgct tcaaagaaca ccatgcaaaa ttcagtcttg atgggagagc tgccctcaca    5220
gaggtgtcac tggggagcat ttaccaggcc atgattctgg gtgcagacag caaaaacatc    5280
ttcaacttca aactcagccg agaagggctg aggctgtcca atgatttgat gggctcctat    5340
gctgagatga acttgacca cacacacagt ctgaacattg caggtctctc actggacttc    5400
ttctcaaaaa tggacaatat ttacagtgga gacaagttct ataagcagaa ttttaactta    5460
cagctacagc cctattcttt cataactact ttaagcaacg acctgagata tggtgctcta    5520
gatttgacca acaatggaag gtttcggctg agccactga agctgaatgt gggtggcaac    5580
tttaaaggaa cctatcaaaa taatgagctg aaacatatct ataccatatc ttatactgac    5640
ctggtagtag caagttacag agcagacact gtggctaagg ttcagggtgt cgaattcagc    5700
cataggctaa atgcagacat tgaaggactg acttcctctg ttgatgtcac taccagctac    5760
aattcagatc cactgcattt taacaatgtt ttccactttt ctctggcacc ttttaccttg    5820
ggcatcgaca cacatacaag tggtgatggg aaactgtcct tctggggaga acacactggg    5880
cagctatata gtaagtttct gttgaaagca gaacctctgg cacttattgt ctctcatgac    5940
tacaaaggat ccacaagcca cagtctcccg tacgagagca gcatcagcac ggctcttgaa    6000
cacacagtca gtgccttgct gacgccagct gagcagacaa gcacctggaa attcaagacc    6060
aaactgaatg acaaagtata cagccaggac tttgaagcct acaacactaa agacaaaatc    6120
ggtgttgagc ttagtggacg ggctgacctc tctgggctgt attctccaat taaactaccg    6180
tttttctaca gtgagcctgt caatgtcctt aatggcttag aggtaaatga tgctgttgac    6240
aagccccaag aattcacaat tattgctgtg gtgaagtacg ataagaacca ggatgttcac    6300
accatcaacc tcccattctt caaaagcctg ccagactatt tggagagaaa tcgaagagga    6360
atgataagtc tactgaagc catgcgaggg gaattgcaac gcctcagtgt tgatcagttt    6420
gtgaggaaat acagagcggc cctgagcaga cttcctcagc agattcatca ttatctgaat    6480
gcatctgact gggagagaca agtagctggt gccaaggaaa aaataacttc tttcatggaa    6540
aattatagaa ttacagataa tgatgtacta attgccatag atagtgccaa atcaacttc    6600 aatgaaaaac tctctcaact tgagacatac gcgatacaat ttgatcagta tattaaagat    6660
aattatgatc cacatgactt aaaaagaact attgctgaga ttattgatcg aatcattgaa    6720
aagttaaaaa ttcttgatga acagtatcat atccgtgtaa atctagcaaa atcaatccat    6780
aatctctatt tatttgttga aaacgttgat cttaaccaag tcagtagtag taacacctct    6840
tggatccaaa atgtggattc caattatcaa gtcagaatcc aaattcaaga aaaactacag    6900
cagctcagga cacaaattca gaatatagac attcagcagc ttgctgcaga ggtaaaacga    6960
```

```
cagatggacg ctattgatgt cacaatgcat ttagatcaat tgagaactgc aattctattc    7020
caaagaataa gtgacattat tgaccgtgtc aaatactttg ttatgaatct tattgaagat    7080
tttaaagtaa ctgagaaaat caatactttt agagttatag tccgtgagct aattgagaaa    7140
tatgaagtag accaacacat ccaggtttta atggataaat cagtagagtt ggcccacaga    7200
tatagcctga gcgagcctct tcagaaactc agtaatgtgc tacagcgaat tgagataaaa    7260
gattactatg agaaattggt tgggtttatt gatgatactg ttgagtggct taaagcattg    7320
tctttcaaaa ataccattga agaactaaat agattgactg acatgttggt gaagaagttg    7380
aaagcatttg attatcacca gtttgtagac aaaaccaaca gcaaaatccg tgagatgact    7440
cagagaatca atgctgaaat ccaagctctc aaacttccac aaaaaatgga agcattaaaa    7500
ctgttggtag aagacttcaa aaccacagtc tccaattccc tggaaagact caaggacacc    7560
aaagtaactg tggtcattga ttggctgcag gatattttga ctcaaatgaa agaccatttc    7620
caagatactc tggaagatgt aagagaccga atttatcaaa tggacattca gagggaactg    7680
gagcacttct tgtctctggt aaaccaagtt tacagtacac tggtcaccta tatgtctgac    7740
tggtggactc tgactgctaa aaacataaca gactttgcag agcaatattc catccaaaac    7800
tgggctgaga gtataaaagt actggtggaa caaggattca tagttcctga aatgcaaaca    7860
tttctgtgga ccatgcctgc ttttgaggtc agtctccgtg ctctccaaga aggtaacttt    7920
cagacccctg tctttatagt ccccttgaca gatttgagga ttccatcaat tcggataaac    7980
tttaaaatgt taaagaatat aaaaatccca ttgagatttt ccactccaga attcactctt    8040
ctcaacacct tccatgtcca ttcctttaca attgacttgc tggaaataaa agcaaagatc    8100
attagaacta tcgaccaaat tttgagcagt gagctacagt ggcctcttcc agaaatgtat    8160
ttgagagacc tggatgtagt gaacattcct cttgcaagac tgactctgcc agacttccat    8220
gtaccagaaa tcacaattcc agaattcaca atcccaaatg tcaatctcaa agatttacac    8280
gttcctgatc ttcacatacc agaattccaa cttcctcacc tctcacatac aattgaaata    8340
cctgcttttg gcaaactgca tagcatcctt aagatccaat ctcctctctt tatattagat    8400
gctaatgcca acatacagaa tgtaacaact tcagggaaca aagcagagat tgtggcttct    8460
gtcactgcta aaggagagtc ccaatttgaa gctctcaatt ttgatttttca agcacaagct    8520
```

```
ttcaatcagt acaaatacaa tcaaaacttt tctgctataa acaatgaaca caacatagaa    9420
gccagtatag gaatgaatgg agatgccaac ctggatttct taaacatacc tttaacaatt    9480
cctgaaatta acttgcctta cacggagttc aaaactccct tactgaagga tttctccata    9540
tgggaagaaa caggcttgaa agaattttg aagacaacaa agcaatcatt tgatttgagt     9600
gtaaaggctc aatataaaaa gaacagtgac aagcattcca ttgttgtccc tctgggtatg    9660
tttatgaat ttattctcaa caatgtcaat tcgtgggaca gaaaatttga gaaagtcaga     9720
aacaatgctt tacattttct taccacctcc tataatgaag caaaaattaa ggttgataag    9780
tacaaaactg aaaattccct taatcagccc tctgggacct tcaaaatca tggctacact     9840
atcccagttg tcaacattga agtatctcca tttgctgtag agacactggc ttccagccat    9900
gtgatcccca cagcaataag caccccaagt gtcacaatcc ctggtcctaa catcatggtg    9960
ccttcataca agttagtgct gccacccctg gagttgccag ttttccatgg tcctgggaat   10020
ctattcaagt ttttcctccc agatttcaag ggattcaaca ctattgacaa tatttatatt   10080
ccagccatgg gcaactttac ctatgacttt tcttttaaat caagtgtcat cacactgaat   10140
accaatgctg gactttataa ccaatcagat atcgttgccc atttcctttc ttcctcttca   10200
tttgtcactg acgccctgca gtacaaatta gagggaacat cacgtctgat gcgaaaaagg   10260
ggattgaaac tagccacagc tgtctctcta actaacaaat ttgtaaaggg cagtcatgac   10320
agcaccatta gttaaccaa gaaaaacatg gaagcatcag tgagaacaac tgccaacctc    10380
catgctccca tattctcaat gaacttcaag caggaactta atggaaatac caagtcaaaa   10440
cccactgttt catcatccat tgaactaaac tatgacttca attcctcaaa gctgcactct   10500
actgcaacag gaggcattga tcacaagttc agcttagaaa gtctcacttc ctacttttcc   10560
attgagtcat tcaccaaagg aaatatcaag agttccttcc tttctcagga atattcagga   10620
agtgttgcca atgaagccaa tgtatatctg aattccaagg gtactcggtc ttcagtgagg   10680
ctacaaggag cttccaaagt tgatggtatc tggaacgttg aagtaggaga aaattttgct   10740
ggagaagcca ccctccaacg catctacacc acatgggagc acaatatgaa aaaccatttg   10800
caggtatata gctacttctt cacaaaagga aagcaaacat gcagagctac tttggagctc   10860
tccccatgga ccatgtcaac cttgctacag gttcatgtga gtcaactcag ttccctcctt   10920
gacctccatc actttgacca ggaagtgatc ctaaaagcta acactaagaa ccagaagatc   10980
agctggaaag gtgggtccca ggttgaatca cgggttcttc agcacaatgc acagttctcc   11040
aatgaccaag aagaaatacg gcttgacctt gcaggatcct tagacggaca gctgtgggac   11100
cttgaagcta tcttttttacc agtatatggc aagagcttgc aggaactcct acaaatggat   11160
ggaaagcgac agtatcttca agcttcaact tctcttctat ataccaaaaa ccctaatggc   11220
tatctcctct cactcccgt gcaagaactg gctgatagat ttattatacc agggataaaa    11280
ctaaatgact tcagtggagt aaaaatctat aagaagttaa gtacttcacc attgccctc    11340
aacctaacaa tgctccccaa agtaaaattc cctgggattg atctgttaac acagtactct   11400
acaccagagg gctcctctgt ccctattttt gaggcaacta tacctgaaat tcatttaact   11460
gtatcccagt ttacacttcc aaagagcctt ccagttggca acacagtctt tgatctgaat   11520
aagttggcca acatgattgc cgatgttgac ctgccagtg tcaccctgcc tgagcagact    11580
attgtaatcc caccccttgga gttctctgta acctgctggga ttttattcc tttctttgga  11640
gaactgactg cacgtgctgg gatggcttct cccctgtata atgtcacttg gagcgctggt   11700
```

```
tggaaaacca aagcagatca tgttgaaacg ttcctagatt ccatgtgcac ttcaaccttg    11760
cagtttctgg agtatgcttt aaaagttgta gaaacacaca aaattgaaga agatctgtta    11820
acctataata tcaaaggaac acttcaacac tgtgacttca atgtggagta taatgaagat    11880
ggtctattta aaggactttg ggactggcag ggagaggctc acctggacat caccagccca    11940
gcactgactg actttcatct gtactacaaa gaagacaaga caagtctgtc tgcctcagca    12000
gcctcctcga ccatcggcac tgtgggtctg gattcgagca cagatgacca gagtgtggag    12060
ctgaatgtct acttccaccc acagtcccct ccagagaaga aactcagcat attcaaaact    12120
gagtggaggt acaaggagtc tgatggtgaa aggtacatca aaattaattg ggaagaagag    12180
gcagcttcca gattgctagg ctccctaaaa agcaatgtgc ccaaggcttc taaggctatt    12240
tatgattatg ccaataagta ccacctggaa tacgtttctt cagaactaag aaaaagtcta    12300
caggtcaatg ctgaacatgc cagaaggatg gttgatgaaa tgaacatgag tttccagaga    12360
gtagcccgtg atacctacca gaatctctat gaggagatgt tggctcagaa gagcctgagc    12420
atccctgaga atctcaagaa gagggtgtta gacagtatag tacatgttac tcagaagtac    12480
cacatggcag tcatgtggct gatggactca ttcattcatt ttctgaaatt caatagagtc    12540
cagttcccag ggtacgctgg aacatatact gtggacgaac tctacactat agtcatgaag    12600
gaaaccaaga agtcactgtc tcagctgttt aatgggttag gaaacctact ttcctacgtt    12660
caaaaccaag tagagaaatc aagattaatc aatgacataa catttaaatg tccttttttc    12720
tcaaaacctt gtaaactaaa agatctcata ttgattttca gggaggagtt aaacatttta    12780
tcaaacatag gccaacagga tatcaagttt acaacaatac taagtagtct tcagggcttt    12840
ttggagagag ttttagacat catagaagaa caaattaaat gcctaaagga caatgaatct    12900
acttgtgttg ctgaccatat caacatggtt ttcaaaatac aggtcccata tgcttttaaa    12960
tccctaagag aagacatata ctttgtcctc ggtgagttca atgactttct tcaatccata    13020
cttcaggagg ggtcctacaa gctacagcag gtccatcagt atatgaaggc ccttcgtgaa    13080
gagtattttg atccgagcat ggtttgggtgg acagtgaaat attatgaaat agaagaaaat    13140
atggttgagc tgatcaagac cctttttagtt tcctttaggg atgtctactc tgaatatagt    13200
gtgacagctg ctgatttttgc ttccaaaatg tcaactcaag ttgaacaatt tgtgtccagg    13260
gatatcagag agtatcttag catgcttact gatataaatg gaaagtggat ggaaaagatt    13320
gcagagcttt ctattgtggc aaaggaaaca atgaaaagct gggtcactgc cgtggccaaa    13380
ataatgtctg attaccccca gcagttccac tccaatctgc aggattttttc agaccaactc    13440 tctagctact atgaaaaatt tgttggtgag tccacaagat tgattgacct gtccattcaa    13500
aactaccacg tgtttctcag atacatcacc gagttactga gaaagctgca ggtggccaca    13560
gccaataatg tgagccccta tataaagctt gctcaaggag agctgatgat caccttctga    13620
ttcatctact aacaaattca aattaaacct tcacatagta ggagactttg tagactacta    13680
taaagaccat cctgagccag acctgcagtc aacagcaaga gcaagaagca cataggaact    13740
atacctgcaa ccaagctggc ataagaacca agaccttcaa agcagcctga actcaagatg    13800
acatatttta caagttagag taaagtcaag agctgagttg ttttgtccaa ctcaggatgg    13860
agggagggag ggaagggaa ataaataaat acttccttat tgtgcagcaa aaaaaaaaa    13920 aaaaaaaaaa a                                                        13931
```

ISOLATED POLYPEPTIDES OF CD44 AND USES THEREOF

RELATED APPLICATIONS

This application is a National Phase of PCT Patent Application No. PCT/IL2015/050732 having International filing date of Jul. 15, 2015, which claims the benefit of priority under 35 USC § 119(e) of U.S. Provisional Patent Application No. 62/024,719 filed on Jul. 15, 2014. The contents of the above applications are all incorporated by reference as if fully set forth herein in their entirety.

SEQUENCE LISTING STATEMENT

The ASCII file, entitled 68204SequenceListing.txt, created on Jan. 9, 2017, comprising 159,396 bytes, submitted concurrently with the filing of this application is incorporated herein by reference.

FIELD AND BACKGROUND OF THE INVENTION

The present invention, in some embodiments thereof, relates to an isolated polypeptide of CD44 and, more particularly, but not exclusively, to an isolated polypeptide of CD44vRA and its use in the treatment of inflammatory disease.

CD44 is a cell surface adhesion molecule involved in multiple cellular functions, including cell-cell and cell-matrix interactions, cell migration, programmed cell death (apoptosis), or, conversely, cell survival and proliferation.

CD44 is the major cell surface receptor for hyaluronic acid (HA) but it has also been shown to bind proteins such as collagens, fibronectin, fibrinogen, laminin, mucosal vascular addressin and osteopontin. CD44 is essential for recruitment of circulating lymphocytes to the site of inflammation and marked accumulation of CD44, and sometimes hyaluronic acid, is detected in areas of intensive cell migration and cell proliferation, as in wound healing, tissue remodeling, inflammation, morphogenesis and carcinogenesis.

The genomic sequence of mouse and human CD44 includes 5 constant exons at the 5' terminus, and 5 constant exons at the 3' end. The mouse CD44 gene includes 10 variant exons in the middle of the molecule, designated $V_1$-$V_{10}$, resulting in a total of 20 exons. The human CD44 gene comprises only 9 of these 10 variant exons ($V_2$-$V_{10}$) thus comprising a total of 19 exons. Differential $V_2$-$V_{10}$ alternative splicing generates many isoforms of CD44 that express various combinations of variant exons (designated exon Vx, x=1-10), which are inserted in the membrane proximal domain and constitute the variable region of the molecule. These molecules are designated CD44 variants (CD44v). A few dozens isoforms of CD44 are known to date.

CD44s, which does not contain any variant exon, is the most ubiquitous form and is expressed by most cell types [Ponta, H., et al. Nat Rev Mol Cell Biol. 2003 January; 4(1):33-45]. CD44 variant proteins, in which one or more of the 10 variant exons are included, are mostly reported in association with cancer, and autoimmune diseases such as rheumatoid arthritis and multiple sclerosis [see e.g. Naor et al. Adv. Cancer Res., 71, 241-319, 1997; and Naor et al. Critical Reviews in Clinical Laboratory Sciences. 39, 527-579, 2002].

Joint inflammatory cells of patients with rheumatoid arthritis (RA) display a sequence of alternatively spliced CD44 variant designated CD44vRA. Human CD44vRA contains the same sequence as that of keratinocytes CD44v3-v10 isoform with an addition of extra alanine in the splicing junction between variant exon 4 and variant exon 5, which does not interfere with the reading frame. Mice with collagen-induced arthritis (CIA) contain at the same site a similar sequence that also includes the alanine. The CD44vRA sequence is expressed on joint inflammatory synovial cells of RA patients and Psoriatic Arthritis (PA) patients, but neither on keratinocytes nor peripheral blood leukocytes (PBLs) of healthy donors. Furthermore, while joint inflammatory cells of RA patients express CD44vRA, PBLs from the same patients and synovial fluid cells from osteoarthritis patients hardly express this variant, demonstrating the exclusivity of this isoform. (Nedvetzki et al., J Clin Invest 111:1211-1220, 2003; Golan et al., J Autoimm 28:99-113, 2007).

It has been reported that administration of anti-CD44 antibodies, CD44 proteins, peptides or derivatives can be used for treating various autoimmune diseases (e.g. Naor et al., Adv. Cancer Res., 71, 241-319, 1997; Naor et al., Critical Reviews in Clinical Laboratory Sciences. 39, 527-579, 2002; Turley E A, and Naor D. Front Biosci. 17:1775-1794, 2012). In addition, anti-CD44vRA monoclonal antibodies and CD44vRA-derived peptides were previously suggested (Golan et al., J Autoimm 28:99-113, 2007, International Application Publication Nos: WO2010/058396, WO 2005/007700; WO 2003/014160, WO 2000/075312; U.S. Pat. Nos. 7,534,605 and 8,193,311; and US Patent Application Publication No: US 20060019340).

SUMMARY OF THE INVENTION

According to an aspect of some embodiments of the present invention there is provided an isolated polypeptide consisting of an amino acid sequence selected form the group consisting of SEQ ID NOs: 1-3.

According to an aspect of some embodiments of the present invention there is provided an isolated end-capping modified polypeptide comprising an amino acid sequence selected from the group consisting of SEQ ID NO: 1-3, wherein the modified polypeptide comprises an anti-inflammatory activity.

According to some embodiments of the invention, the end-capping comprises an N terminus end-capping.

According to some embodiments of the invention, the N terminus end-capping comprises an Acetyl.

According to some embodiments of the invention, the end-capping comprises a C terminus end-capping.

According to some embodiments of the invention, the C terminus end-capping comprises an Amide.

According to some embodiments of the invention, the polypeptide consists of an amino acid sequence selected form the group consisting of SEQ ID NOs: 1-3.

According to some embodiments of the invention, the polypeptide is as set forth in SEQ ID NO: 1.

According to some embodiments of the invention, the end-capping modified polypeptide being selected form the group consisting to SEQ ID NOs: 4-6.

According to some embodiments of the invention there is provided a composition of matter comprising the isolated polypeptide and a non-proteinaceous moiety attached to the isolated polypeptide, wherein the isolated fusion polypeptide comprises an anti-inflammatory activity.

According to some embodiments of the invention there is provided an isolated fusion polypeptide comprising the isolate polypeptide having a C and/or N terminally attached amino acid sequence, wherein the C terminally amino acid sequence is a non-contiguous CD44vRA amino acid sequence with the isolated fusion polypeptide; and wherein the fusion polypeptide comprises an anti-inflammatory activity.

According to some embodiments of the invention, the attached is covalent attachment.

According to some embodiments of the invention, the anti-inflammatory activity is not dependent on vaccination or mucosal tolerance.

According to some embodiments of the invention, the isolated polypeptide or the composition of matter being capable of binding a protein selected from the group consisting of serum amyloid A, Transthyretin and apolipoprotein B.

According to some embodiments of the invention there is provided a pharmaceutical composition comprising as an active agent the isolated polypeptide or the composition of matter; and a pharmaceutically acceptable carrier or diluent.

According to some embodiments of the invention there is provided a method of treating an inflammatory disease in a subject in need thereof, the method comprising administering to the subject a therapeutically effective amount of the isolated polypeptide, the composition of matter or the pharmaceutical composition, thereby treating the inflammatory disease in the subject.

According to some embodiments of the invention there is provided a use of the isolated polypeptide, the composition of matter or the pharmaceutical composition, for the manufacture of a medicament for the treatment of an inflammatory disease.

According to some embodiments of the invention, the administering comprises oral administering.

According to some embodiments of the invention, the composition is formulated for oral administration.

According to some embodiments of the invention, the inflammatory disease involves cells expressing CD44vRA.

According to some embodiments of the invention, the inflammatory disease is selected from the group consisting of Rheumatoid arthritis, psoriatic arthritis, Alzheimer's disease, cancer and cardiovascular disease.

According to some embodiments of the invention, the inflammatory disease is Rheumatoid arthritis.

According to some embodiments of the invention, there is provided an isolated polynucleotide comprising a nucleic acid sequence encoding the isolated polypeptide.

According to some embodiments of the invention there is provided a nucleic acid construct comprising the isolated polynucleotide.

According to some embodiments of the invention there is provided a method of determining potency of a batch of the isolated polypeptide, the composition of matter or the pharmaceutical composition, the method comprising:

(a) contacting a batch of the isolated polypeptide, the composition of matter or the pharmaceutical composition with fibroblasts obtained from an inflammatory joint of a Rheumatoid arthritis patient; and (b) determining survival of the fibroblasts following a predetermined incubation time, so as to determine the potency of the batch.

According to some embodiments of the invention, the method comprising synthesizing the isolated polypeptide, the composition of matter or the pharmaceutical composition with a modification prior to the contacting.

According to some embodiments of the invention, reduced survival of the fibroblasts following the contacting is indicative that the batch is potent.

According to some embodiments of the invention, the method comprising comparing the survival of the cells with survival of the cells following contacting with a reference standard batch of the isolated polypeptide, the composition of matter or the pharmaceutical composition, so as to determine the relative potency of the batch.

According to some embodiments of the invention, the method is effected in-vitro or ex-vivo.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows Liquid chromatography-mass spectrometry (LCMS) analysis demonstrating the % stability of the 5-mer RA peptide (SEQ ID NO: 1) following storage at the indicated temperatures; assuming that storage at −20° C. represents 100% stability.

Figure 2A:
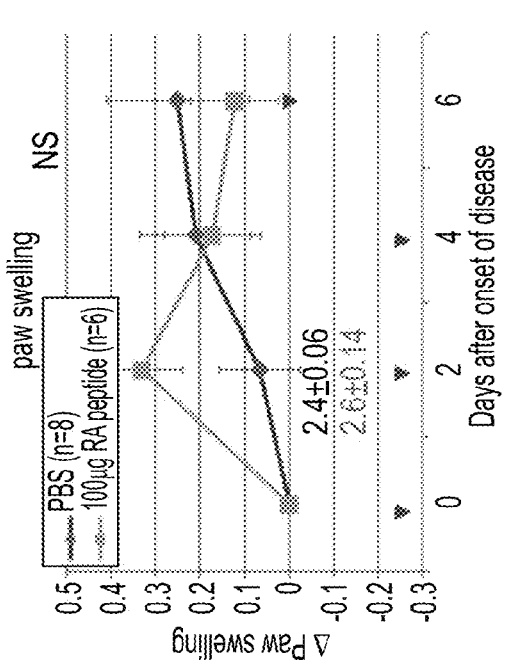
Figure 2B:
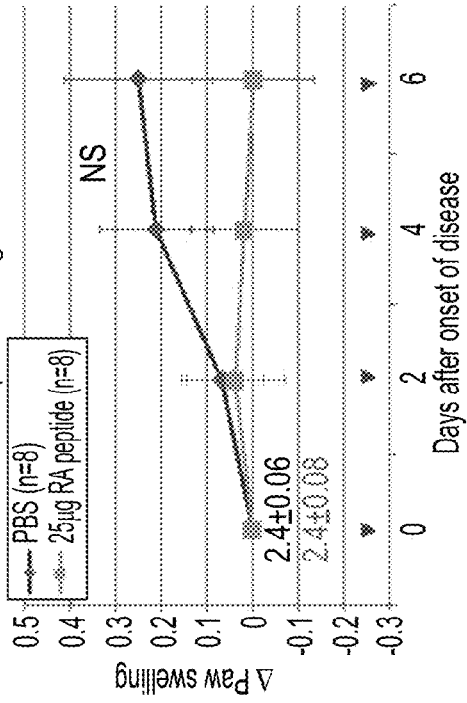
Figure 2C:
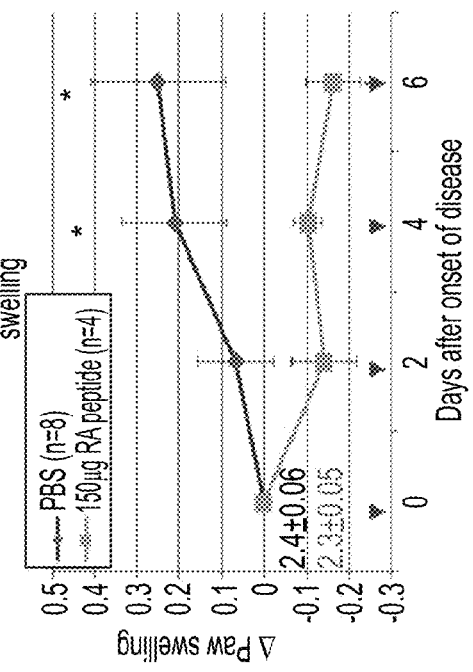

FIGS. 2A-C are graphs demonstrating that the 9-mer RA peptide (SEQ ID NO: 3) reduces joint inflammation in collagen-induced arthritis (CIA) mice on DBA/1 background. The Figures show paw swelling following injection of the 9-mer peptide at a dose of 25 μg (FIG. 2A), 100 μg (FIG. 2B) or 150 μg (FIG. 2C) at the indicated time points (marked by arrow heads). PBS was injected as control. The y-axis represents Δ paw swelling indicating the difference (by mm) between the width of the paw at each of the measurement time points and the width of the paw at the onset of disease (time 0). The results are expressed as mean±SE; the number of mice in each group (n) is indicated in insets of each Figure; *P<0.05.

FIGS. 3A-C demonstrate that treatment with the 5-mer RA peptide (SEQ ID NO: 1) can restore normal histology of the inflamed joint in CIA mice on C57BL/6 background. FIGS. 3A and 3B are representative photomicrographs of H&E stained hind limb joint sections from mice treated with PBS control (FIG. 3A) or 5-mer RA peptide (FIG. 3B). FIG. 3C is a graph summarizing the average inflammatory score as evaluated by histological examination of H&E stained hind limb joint sections from mice treated with PBS control (n=7) or 5-mer RA peptide (n=7), wherein 0 indicates no infiltration and 4 indicates massive infiltration. p<0.0001.

Figure 4:
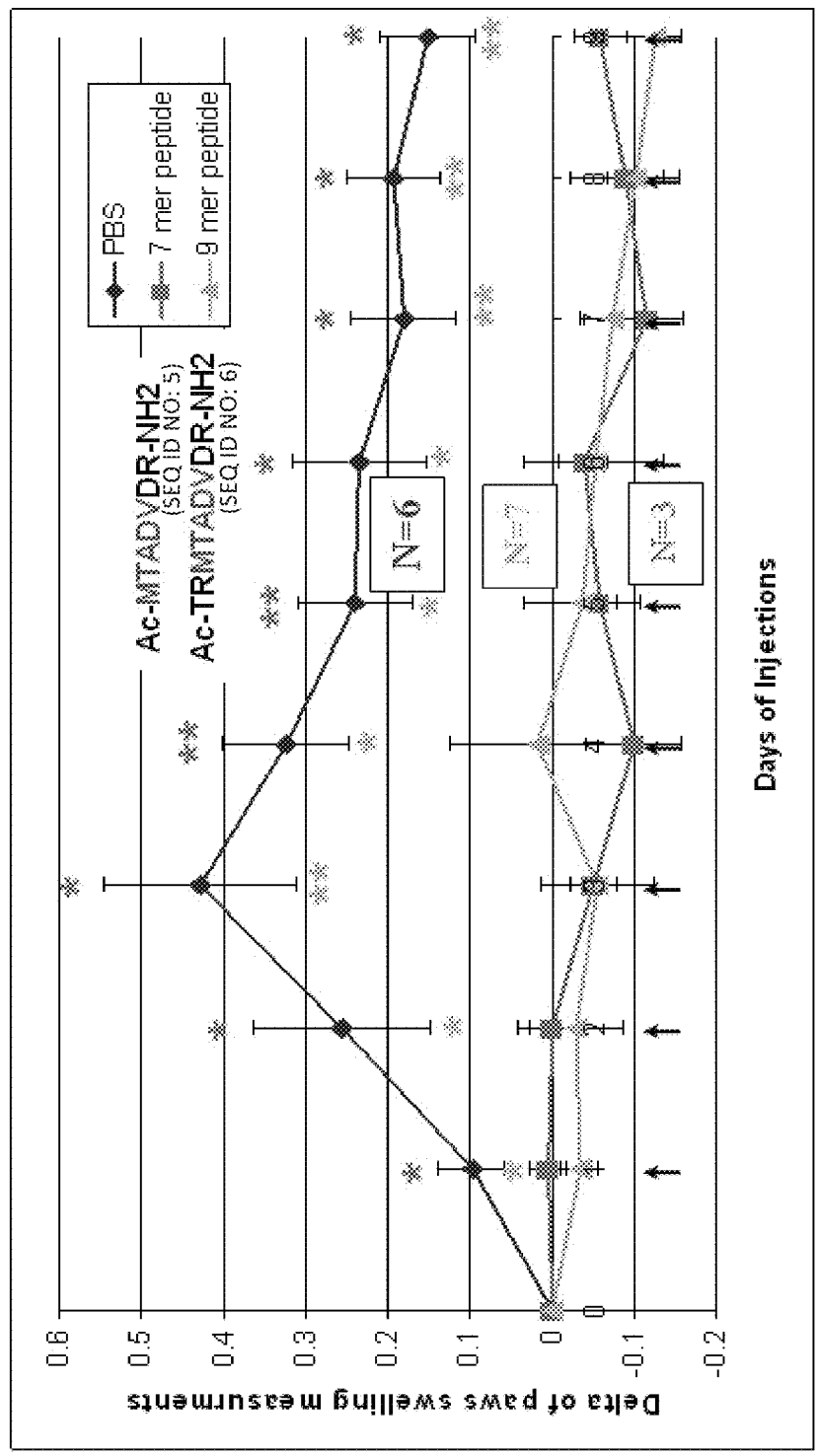

FIG. 4 is a graph demonstrating that the 7- and 9-mer protected RA peptides (SEQ ID NOs: 5-6) reduce joint inflammation in CIA mice on DBA/1 background. The Figure shows paw swelling following injection of the peptides at a dose of 200 µg at the indicated time points (marked by arrows). PBS was injected as control. The y-axis represents Δ paw swelling indicating the difference (by mm) between the width of the paw at each of the measurement time points and the width of the paw at the onset of disease (time 0). The results are expressed as mean±SE; the number of mice in each group (n) is indicated in insets of each Figure; *P<0.05, **p<0.01.

Figure 5A:
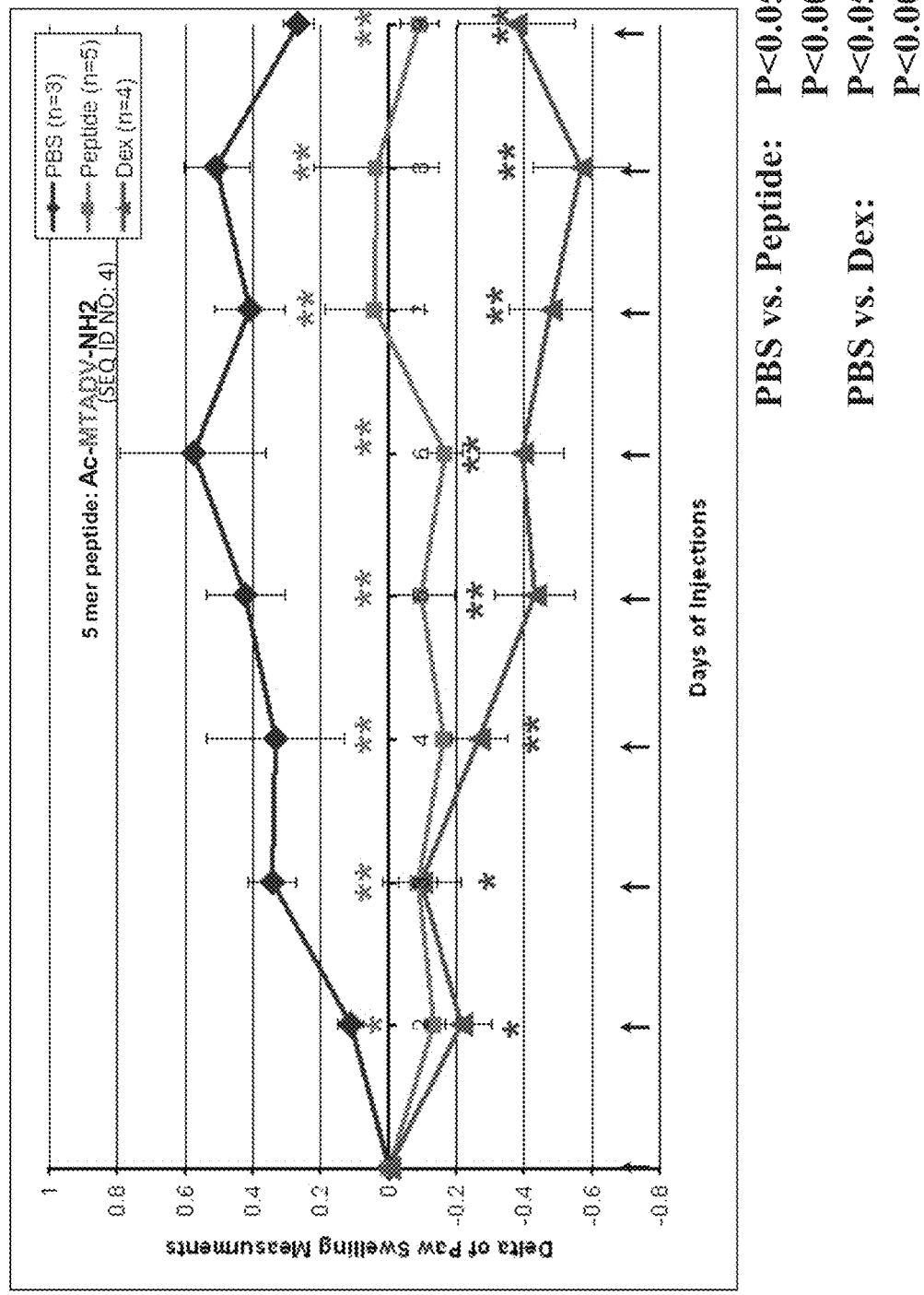
Figure 5B:
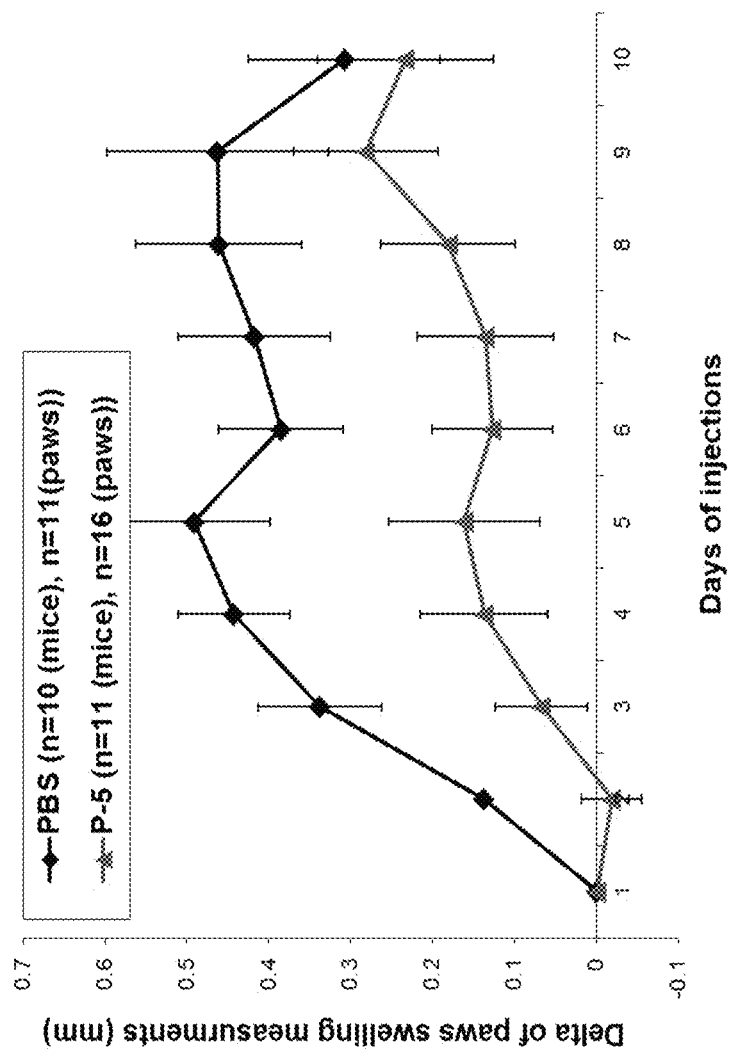

FIGS. 5A-B are graphs demonstrating that the 5-mer protected RA peptide (SEQ ID NO: 4) reduces joint inflammation in CIA mice on DBA/1 background. The Figures show paw swelling following injection of the peptide at a dose of 200 µg at the indicated time points (marked by arrows). PBS (FIGS. 5A and 5B) or Dexamethasone (Dex) (FIG. 5A) were injected as control. The y-axis represents Δ paw swelling indicating the difference (by mm) between the width of the paw at each of the measurement time points and the width of the paw at the onset of disease (time 0). The results are expressed as mean±SE; the number of mice in each group (n) is indicated in insets of each Figure; *P<0.05, **p<0.01.

Figure 6:
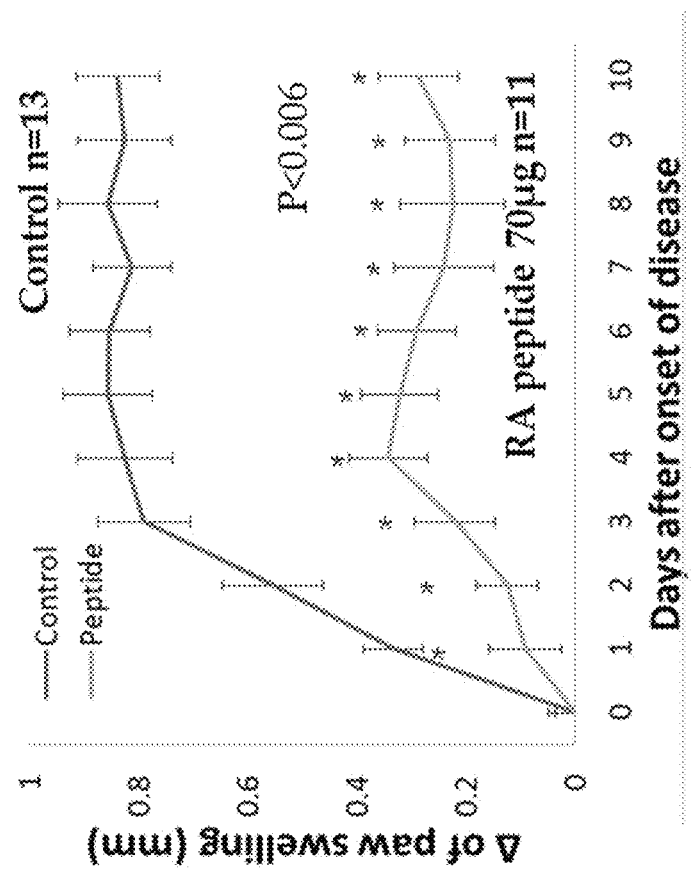

FIG. 6 is a graph demonstrating that the 5-mer protected RA peptide (SEQ ID NO: 4) reduces joint inflammation in CIA mice on C57BL background. The Figures show paw swelling following injection of the peptide at a dose of 70 µg for 10 consecutive days following onset of disease. PBS was injected as control. The y-axis represents Δ paw swelling indicating the difference (by mm) between the width of the paw at each of the measurement time points and the width of the paw at the onset of disease (time 0). The results are expressed as mean±SE; *P<0.006.

Figure 7A:
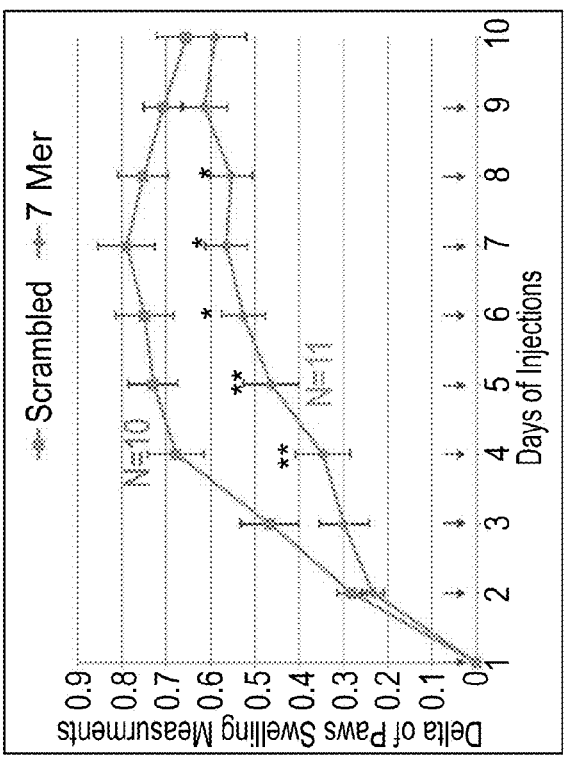
Figure 7B:
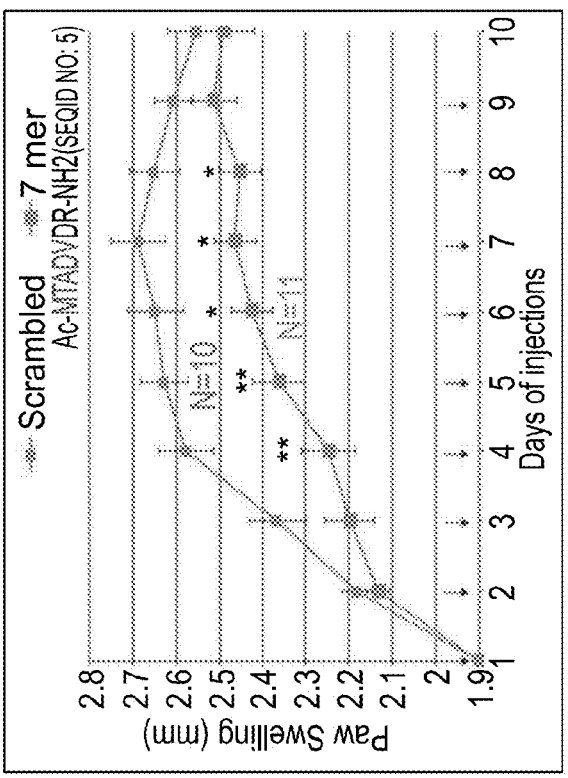
Figure 7C:
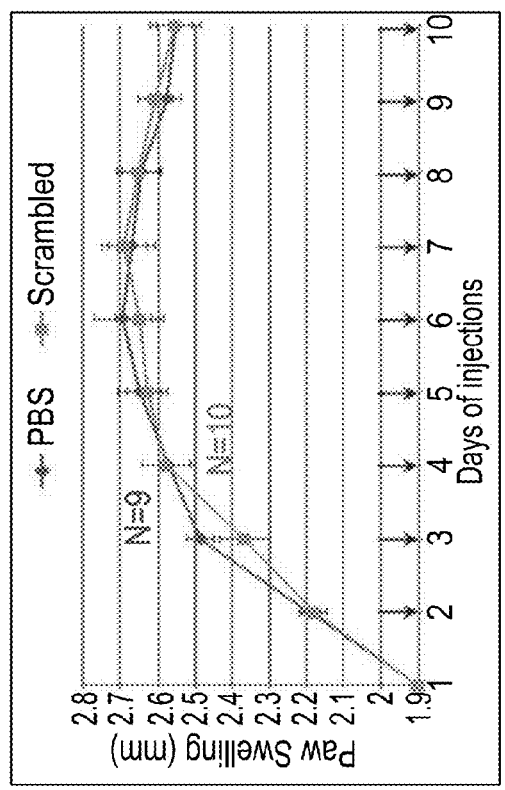

FIGS. 7A-C are graphs demonstrating that the 7-mer protected RA peptide, which includes the core MTADV sequence (SEQ ID NO: 5), reduces joint inflammation in CIA mice on DBA/1 background, while the non-specific core scrambled 7-mer peptide (SEQ ID NO: 7) has no effect on joint inflammation in this model. The Figures show paw swelling following injection of the peptides at a dose of 200 µg at the indicated time points (marked by arrows). PBS was injected as control. The y-axis represents paw swelling in mm (FIGS. 7A and 7C) or Δ paw swelling (FIG. 7B) indicating the difference between the width of the paw at each of the measurement time points and the width of the paw at the onset of disease (time 0, FIG. 7B). The results are expressed as mean±SE; the number of mice in each group (n) is indicated in insets of each Figure; *P<0.05, **p<0.005.

Figure 8:
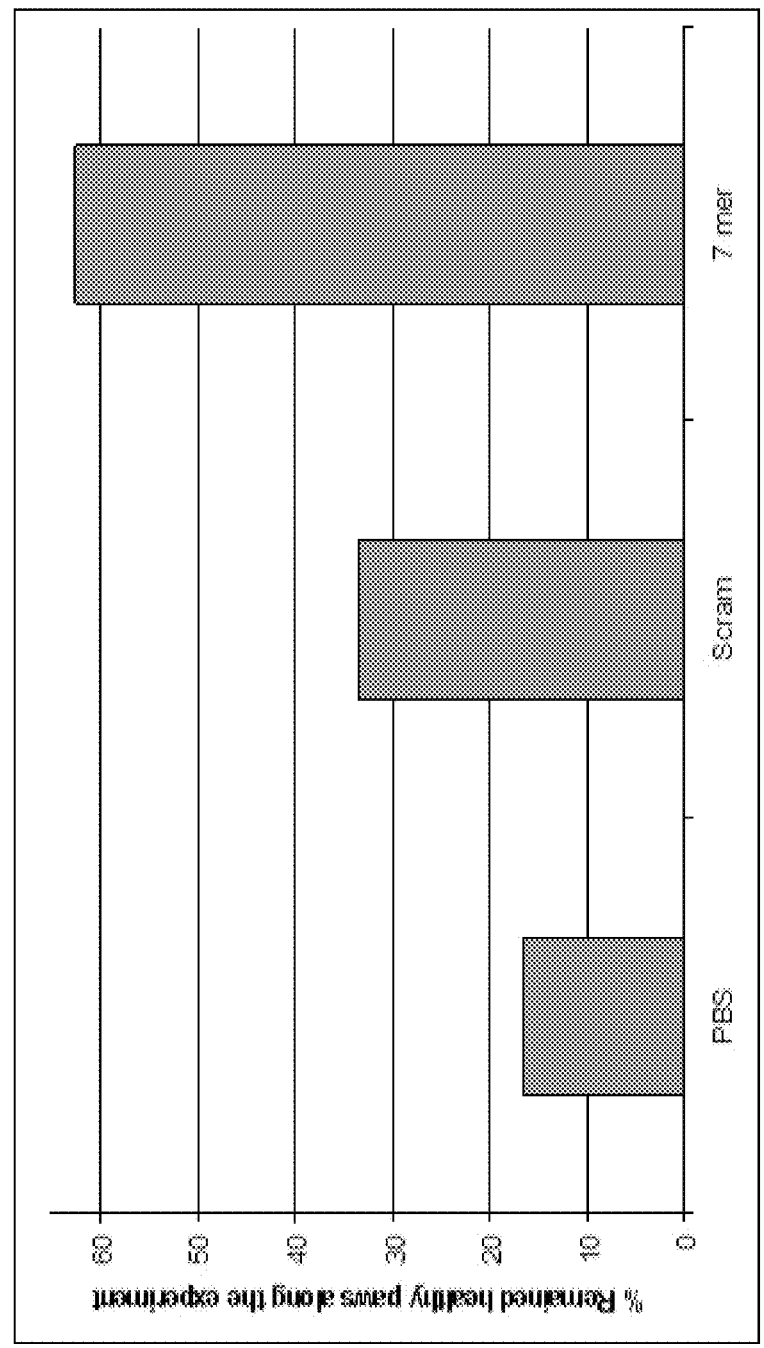

FIG. 8 is a bar graph showing the percentages of healthy hind paws in CIA mice following injection of 7-mer protected RA peptide (SEQ ID NO: 5) or non-specific scrambled 7-mer peptide (SEQ ID NO: 7) according to the experimental method described in Table 6. PBS was injected as control.

Figure 9A:
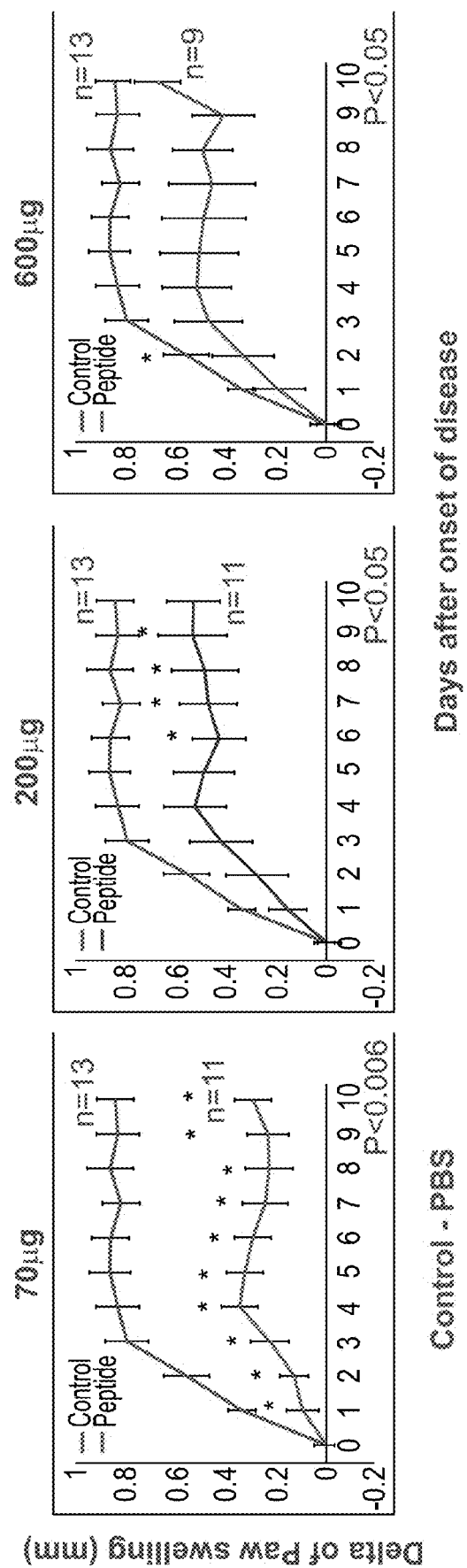
Figure 9B:
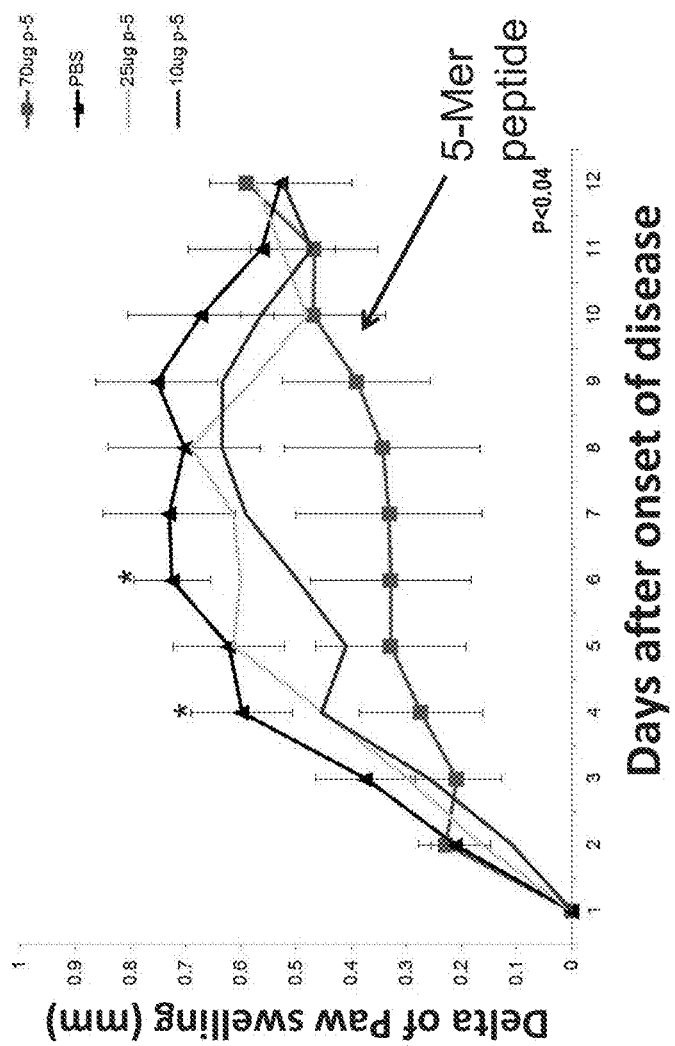

FIGS. 9A-B are graphs demonstrating that a dose of 70 µg per injection is the optimal dose for inhibiting joint inflammation in CIA mice on C57BL/6 background by the 5-mer protected RA peptide (SEQ ID NO: 4). The Figures show paw swelling following injection of the peptide at a dose of 70, 200 and 600 µg (FIG. 9A) or 10, 25 and 70 µg (FIG. 9B) for 10 consecutive days following onset of disease. PBS was injected as control. The y-axis represents Δ paw swelling indicating the difference between the width of the paw at each of the measurement time points and the width of the paw at the onset of disease (time 0). The results are expressed as mean±SE; the number of mice in each group (n) is indicated in insets of each graph; *P is indicated on each graph.

Figure 10:
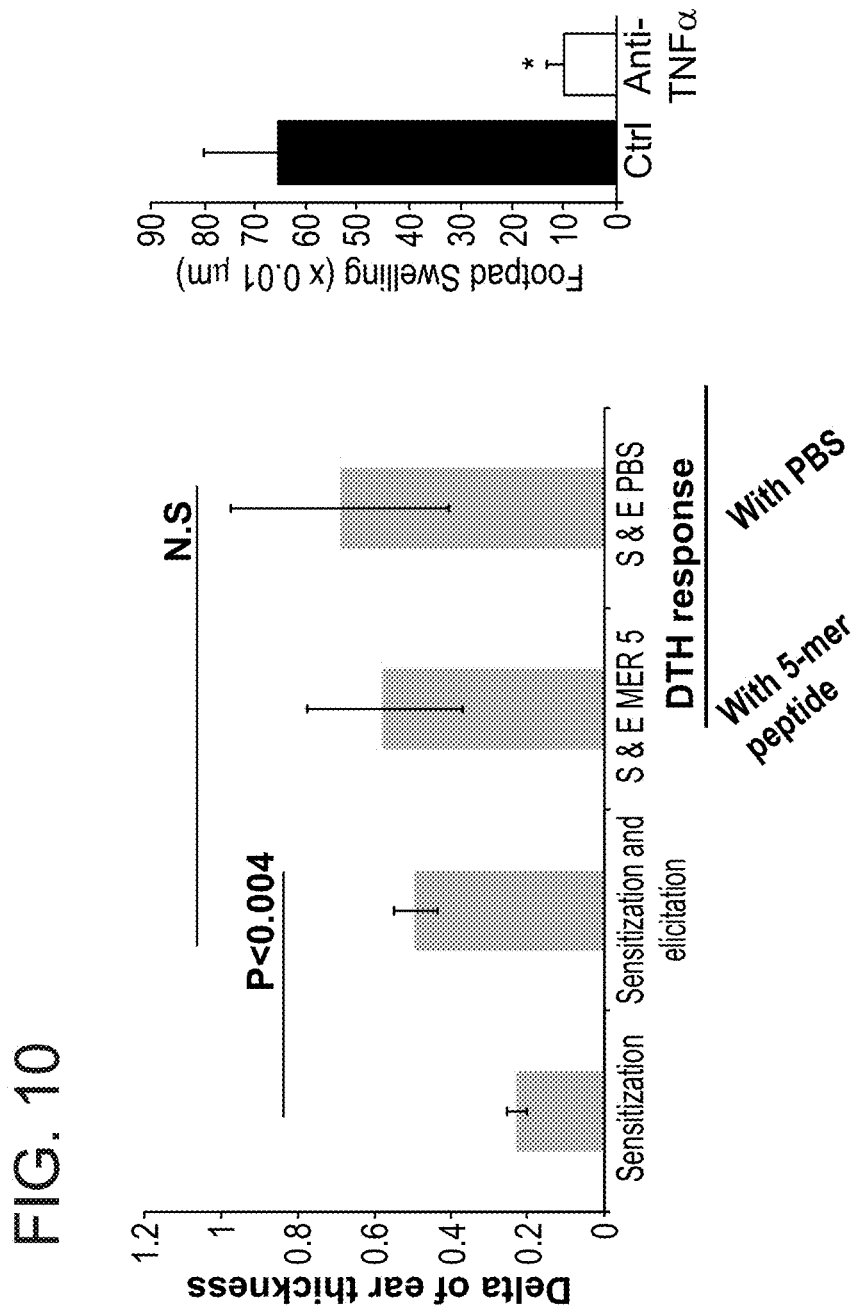

FIG. 10 shows graphs demonstrating the effect of the 5-mer RA peptide (SEQ ID NO: 1) on delayed type hypersensitivity (DTH) response in C57BL/6 mice. The y-axis represents the difference in thickness between the right and the left ears on day 7. Treatment with PBS and anti-TNFα served as positive and negative control, respectively. The results are expressed as mean±SE. The DTH protocol comprised sensitization with Oxazolone on day 0; elicitation (challenge) in the ear with Oxazolone on day 6; and measurement of ear thickness day 7. PBS or peptide were injected from day −1 to day 7.

Figure 11:
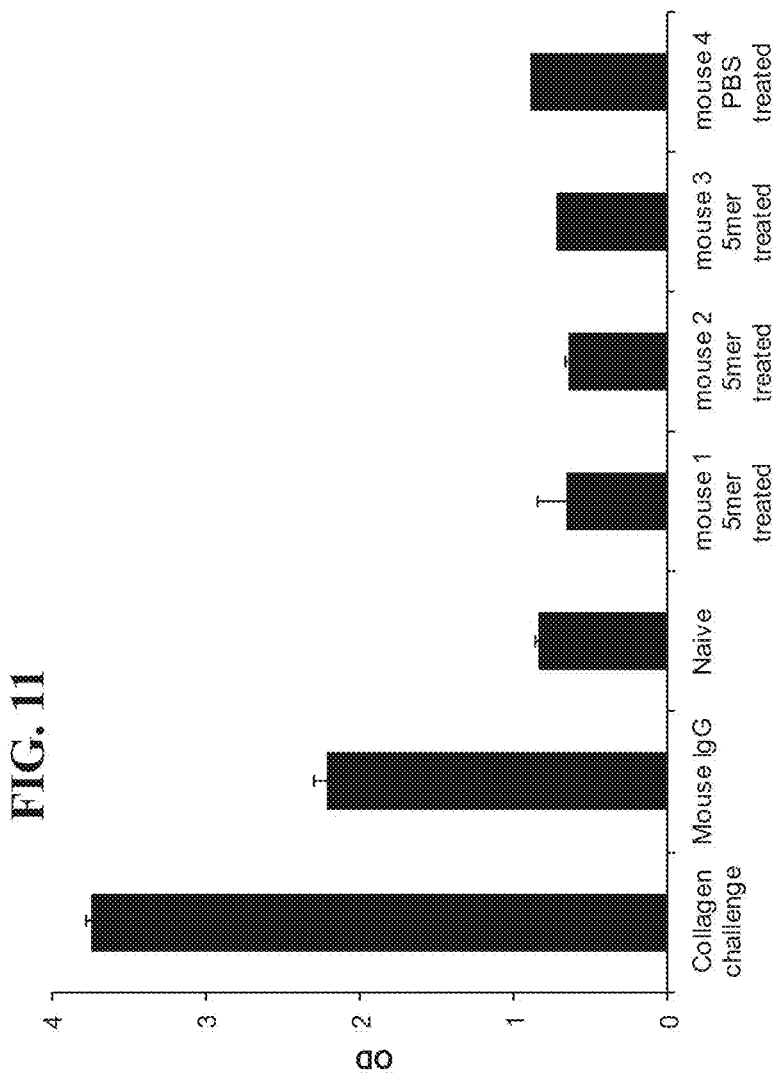

FIG. 11 is a graph showing absence of neutralizing anti-peptide specific antibodies in the serum of mice treated with the 5-mer peptide (SEQ ID NO: 1), as determined by ELISA. ELISA plates coated with the 5-mer peptide or with collagen and mouse IgG, which served as positive controls. Sera from mice treated with the 5-mer peptide or with PBS were added to plate wells. Serum from naïve mice and mice treated with PBS served as negative controls.

Figure 12:
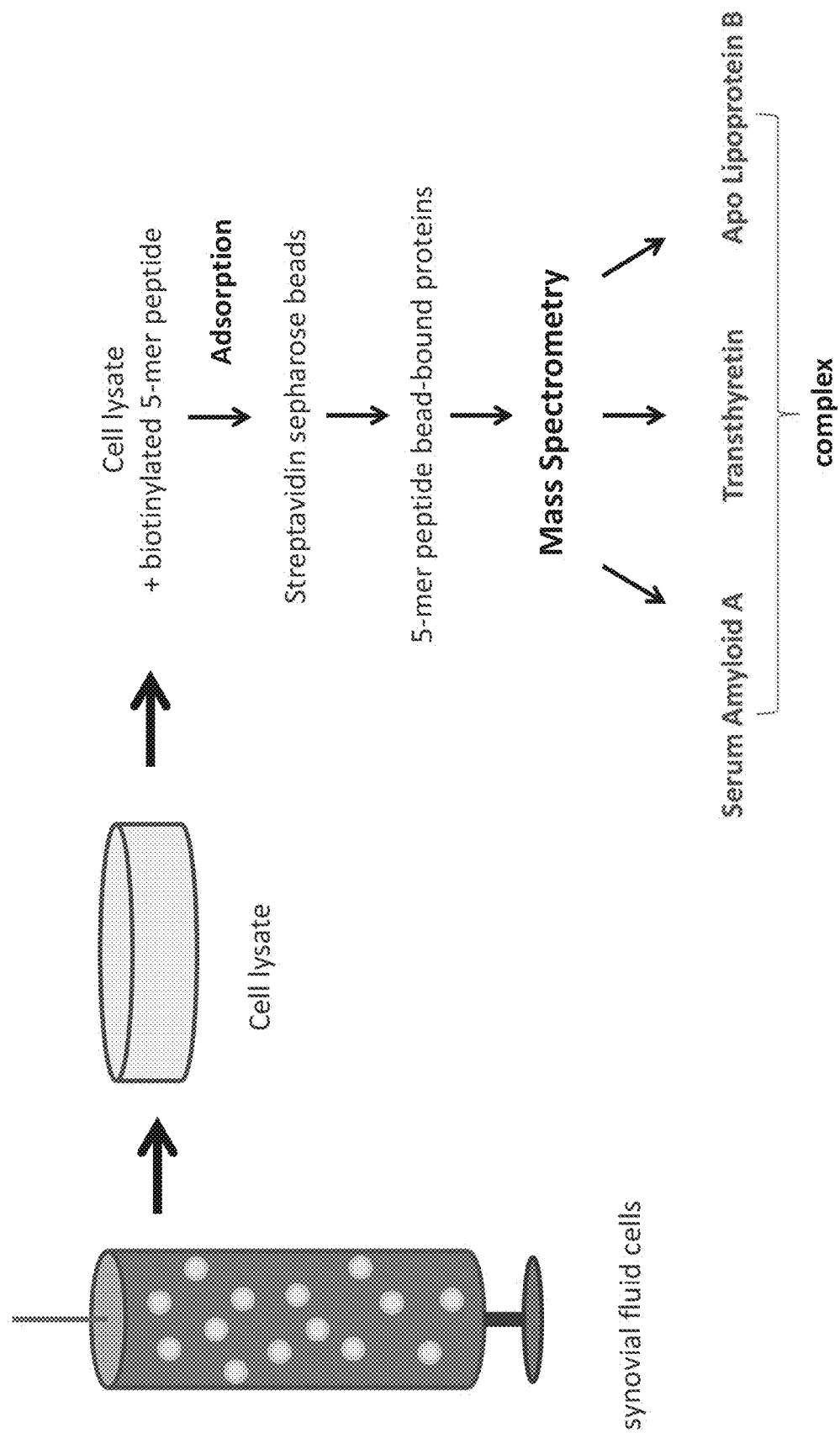

FIG. 12 is a schematic representation of the procedure used for identification of the 5-mer peptide target proteins.

Figure 13:
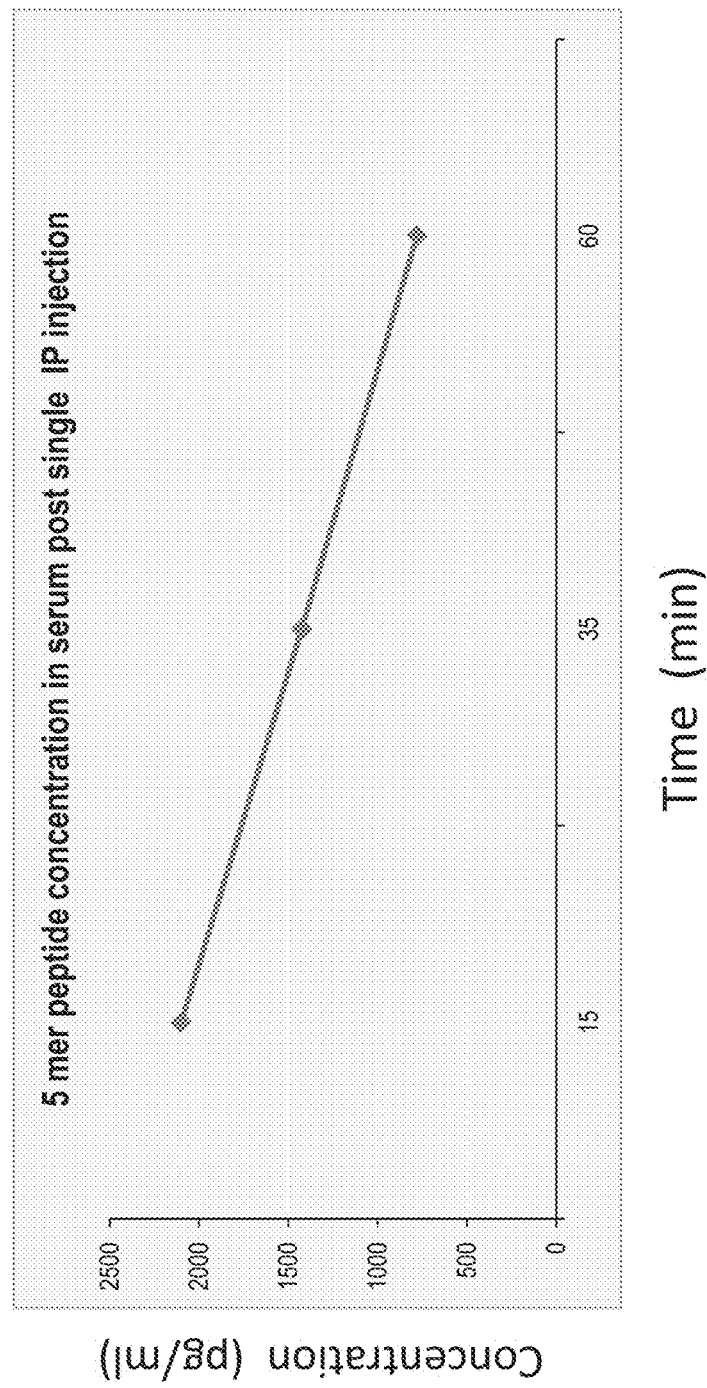

FIG. 13 is a graph showing the pharmacokinetic elimination of the 5-mer RA peptide (SEQ ID NO: 1) in the serum of mice following a single injection of the peptide.

Figure 14:
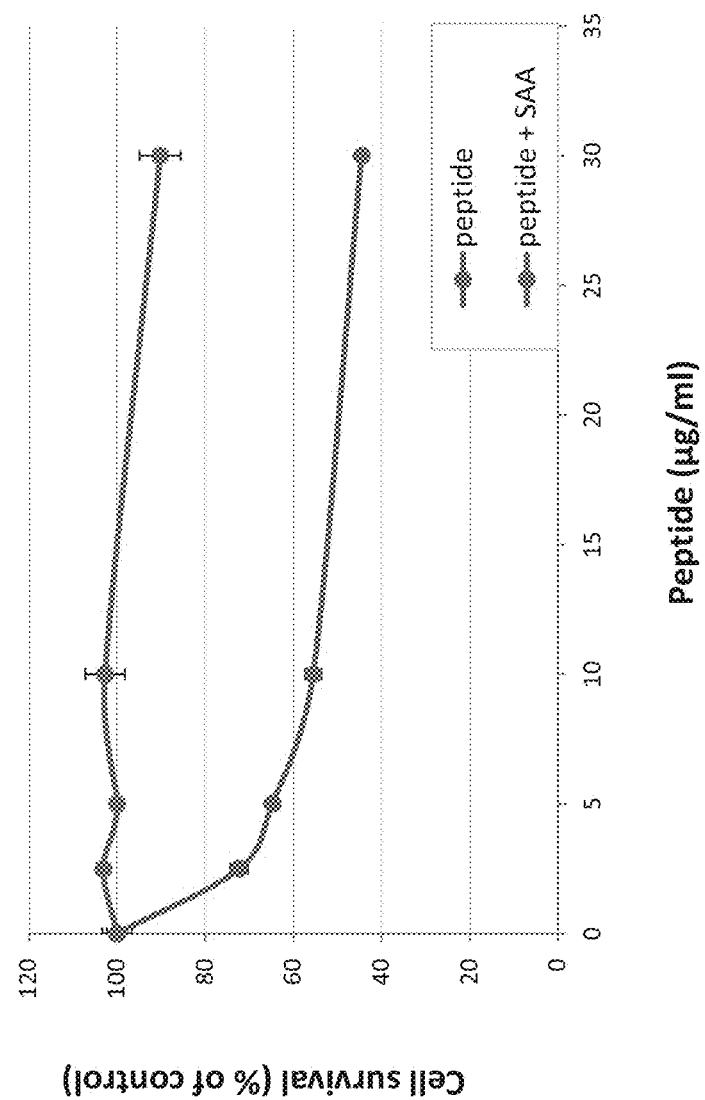

FIG. 14 is a graph demonstrating the in vitro effect of the 5-mer RA peptide (SEQ ID NO: 1) on survival of fibroblasts isolated from the inflammatory joint of an RA patient, as determined by a MTT assay.

Figure 15:
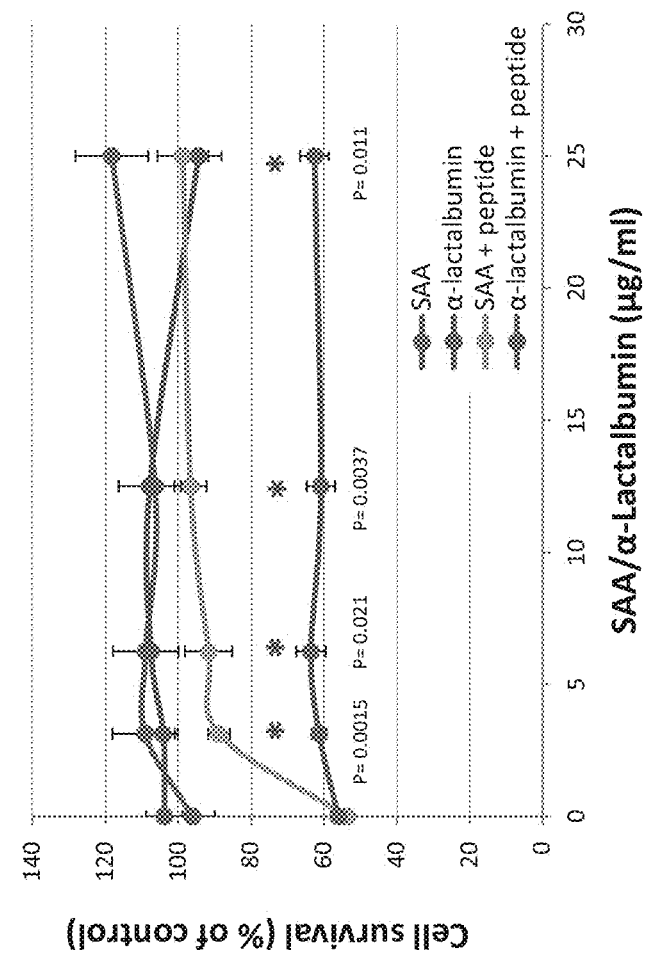

FIG. 15 is a graph demonstrating that Serum Amyloid A (SAA) prevents the in vitro effect of the 5-mer RA peptide (SEQ ID NO: 1) on survival of fibroblasts isolated from the inflammatory joint of an RA patient, as determined by a MTT assay. Lactalbumin (LA) was used as a non-specific control. The 5-mer peptide was added in a constant concentration (25 µg/ml); the x-axis indicates SAA and LA concentration.

Figure 16:
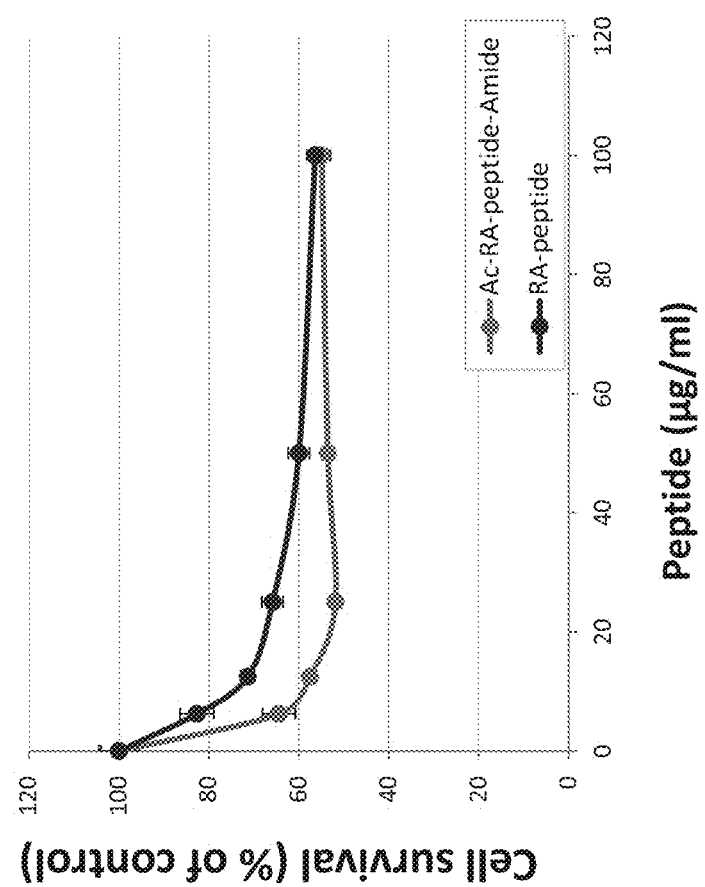

FIG. 16 is a graph demonstrating the in vitro effect of the 5-mer RA peptide (SEQ ID NO: 1) on survival of fibroblasts isolated from the inflammatory joint of an RA patient in comparison to the 5-mer protected RA peptide (SEQ ID NO: 4), as determined by a MTT assay.

DESCRIPTION OF SPECIFIC EMBODIMENTS OF THE INVENTION

The present invention, in some embodiments thereof, relates to an isolated polypeptide of CD44 and, more particularly, but not exclusively, to an isolated polypeptide of CD44vRA and its use in the treatment of inflammatory disease.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

CD44 is a cell surface adhesion molecule involved in multiple cellular functions, including cell-cell and cell-matrix interactions, cell migration, programmed cell death or, conversely, cell survival and proliferation. The genomic sequence of human CD44 includes 5 constant exons at the 5' terminus and 5 constant exons at the 3' terminus, as well as 9 variant exons encompassed therebetween. Several dozens of splice variants of CD44 are known to date. CD44s (SEQ ID NO: 9), which does not contain any variant exon, is the most ubiquitous form and is expressed by most cell types. Joint inflammatory cells of patients with psoriatic arthritis (PA), rheumatoid arthritis (RA) present a sequence of alternatively spliced CD44 variant designated CD44vRA (SEQ ID NO: 11), not expressed on keratinocytes nor peripheral blood leukocytes (PBLs) of healthy donors.

Whilst reducing the present invention to practice, the present inventors have now uncovered that peptides as short as 5, 7 or 9 mers comprising a MTADV sequence resulting from inclusion of alanine in the splicing junction between variant exon 4 and variant exon 5 of CD44vRA are capable of inhibiting joint inflammation in a CIA mouse model (the mouse analogue of human RA). Without wishing to be bound by theory it is believed that the polypeptides of some embodiments of the invention elicit their activity by competing with the natural ligand of CD44vRA.

As is illustrated hereinunder and in the examples section, which follows, the present inventors have synthesized 5-, 7- and 9-mer peptides (SEQ ID NOs: 1-3, also denoted herein as "RA peptides") and respective peptides with Acetyl and Amide protecting residues, at the amino and carboxyl terminal ends of the peptides respectively (SEQ ID NOs: 4-6, also denoted herein as "RA protected peptides"). The peptides comprise hydrophobic amino acids, no proteolytic sites and are stable at room temperature and 4° C. for at least 22 weeks (Example 1, FIG. 1). The synthesized RA peptides and RA protected peptides were able to reduce joint inflammation in-vivo in a CIA mouse model (Examples 2-4, FIGS. 2A-B, 3A-C; 4, 5-A-B, 6, 8 and 9A-B). Moreover, the peptides did not elicit generation of neutralizing anti-peptide specific antibodies nor affected general immune response as evaluated by delayed hypersensitivity (DTH) response (Example 5-6, FIGS. 10-11). Importantly, a scrambled non-specific 7-mer protected peptide (SEQ ID NO: 7) had no effect on joint inflammation in the CIA mouse model (Example 3 FIGS. 7A-B and 8). Mass spectrometry analysis further revealed few potential target proteins of the RA peptides, namely Serum amyloid A, Transthyretin and Apolipoprotein B (Example 7, FIG. 12). In addition the inventors have developed a novel in-vitro assay to test the activity of the RA peptides and RA protected peptides (Example 9, FIGS. 14-16).

Consequently, the present teachings suggest the use of compositions comprising the RA- and RA-protected peptides in the treatment of inflammatory diseases.

Thus, according to a first aspect of the present invention, there is provided an isolated polypeptide consisting of an amino acid sequence selected form the group consisting of SEQ ID NOs: 1-3.

According to specific embodiments the polypeptide is as set forth in SEQ ID NO: 1.

According to specific embodiments the polypeptide is as set forth in SEQ ID NO: 2.

According to specific embodiments the polypeptide is as set forth in SEQ ID NO: 3.

According to an aspect of the present invention, there is provided an isolated end-capping modified polypeptide comprising an amino acid sequence selected from the group consisting of SEQ ID NO: 1-3, wherein said modified polypeptide comprises an anti-inflammatory activity.

According to specific embodiments, the polypeptide amino acid sequence of the end-capping modified polypeptide consists of an amino acid sequence selected form the group consisting of SEQ ID NOs: 1-3.

According to another aspect of the present invention there is provided a composition of matter comprising the isolated polypeptide and a non-proteinaceous moiety attached to the isolated polypeptide, wherein the isolated fusion polypeptide comprises an anti-inflammatory activity.

According to another aspect of the present invention there is provided an isolated fusion polypeptide comprising the isolated polypeptide having a C and/or N terminally attached amino acid sequence, wherein said C terminally amino acid sequence is a non-contiguous CD44vRA amino acid sequence with said isolated fusion polypeptide; and wherein said fusion polypeptide comprises an anti-inflammatory activity.

The terms "peptide" and "polypeptide" which are interchangeably used herein encompass native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body, more capable of penetrating into cells improving clearance, biodistribution and/or pharmacokinetics. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (e.g. 2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodemosine, nor-valine, nor-leucine and ornithine. Furthermore, the term "amino acid" includes both D- and L-amino acids (stereoisomers).

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
| --- | --- | --- | --- |
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyeglycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The amino acids of the polypeptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having neuroprotective properties.

The peptides of some embodiments of the invention are preferably utilized in a linear form, although it will be appreciated that in cases where cyclicization does not severely interfere with peptide characteristics, cyclic forms of the peptide can also be utilized.

Since the present peptides are preferably utilized in therapeutics which requires the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

As mentioned, the N and C termini of the peptides of the present invention may be protected by functional groups. Suitable functional groups are described in Green and Wuts, "Protecting Groups in Organic Synthesis", John Wiley and Sons, Chapters 5 and 7, 1991, the teachings of which are incorporated herein by reference. Thus, the polypeptide may be modified at the N-(amine) terminus and/or the C-(carboxyl) terminus thereof so as to produce an end capping modified peptide.

As used herein, the phrases "end-capping modified polypeptide" and "protected polypeptide", which are interchangeably used herein, refer to a polypeptide which has been modified at the N-(amine) terminus and/or the C-(carboxyl) terminus thereof. The end-capping modification refers to the attachment of a chemical moiety to the terminus of the polypeptide, so as to form a cap. Such a chemical moiety is referred to herein as an end capping moiety and is typically also referred to herein and in the art, interchangeably, as a peptide protecting moiety or group. Hydroxyl protecting groups include but are not limited to esters, carbonates and carbamate protecting groups. Amine protecting groups include but are not limited to alkoxy and aryloxy carbonyl groups. Carboxylic acid protecting groups include but are not limited to aliphatic, benzylic and aryl esters.

The phrase "end-capping moiety", as used herein, refers to a moiety that when attached to the terminus of the peptide, modifies the N and/or C terminal ends(s) of the peptide. The end-capping modification typically results in masking the charge of the peptide terminus, and/or altering chemical features thereof, such as, hydrophobicity, hydrophilicity, reactivity, solubility and the like. By selecting the nature of the end capping modification, the hydrophobicity/hydrophilicity, as well as the solubility of the peptide can be finely controlled. According to specific embodiments, the protecting groups facilitate transport of the peptide attached thereto into a cell. These moieties can be cleaved in vivo, either by hydrolysis or enzymatically, inside the cell.

According to specific embodiments, the end-capping modification does not compromise the biological activity (i.e. anti-inflammatory activity) of the polypeptide. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

According to specific embodiments, the end-capping comprises an N terminus end-capping.

Representative examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denote d herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

According to specific embodiments, the N terminus end-capping comprises an Acetyl.

According to specific embodiments, the end-capping comprises a C terminus end-capping.

Representative examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

According to specific embodiments, the C terminus end-capping comprises an Amide.

Other end-capping modifications of peptides include replacement of the amine and/or carboxyl with a different moiety, such as hydroxyl, thiol, halide, alkyl, aryl, alkoxy, aryloxy and the like.

According to specific embodiments, the peptide is modified only at the N-terminus or the C-terminus thereof.

According to other specific embodiments, the peptide is modified at both the N-terminus and the C-terminus.

According to specific embodiments, the peptide is modified at the N-terminus with an Acetyl and at the C terminus with an Amide.

According to specific embodiments the end-capping modified polypeptide is selected form the group consisting to SEQ ID NOs: 4-6.

The present invention further provides polypeptide conjugates and fusion polypeptides comprising peptides, analogs and derivatives according to the invention.

Thus, as mentioned, according to an aspect of the present invention there is provided an isolated fusion polypeptide comprising the isolated polypeptide having a C and/or N terminally attached amino acid sequence, wherein said C terminally amino acid sequence is a non-contiguous CD44vRA amino acid sequence with said isolated fusion polypeptide; and wherein said fusion polypeptide comprises an anti-inflammatory activity.

As used herein, the phrase "non-contiguous CD44vRA amino acid sequence" refers to a fusion polypeptide that does not comprise an amino acid sequence of SEQ ID NOs: 1, 2 or 3 directly attached in its C terminus to an amino acid sequence of CD44vRA starting at coordinates 306, 308 or 308, respectively, of SEQ ID NO: 11.

According to specific embodiments, the isolated polypeptide and the attached amino acid sequence are covalently attached, directly or through a spacer or a linker which can be a synthetic or an amino acid linker.

As used herein the term "CD44" refers to the cell surface protein that is expressed in a large number of mammalian cell types and is encoded by the CD44 gene. According to a specific embodiment the CD44 is the human CD44 gene. The standard isoform, designated CD44, comprising exons 1-5 and 16-20 is expressed in most cell types and is set forth in GeneBank Accession Numbers NM_000610 and NP_000601 (SEQ ID NOs: 8 and 9).

As used herein the term "CD44vRA" (SEQ ID NO: 10 and 11) refers to a CD44 variant which is expressed in inflammation sites, e.g. on synovial fluid cells of RA patients but not on PBLs of healthy individuals. CD44vRA variant is a naturally occurring sequence which is presumably produced by alternative splicing of the primary transcript of the known CD44 gene which occurs in cells in inflammatory sites (e.g. in joints of RA patients) and does not arise from truncation or mutation of the known CD44 gene. This CD44vRA variant sequence comprises Exons 1-5, 15-17 and 19 of the constant part of the CD44 gene as well as Exons 7-14 (v3-v10) of the variable region of the gene. The variant coding sequence comprises three additional bases (CAG) that are transcribed from the end of the intron bridging Exon v4 to Exon v5 and are inserted at the 5' end of Exon v5. This extra CAG sequence results in the insertion of a new codon for the amino acid alanine in position 303 of SEQ ID NO: 11 while leaving the reading frame intact.

The terms "CD44" and "CD44vRA", also refer to CD44 and CD44vRA homologues which exhibit the desired activity (e.g. cell migration and/or cell-cell and cell-matrix interactions). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide of SEQ ID NOs: 9 and 11, or 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same.

The homolog may also refer to an ortholog, a deletion, insertion, or substitution variant, including an amino acid substitution, as long as it retains the activity.

Sequence identity or homology can be determined using any protein or nucleic acid sequence alignment algorithm such as Blast, ClustalW, and MUSCLE.

According to other specific embodiments of the invention, the peptide is attached to a non-proteinaceous moiety.

According to specific embodiments, the isolated polypeptide and the attached non-proteinaceous moiety are covalently attached, directly or through a spacer or a linker.

The phrase "non-proteinaceous moiety" as used herein refers to a molecule not including peptide bonded amino acids that is attached to the above-described peptide. According to a specific embodiment the non-proteinaceous is a non-toxic moiety. Exemplary non-proteinaceous moieties which may be used according to the present teachings include, but are not limited to a drug, a chemical, a small molecule, a polynucleotide, a detectable moiety, polyethylene glycol (PEG), Polyvinyl pyrrolidone (PVP), poly(styrene comaleic anhydride) (SMA), and divinyl ether and maleic anhydride copolymer (DIVEMA). According to specific embodiments of the invention, the non-proteinaceous moiety comprises polyethylene glycol (PEG).

Such a molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation as further described hereinbelow).

Bioconjugation of the polypeptide amino acid sequence with PEG (i.e., PEGylation) can be effected using PEG derivatives such as N-hydroxysuccinimide (NHS) esters of PEG carboxylic acids, monomethoxyPEG$_2$-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsvlle, Ala.)]. If desired, many of the above derivatives are available in a monofunctional monomethoxyPEG (mPEG) form. In general, the PEG added to the polypeptide of the present invention should range from a molecular weight (MW) of several hundred Daltons to about 100 kDa (e.g., between 3-30 kDa). Larger MW PEG may be used, but may result in some loss of yield of PEGylated polypeptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

Conveniently, PEG can be attached to a chosen position in the polypeptide by site-specific mutagenesis as long as the activity of the conjugate is retained. A target for PEGylation could be any Cysteine residue at the N-terminus or the C-terminus of the peptide sequence. Additionally or alternatively, other Cysteine residues can be added to the polypeptide amino acid sequence (e.g., at the N-terminus or the C-terminus) to thereby serve as a target for PEGylation. Computational analysis may be effected to select a preferred position for mutagenesis without compromising the activity.

Various conjugation chemistries of activated PEG such as PEG-maleimide, PEG-vinylsulfone (VS), PEG-acrylate (AC), PEG-orthopyridyl disulfide can be employed. Methods of preparing activated PEG molecules are known in the arts. For example, PEG-VS can be prepared under argon by reacting a dichloromethane (DCM) solution of the PEG-OH with NaH and then with di-vinylsulfone (molar ratios: OH 1: NaH 5: divinyl sulfone 50, at 0.2 gram PEG/mL DCM). PEG-AC is made under argon by reacting a DCM solution of the PEG-OH with acryloyl chloride and triethylamine (molar ratios: OH 1: acryloyl chloride 1.5: triethylamine 2, at 0.2 gram PEG/mL DCM). Such chemical groups can be attached to linearized, 2-arm, 4-arm, or 8-arm PEG molecules.

Resultant conjugated molecules (e.g., PEGylated or PVP-conjugated polypeptide) are separated, purified and qualified using e.g., high-performance liquid chromatography (HPLC) as well as biological assays.

According to specific embodiments, the CD44vRA peptide portion of the polypeptides of the invention other than those listed as consisting of SEQ ID NOs: 1-3 are 5-100, 5-50, or 5-40, or 5-20, 5-15, 5-10, 5-9, 5-7 amino acids in length.

According to specific embodiments, the peptide portion of the polypeptides of the invention does not comprise a CD44vRA amino acid sequence other than those listed as consisting of SEQ ID NOs: 1-3.

The peptides and compositions of matter of the present invention may be attached (either covalently or non-covalently) to a penetrating agent.

As used herein the phrase "penetrating agent" refers to an agent which enhances translocation of any of the attached peptide or composition of matter across a cell membrane.

According to one embodiment, the penetrating agent is a peptide and is attached to the polypeptide (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

According to specific embodiments, the polypeptide is provided in a formulation suitable for cell penetration that enhances intracellular delivery of the polypeptide as further described hereinbelow.

By way of non-limiting example, cell penetrating peptide (CPP) sequences may be used in order to enhance intracellular penetration; however, the disclosure is not so limited, and any suitable penetrating agent may be used, as known by those of skill in the art.

Cell-Penetrating Peptides (CPPs) are short peptides (≤40 amino acids), with the ability to gain access to the interior of almost any cell. They are highly cationic and usually rich in arginine and lysine amino acids. They have the exceptional property of carrying into the cells a wide variety of covalently and noncovalently conjugated cargoes such as proteins, oligonucleotides, and even 200 nm liposomes. Therefore, according to additional exemplary embodiment CPPs can be used to transport the polypeptide or the composition of matter to the interior of cells.

TAT (transcription activator from HIV-1), pAntp (also named penetratin, Drosophila antennapedia homeodomain transcription factor) and VP22 (from Herpes Simplex virus) are examples of CPPs that can enter cells in a non-toxic and efficient manner and may be suitable for use with some embodiments of the invention. Protocols for producing CPPs-cargos conjugates and for infecting cells with such conjugates can be found, for example L Theodore et al. [The Journal of Neuroscience, (1995) 15(11): 7158-7167], Fawell S, et al. [Proc Natl Acad Sci USA, (1994) 91:664-668], and Jing Bian et al. [Circulation Research (2007) 100: 1626-1633].

The polypeptides of some embodiments of the invention may be synthesized by any techniques that are known to those skilled in the art of peptide synthesis, including solid phase and recombinant techniques.

Any of the proteinaceous polypeptides described herein can be encoded from a polynucleotide. These polynucleotides can be used as therapeutics per se or in the recombinant production of the agent.

Thus, according to an aspect of the present invention there is provided an isolated polynucleotide comprising a nucleic acid sequence encoding the polypeptide of the present invention.

Thus, according to an aspect of the present invention there is provided a nucleic acid construct comprising the isolated polynucleotide.

Such a nucleic acid construct or system includes at least one cis-acting regulatory element for directing expression of the nucleic acid sequence. Cis-acting regulatory sequences include those that direct constitutive expression of a nucleotide sequence as well as those that direct inducible expression of the nucleotide sequence only under certain conditions. Thus, for example, a promoter sequence for directing transcription of the polynucleotide sequence in the cell in a constitutive or inducible manner is included in the nucleic acid construct.

The isolated polypeptides and the compositions of matter of the present invention are endowed with anti-inflammatory activity.

As used herein, the phrase "anti-inflammatory activity" refers to prevention and/or reduction of acute and/or chronic inflammatory responses and/or in preventing and/or treating an inflammatory-related disease. Assays for qualifying an anti-inflammatory activity include but are not limited to those described in the Examples section which follows using both in-vitro and in-vivo models for inflammatory conditions (e.g. RA). Non-limiting examples include paw swelling in vivo in a CIA mouse model (see e.g. Nedvetzki, et al., (2004) PNAS 101, 18081-18086), histological examination of joint sections obtained from CIA mice and in-vitro cell viability of fibroblasts obtained from synovial fluid of an RA patient as further described hereinbelow.

According to specific embodiments, the anti-inflammatory activity is not dependent on vaccination or mucosal tolerance.

According to specific embodiments, the isolated polypeptide of the composition of matter does not effect immune response in general, as may be evaluated by a delayed type hypersensitivity assay (DTH) such as disclosed in Weiss et al., (2000) Proc. Natl. Acad. Sci. USA. 97, 285-290; and in Example 5 in the Examples section which follows.

According to specific embodiments, the isolated polypeptide or the composition of matter is capable of binding a protein selected from the group consisting of serum amyloid A, Transthyretin and apolipoprotein B.

As used herein, the term "serum amyloid A" or "SAA" refer to the polynucleotide and expression product e.g., polypeptide of the SAA1, SAA2 and SAA4 genes. SAA1 is also known as serum amyloid A1, MGC1 11216, PIG4, SAA, and tumor protein p53 inducible protein 4 (TP53I4). According to specific embodiments the SAA1 refers to the human SAA1, such as provided in the following GeneBank Numbers NM_199161 and NM_000331 and Uniprot Number: P0DJI8 (SEQ ID NOs: 12-14). According to specific embodiments the SAA1 refers to the mouse SAA1, such as provided in the following GeneBank Number NM 009117 (SEQ ID NO: 15). SAA2 is also known as serum amyloid A2 and SAA. According to specific embodiments the SAA2 refers to the human SAA2, such as provided in the following GeneBank Numbers NM_001127380 and NM_030754 and Uniprot number P0DJI8 (SEQ ID NOs: 16-18). According to specific embodiments the SAA2 refers to the mouse SAA2, such as provided in the following GeneBank Numbers NM_011314 (SEQ ID NO: 19). According to specific embodiments the SAA4 refers to the human SAA4, such as provided in the following GeneBank Number NM_006512 and Uniprot Number P35542 (SEQ ID NOs: 20-21).

According to specific embodiments, the term "SAA" refers to SAA1 and SAA2 genes which belong to the serum amyloid A acute phase family of proteins.

As used herein, the term "Transthyretin", refers to the polynucleotide and expression product e.g., polypeptide of the TTR gene, which is a protein carrier of the thyroid hormone thyroxine and retinol. According to specific embodiments the transthyretin refers to the human transthyretin, such as provided in the following GeneBank Numbers NP_000362 and NM_000371 (SEQ ID NOs: 22-23). According to other specific embodiments, the transthyretin refers to the mouse transthyretin, such as provided in the following GeneBank Numbers NP_038725 and NM_013697 (SEQ ID NOs: 24-25).

As used herein, the term "apolipoprotein B", refers to the polynucleotide and expression product e.g., polypeptide of the APOB gene. According to specific embodiments the apolipoprotein B refers to the human apolipoprotein B, such as provided in the following GeneBank Numbers NP_000375 and NM_000384 (SEQ ID NOs: 26-27). According to other specific embodiments, the apolipoprotein B refers to the mouse apolipoprotein B, such as provided in the following GeneBank Numbers NP_033823 and NM_009693 (SEQ ID NOs: 28-29).

By virtue of their anti-inflammatory activity, the polypeptides and compositions of matter of the present invention may be used to treat diseases which are dependent on CD44vRA (activity or expression) for their onset or progression, such as for the treatment of inflammatory diseases, such as Rheumatoid Arthritis (RA).

Thus, according to an aspect of the present invention there is provided a method of treating an inflammatory disease in a subject in need thereof, the method comprising administering to the subject a therapeutically effective amount of the isolated polypeptide, the composition of matter or the pharmaceutical composition, thereby treating the inflammatory disease in the subject.

According to another aspect of the present invention there is provided a use of the isolated polypeptide, the composition of matter or the pharmaceutical composition for the manufacture of a medicament for the treatment of an inflammatory disease.

As used herein the term "treating" refers to inhibiting, preventing or arresting the development of a pathology (disease, disorder, or condition e.g., inflammation e.g., RA) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

According to specific embodiments, the term "treating" refers to ameliorating symptoms associated with a RA and related diseases, lessening the severity or curing the diseases, or preventing the disease from occurring, preventing the manifestation of symptoms associated with the disease before they occur, slowing down the progression of the disease or deteriorating of the symptoms associated therewith, enhancing the onset of the remission period, slowing down the irreversible damage caused in the progressive chronic stage of the disease, delaying the onset of said progressive stage, improving survival rate or more rapid recovery, or a combination of two or more of the above.

As used herein the phrase "subject in need thereof" refers to a mammalian male or female subject (e.g., human being) who is diagnosed with an inflammatory disease or is at risk of to develop an inflammatory disease. Veterinary uses are also contemplated. The subject may be of any age including neonatal, infant, juvenile, adolescent, adult and elderly adult.

Methods of determining inflammation in a subject are well known in the art and include, but are not limited to, determining in a blood sample from the subject the erythrocyte sedimentation rate (ESR); plasma viscosity; levels of C-reactive protein (CRP); levels of certain inflammatory cytokines such as IL6 and TNFα; and determination of an inflammation index such as using fibrinogen measurements and hematocrit or hemoglobin.

According to specific embodiments, the inflammatory disease involves cells expressing CD44vRA. Non-limiting examples of assays that can evaluate the expression of CD44vRA on cells include flow cytometry and immunocytochemistry.

Examples of inflammatory diseases (also referred to herein as inflammation or inflammatory condition) include, but not limited to, chronic inflammatory disease and acute inflammatory disease.

Examples for Inflammatory disease include, but not limited to inflammatory diseases associated with hypersensitivity, autoimmune diseases, infectious diseases, graft rejection diseases, allergic diseases and cancerous diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), Psoriatic Arthritis (PA), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl: S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris) 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus. Note that several same diseases are can be classified to different classes of hypersensitivity, because the heterogeneity of these diseases.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris) 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol (1999) 18(1-2):83; Oshima M. et al., Eur J Immunol (1990) 20(12):2563), neuropathies, motor neuropathies (Kornberg A J. J Clin Neurosci. (2000) 7(3):191); Guillain-Barre syndrome and autoimmune neuropathies (Kusunoki S. Am J Med Sci. (2000) 319(4):234), myasthenia, Lambert-Eaton myasthenic syndrome (Takamori M. Am J Med Sci. (2000) 319(4):204); paraneoplastic neurological diseases, cerebellar atrophy, paraneoplastic cerebellar atrophy and stiff-man syndrome (Hiemstra H S. et al., Proc Natl Acad Sci units S A (2001) 98(7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyper-acute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation, Acute promyelocytic leukemia, Acute nonlymphocytic leukemia with increased basophils, Acute monocytic leukemia. Acute myelomonocytic leukemia with eosinophilia; Malignant lymphoma, such as Burkitt's Non-Hodgkin's; Lymphocytic leukemia, such as Acute lymphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletal myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

According to specific embodiments the inflammatory disease is selected from the group consisting of Rheumatoid arthritis (RA), psoriatic arthritis, Alzheimer's disease, cancer and cardiovascular disease.

According to other specific embodiments the inflammatory disease comprises RA.

As used herein, the phrase "rheumatoid arthritis (RA)" refers to an autoimmune disease which primarily affects the joints. RA includes, but is limited to, adult RA, juvenile idiopathic arthritis, juvenile RA and juvenile chronic arthritis. RA can be diagnosed according to the American Rheumatoid Association criteria for the classification of rheumatoid arthritis, or any similar criteria and includes active, early (active RA diagnosed for at least 8 weeks but no longer than four years) and incipient (polyarthritis that does not fully meet the criteria for a diagnosis of RA, in association with the presence of RA-specific prognostic biomarkers such as anti-CCP and shared epitope) RA.

Example of RA clinical parameters symptoms that can be monitored to indicate improvement during treatment with the isolated polypeptides and composition of matter of the invention are:

Morning stiffness for at least one hour and present for at least six weeks;

Swelling of three or more joints for at least six weeks;

Swelling of wrist, metacarpophalangeal, or proximal interphalangeal joints for at least six weeks Symmetric joint swelling;

Hand x-ray changes that include erosions or unequivocal bony decalcification;

Rheumatoid subcutaneous nodules; and

Rheumatoid factors

Additional parameters that can be used in human for assessing RA improvement can be according to the American College of Rheumatology (ACR) and include e.g. ACR improvement criteria—ACR20, ACR50 and ACR70 representing the percentage of disease activity improvement (20, 50 or 70%) by the reduction in certain RA symptoms. Thus, for example, ACR20 refers to patients which achieve a 20% improvement in tender and swollen joint counts and 20% improvement in three of the five remaining ACR core set measures.

As the present inventors discovered 3 potential target proteins of the isolated polypeptides and have also shown that addition of one of these proteins (i.e. SAA) can prevent the in-vitro activity of the polypeptide (see Examples 7 and 9 and FIG. 15 in the Examples section which follows) the present invention contemplates the use of a combined treatment comprising the isolated polypeptides or the compositions of matter of the present invention and serum amyloid A (SAA), thranthyretin and/or apolipoproteins B inhibitors.

Thus, according to another aspect of the present invention there is provided a method of treating an inflammatory disease in a subject in need thereof, the method comprising:

(a) administering to the subject a therapeutically effective amount of the isolated polypeptide or the composition of matter of some embodiments of the present invention; and (b) administering to said subject a therapeutically effective amount of an inhibitor of a protein selected from the group consisting of serum amyloid A (SAA), thranthyretin and apolipoproteins B, thereby treating the inflammatory disease in the subject.

According to another aspect there is provided a use of the isolated polypeptide or the composition of matter of some embodiments of the present invention and an inhibitor of a protein selected from the group consisting of serum amyloid A (SAA), thranthyretin and apolipoprotein B for the manufacture of a medicament for the treatment of an inflammatory disease.

According to another aspect of the present invention there is provided an article of manufacture or a kit identified for use in treating inflammatory disease, comprising a packaging material packaging the isolated polypeptides or the composition of matter of some embodiments of the present invention and an inhibitor for a protein selected from the group consisting of SAA, thranthyretin and apolipoproteins B.

According to another aspect of the present invention there is provided a method of treating an inflammatory disease in a subject in need thereof, the method comprising:

(a) administering to the subject a therapeutically effective amount of an isolated polypeptide comprising an amino acid sequence selected form the group consisting of SEQ ID NOs: 1-3, wherein said polypeptide comprises an anti-inflammatory activity; and (b) administering to said subject a therapeutically effective amount of an inhibitor of a protein selected from the group consisting of serum amyloid A (SAA), thranthyretin and apolipoproteins B, thereby treating the inflammatory disease in the subject.

According to another aspect there is provided a use of as isolated polypeptide comprising an amino acid sequence selected from the group consisting of SEQ ID NOs: 1-3, wherein said polypeptide comprises an anti-inflammatory activity; and an inhibitor of a protein selected from the group consisting of serum amyloid A (SAA), thranthyretin and apolipoprotein B for the manufacture of a medicament for the treatment of an inflammatory disease.

According another aspect of the present invention there is provided an article of manufacture or a kit identified for use in treating inflammatory disease, comprising a packaging material packaging the isolated polypeptide comprising an amino acid sequence selected from the group consisting of SEQ ID NOs: 1-3, wherein said polypeptide comprises an anti-inflammatory activity; and an inhibitor for a protein selected from the group consisting of SAA, thranthyretin and apolipoproteins B.

As used herein the term "inhibitor" refers to an agent which downregulates expression and/or activity of a protein (e.g. SAA, thranthyretin and apolipoprotein B) at the genomic (e.g. homologous recombination and site specific endonucleases) and/or the transcript level using a variety of molecules which interfere with transcription and/or translation (e.g., RNA silencing agents e.g. siRNA, shRNA, microRNA) or on the protein level (e.g., aptamers, small molecules and inhibitory peptides, antagonists, enzymes that cleave the polypeptide, antibodies and the like).

Non-limiting example include an antibody which inhibits SAA such as Anti-serum albumin A, an RNA interference targeted to SAA mRNA (see e.g. International Publication Application No: WO 2006071691), an antisense oligonucleotides targeted to apolipoprotein B, such as but not limited to Mipomersen (ISIS-301012, KYNAMRO™), Triazolones as apolipoprotein B synthesis inhibitors (see e.g. U.S. Pat. No. 6,197,972) and an apolipoprotein B secretion inhibitor (see e.g. EP Application Publication No. EP 1099438).

According to a specific embodiment, step (a) is effected prior to step (b).

According to another specific embodiment, step (a) is effected following step (b).

According to yet another specific embodiment, step (a) is effected concomitantly with step (b).

Multiple rounds of administration according to the methods of the present invention and multiple doses of the isolated polypeptide or the composition of matter and the inhibitor can be administered. According to specific embodiments step (a) is effected multiple times. Thus, according to specific embodiments, administration of inhibitor is effected following at least one administration of the isolated polypeptide or the composition of matter. According to specific embodiments step (B) is effected multiple times. Thus, according to specific embodiments, administering the isolated polypeptide or the composition of matter of the present invention is effected following at least one administration of the inhibitor. According to specific embodiments, administering the isolated polypeptide or the composition of matter of the present invention is effected in a sequential order with administration of the inhibitor.

The isolated polypeptide or the composition of matter and the inhibitor may be packaged in the same container or in separate containers; each possibility represents a separate embodiment of the present invention.

According to specific embodiments, the isolated polypeptide or the composition of matter and the inhibitor are in separate formulations.

According to other specific embodiments, the isolated polypeptide or the composition of matter and the inhibitor are in a co-formulation.

The isolated polypeptides, the compositions of matter and the inhibitors of the present invention can be provided to the subject per se, or as part of a pharmaceutical composition where it is mixed with a pharmaceutically acceptable carrier.

Thus, according to an aspect of the present invention there is provided a pharmaceutical composition comprising as an active agent the isolated polypeptide or the composition of matter; and a pharmaceutically acceptable carrier or diluent.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the polypeptide or composition of matter comprising the polypeptide accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, topical, intradermal, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to specific embodiments the route of administration is oral administration.

According to other specific embodiments, the route of administration is into the skin. Methods of administering an active agent into a skin are known in the art and include, for example, intradermal injections, gels, liquid sprays and patches which comprise the active agent and which are applied on the outer surface of the skin.

According to some embodiments of the invention, administration of the active agent into the skin of the subject is performed topically (on the skin).

According to some embodiments of the invention, administration of the active agent into the skin of the subject is performed non-invasively, e.g., using a gel, a liquid spray or a patch (e.g. reservoir type patch and matrix type patch) comprising the active ingredient, which are applied onto the skin of the subject.

It should be noted that in order to increase delivery of the active agent into the skin, the active agent can be formulated with various vehicles designed to increase delivery to the epidermis or the dermis layers. Such vehicles include, but are not limited to liposomes, dendrimers, noisome, transfersome, microemulsion and solid lipid nanoparticles.

According to some embodiments of the invention, administering the is performed by an intradermal injection.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient such as a local injection into the joint. Methods of administering an active agent into the joint are known in the art and include intra-articular injection wherein a hypodermic needle is inserted into the joint to thereby deliver the active agent to the intra-articular space of the intra-articular joint.

As described the polypeptides and compositions of matter of the invention may be used to treat e.g. Alzheimer's disease. Conventional approaches for drug delivery to the central nervous system (CNS) include: neurosurgical strategies (e.g., intrahippocampal (IH), intracranial (IC), intracerebral injection, intracerebroventricular injection (ICV) or infusion or intrathecal administration); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

According to specific embodiments, the pharmaceutical composition is formulated for oral administration.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

The pharmaceutical composition of some embodiments of the invention may also be formulated for sustained-release to provide elevated serum half-life. Such sustained release systems are well known to those of skill in the art and include e.g. microcapsules and nanoparticles. According to specific embodiments, the ProLease biodegradable microsphere delivery system for proteins and peptides (Tracy, 1998, Biotechnol. Prog. 14, 108; Johnson et al., 1996, Nature Med. 2, 795; Herbert et al., 1998, Pharmaceut. Res. 15, 357) a dry powder composed of biodegradable polymeric microspheres containing the protein in a polymer matrix that can be compounded as a dry formulation with or without other agents.

Pharmaceutical compositions suitable for use in context of some embodiments of the invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., RA) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide that the levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The doses shown herein with respect to the mouse animal model can be converted for the treatment other species such as human and other animals diagnosed with the inflammatory disease. Conversion Table approved by the FDA is shown in Reagan-Shaw S., et al., FASEB J. 22:659-661 (2007).

The human equivalent dose is calculated as follows: HED (mg/kg)=Animal dose (mg/kg) multiplied by (Animal $K_m$/human $K_m$).

According to some embodiments of the invention, the isolated polypeptide or the composition of matter is provided at an amount equivalent to a range of from about 2.5-40 mg/kg/day in mice, including any intermediate subranges and values therebetween.

According to specific embodiments the isolated polypeptide or the composition of matter is provided at an amount equivalent to about 3.5 mg/kg/day in mice.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that the therapeutic agents of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Administration of such combination therapy can be simultaneous, such as in a single capsule having a fixed ratio of these active agents, or in multiple capsules for each agent.

Thus, the agents of the present invention can be administered alone with other established or experimental therapeutic regimen to treat inflammatory disease such as non-steroidal anti-inflammatory drugs (NSAID), disease-modifying antirheumatic drugs (DMARDS), corticosteroids, analgesics, Fibromyalgia medications, chemotherapeutic agents and other treatment regimens which are well known in the art.

As mentioned, the present inventors have developed a novel in-vitro assay to test the activity of the peptides and compositions of matter of the present invention. The assay is based on the realization that the RA peptides can reduce survival of fibroblasts isolated from the synovial fluid of an RA patient. Thus, this assay can be used to compare batch to batch variation of manufactured peptides and compositions of matter peptides of the present invention for qualifying the anti-inflammatory activity as well as for testing e.g. stability of the peptides and compositions of matter of the present invention following exposure to environmental conditions such as storage temperature, modifications to the peptides and the formulations.

Thus, according to an aspect of the present invention there is provided a method of determining potency of a batch of the isolated polypeptide, the composition of matter or the pharmaceutical composition of some embodiments of the present invention, the method comprising:

(a) contacting a batch of the isolated polypeptide, the composition of matter or the pharmaceutical composition with fibroblasts obtained from an inflammatory joint of a Rheumatoid arthritis patient; and (b) determining survival of said fibroblasts following a predetermined incubation time, so as to determine the potency of the batch.

According to specific embodiments, the method comprising synthesizing the isolated polypeptide, the composition of matter or the pharmaceutical composition with a modification. Such a modification can be any of the modifications presented hereinabove.

According to specific embodiments, the method is effected in-vitro or ex-vivo.

As used herein, the term "potency" refers to the measure of the biological activity of the product (i.e.; the isolated polypeptide or the composition of matter), based on the attribute of the product which is linked to the relevant biological properties (i.e.; reduced survival of fibroblasts obtained from an RA patient).

As used herein, the term "batch" refers to a specific quantity of a drug that is intended to have uniform character and quality, within specified limits, and is typically produced according to a single manufacturing order during the same cycle of manufacture. Thus, the present teachings can be used in the QA of the manufacturing procedures for assessing the biological activity of the isolated polypeptides, the composition of matter or the pharmaceutical compositions as part of batch qualification.

According to specific embodiments, the term "batch" also refers to a quantity of the drug exposed to stability characterization and/or peptide and formulation modifications.

As used herein, the term "fibroblast" refers to a connective tissue cell that synthesizes the extracellular matrix and collagen and is obtained from a synovial fluid of an RA patient. The fibroblasts used according to the method can be a primary culture directly isolated from an RA patient or cell lines obtained from the fibroblasts such as the commercially available cell lines SW 982, PCS-201-010 and ACS-1023 that can be obtained from the ATCC.

Methods for obtaining a synovial fluid from a subject are well known in the art and include, but are not limited to biopsy such as joint biopsy and joint aspiration. Typically, procedures for obtaining tissue or fluid biopsies are described in details in Hypertext Transfer Protocol://World Wide Web (dot) healthatoz (dot)com/healthatoz/Atoz/search.asp.

Specifically, a joint aspiration, also known as Arthrocentesis refers to the removal of fluid from the space around a joint using a needle and syringe. This is usually performed under a local anesthetic to either relieve swelling or to obtain fluid for analysis to diagnose a joint disorder and/or problem. Joint aspiration is usually performed on the knee; however, fluid can also be removed from other joints, such as the hip, ankle, shoulder, elbow, or wrist.

A joint biopsy refers to joint or synovial biopsy. In the procedure a sample of the joint lining or synovial membrane or fluid is taken. Briefly, the procedure is effected in a clinical facility by a surgeon. A number of approaches are available to perform this biopsy: such as through an incision in the joint; with a scope inserted in the joint; or, more typically, by the insertion of a sharp instrument through the skin. The sample can be taken from any joint, typically the examined joint is the knee. A sharp instrument (trocar) is pushed into the joint space. A needle with an attached syringe is inserted into the joint to withdraw fluid for laboratory analysis. The surgeon may instill analgesic compounds into the joint and along the needle track before the needle is withdrawn. The trocar and then the biopsy needle is inserted and specimens taken. After the specimen is taken, both the trocar and the biopsy needle are removed.

Regardless of the procedure employed, once the biological sample is obtained, the fibroblast may be further isolated. Enrichment of fibroblasts populations can be obtained by methods well known in the art, and included those disclosed in e.g. Bendersky et al, J Immunol.; 188:4349-59, 2012, magnetic cell separation and flow cytometry cell sorting.

Thus, for example the fibroblasts can be isolated by culturing adherent synovial fluid cells in plastic wells in DMEM-supplemented medium for about 48 hours followed by removal of all of the nonadherent cells. The adherent cells which comprise fibroblasts typically display a fibroblastic morphology and express CD90, low levels of the CD49a integrin, negative for macrophage (CD14), T cell (CD3), and B cell (CD20) surface markers (as determined by e.g. flow cytometry) and stain positively for collagen type I determined by Sirius red staining.

The primary culture of fibroblasts comprises according to specific embodiments at least 10%, at least 20%, at least 30%, at least 40%, at least 50%, at least 60%, at least 70%, at least 80%, at least 90% or more fibroblasts.

Following preparation of the fibroblasts, predetermined amount of cells are incubated in tissue culture plates (e.g.; 12, 24, 96, 384 wells plates) with the appropriate Growth medium and stimulated with a predetermined amount of the tested isolated polypeptide, the composition of matter or the pharmaceutical composition. Selection of the medium is well within the capabilities of skilled in the art. Thus, for example, RPMI or DMEM (can be obtained for example from Sigma-Aldrich or Biological Industries, Beit Haemek, Israel) can be used as a growth medium. The medium may be supplemented with L-glutamine, non-essential amino acids, sodium pyruvate, antibiotic/antimycotic solution, 2-mercaptoethanol and serum.

Selection of the predetermined amount of cells incubated for in-vitro testing that will result in detectable effect on cell survival is well within the capabilities of the skilled in the art. Thus, for example cell concentration can be $1\times10^4$/ml to $5\times10^6$/ml; $1\times10^4$/ml to $1\times10^6$/ml; $5\times10^4$/ml to $5\times10^6$/ml; $1\times10^5$/ml to $5\times10^6$/ml; or $1\times10^5$/ml to $1\times10^6$/ml.

According to specific embodiments the cell concentration is $2\times10^5$/ml.

Selection of the peptide or composition of matter concentration used for the in-vitro testing that will result in detectable effect on cell survival is well within the capabilities of skilled in the art. Preferably, the concentration used should be within the linear range of the selected stimulation parameter. Thus, for example, the concentration can be 1 μg/ml to 30 μg/ml; 1 μg/ml to 20 μg/ml; 5 μg/ml to 30 μg/ml; or 5 μg/ml to 20 μg/ml.

The number of tested concentration can be at least 1, at least 2, at least 3, at least 5, at least 6, 1-10, 2-10, 3-10, 5-10, 1-5, 2-5 and 3-5 different concentrations.

The number of samples repeats for each of the tested concentration can be 2, 3, 4, 5 or 6 repeats.

Following a pre-determined incubation time the survival of the fibroblasts is determined. Specific methods of monitoring cell survival are known in the art and include for example, the MTT test which is based on the selective ability of living cells to reduce the yellow salt MTT (3-(4, 5-dimethylthiazolyl-2)-2, 5-diphenyltetrazolium bromide) (can be obtained for example from Sigma, Aldrich) to a purple-blue insoluble formazan precipitate; Apoptosis assays such as the TUNEL assay (can be obtained for example from Roche); and the Annexin V assay [for example ApoAlert® Annexin V Apoptosis Kit (Clontech Laboratories, Inc., CA, USA)].

The incubation time may vary and determination of the incubation time that will result in detectable effect on cell survival is well within the capabilities of skilled in the art. According to a specific embodiment, the incubation time is between 12 hours to 96 hours. According to some embodiments of the invention, the incubation time is between 12 to 72 hours; 12 to 48 hours; 12 to 24 hours; 24 to 96 hours, 24 to 72 hours or 24 to 48 hours. According to specific embodiments of the invention, the incubation time is between 24-48 hours.

According to specific embodiments, reduced survival of the fibroblasts following said contacting is indicative that the batch is potent.

According to specific embodiments the assay may further include positive and negative control samples. The positive control for the assay may include agents inducing non-specific fibroblasts cell death, for example ascorbate (see e.g. Schmidt et al., J Biomed Mater Res. 1993 April; 27(4):521-30).

Negative control for the assay may include agents which prevent the biological activity of the tested polypeptide or composition of matter such as SAA (can be obtained for example from PeproTech).

According to specific embodiments, the method comprising comparing the survival of the cells with survival of the cells following contacting with a reference standard batch of the isolated polypeptide, composition of matter or the pharmaceutical composition, so as to determine the relative potency of the batch.

As used herein, the term "relative potency" refers to a qualitative measure of potency of a batch of the isolated polypeptide, composition of matter or the pharmaceutical composition, relatively to a standard reference (RS) of the isolated polypeptide, composition of matter or the pharmaceutical composition, having a known potency.

According to specific embodiments the potency of a batch of the isolated polypeptide, composition of matter or the pharmaceutical composition, is determined relatively to the known potency of a reference standard (RS).

As used herein, the phrase "reference standard" or "RS" refers to a standardized isolated polypeptide, composition of matter or pharmaceutical composition, which is used as a measurement base for the isolated polypeptide, composition of matter or the pharmaceutical composition. RS provides a calibrated level of biological effect against which new preparations of the isolated polypeptide, composition of matter or the pharmaceutical composition can be compared to.

According to a specific embodiment, the RS is characterized by optimum potency and quality of an active component that is effective in treating the disease (e.g., RA).

Calculating potency and relative potency are known in the art. According to specific embodiments the relative potency is calculated using a software suitable for biological assays, such as parallel line analysis software e.g., PLA (Stegmann Systems GmbH) and Gen5 data analysis software (BioTek).

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Peptide Synthesis and Characterization

Materials and Methods
Synthesis of 5, 7 and 9 Mer Peptides—
The 5-, 7- and 9-mer peptides [MTADV (SEQ ID NO: 1), MTADVDR (SEQ ID NO: 2) and TRMTADVDR (SEQ ID NO: 3)], −3, the Acylated-N and Amidated-C termini 5-, 7- and 9-mer peptides [Ac-MTADV-NH2 (SEQ ID NO: 4), Ac-MTADVDR-NH$_2$ (SEQ ID NO: 5) and Ac-TRMTADVDR-NH$_2$ (SEQ ID NO: 6)] and the scrambled 7-mer peptide [Ac-TMDVADR-NH$_2$ (SEQ ID NO: 7)], were synthesized by Sigma Israel using solid phase synthesis fmoc chemistry. A purity of 95- to 97% was reached.

Liquid Chromatography-Mass Spectrometry (LCMS)—
Stability, Pharmacokinetic (PK) and target proteins of the peptide were evaluated by LCMS.

Sample Preparation for Mass Spectrometry:
The protein-bound beads were reduced with 2.8 mM DTT (60° C. for 30 min) and modified with 8.8 mM iodoacetamide (at room temperature for 30 min under dark conditions) in 8M Urea and 400 mM Ammonium bicarbonate. The proteins were digested in 2M Urea, 25 mM ammonium bicarbonate with modified trypsin (Promega) at a 1:50 enzyme-to-substrate ratio, overnight at 37° C. The tryptic peptides were desalted using C18 tips (Harvard) dried and re-suspended in 0.1% Formic acid Mass Spectrometry measurements. The resulting tryptic peptides were analyzed by LC-MS/MS using an OrbitrapXL mass spectrometer (Thermo-Fisher) fitted with a capillary HPLC (Eksigent). Specifically, the peptides were loaded onto a C18 trap column (0.35 mm, LC-Packings) connected on-line to a homemade capillary column (75 micron ID) packed with Reprosil C18-Aqua (Dr Maisch GmbH, Germany) and resolved using linear 94 minutes 5 to 40% acetonitrile gradients followed by 12 minutes at 95% acetonitrile in the presence of 0.1% formic acid in water at flow rates of 0.25 μl/min. Mass spectrometry was performed in a positive mode using repetitively full MS scan (resolution 60000) followed by collision induces dissociation (CID). Top seven, (>1 charged peptides, 350-2000 M/Z) were selected for fragmentation from each full mass spectrum.

Data Analysis:

The mass spectrometry was analyzed using the Discoverer software version 1.4 against the human uniprot database and against decoy databases (in order to determine the false discovery rate (FDR), using the Sequest and Mascot search engines. High confidence refers to 0.01 FDR.

Semi quantitation was performed by calculating the peak area of each peptide. The area of the protein is the average of the three most intense peptides from each protein.

Results

Inclusion of alanine in the splicing junction between variant exon 4 and variant exon 5 of CD44vRA variant leading to the presence of the MTADV sequence instead of the original MTDV sequence was shown to confer the pathological activity of CD44vRA (Nedvetzki et al., J Clin Invest 111:1211-1220, 2003).

The present inventors have synthesized 5-, 7-, and 9-mer peptides (denoted herein as RA peptides) including the MTADV sequence. The 5-mer RA peptide comprises a relative hydrophobic amino acid sequence as well as a low molecular weight (less than 700 Dalton). Therefore, it may easily penetrate into tissues and consequently may be used in topical applications and oral delivery.

Figure 1:
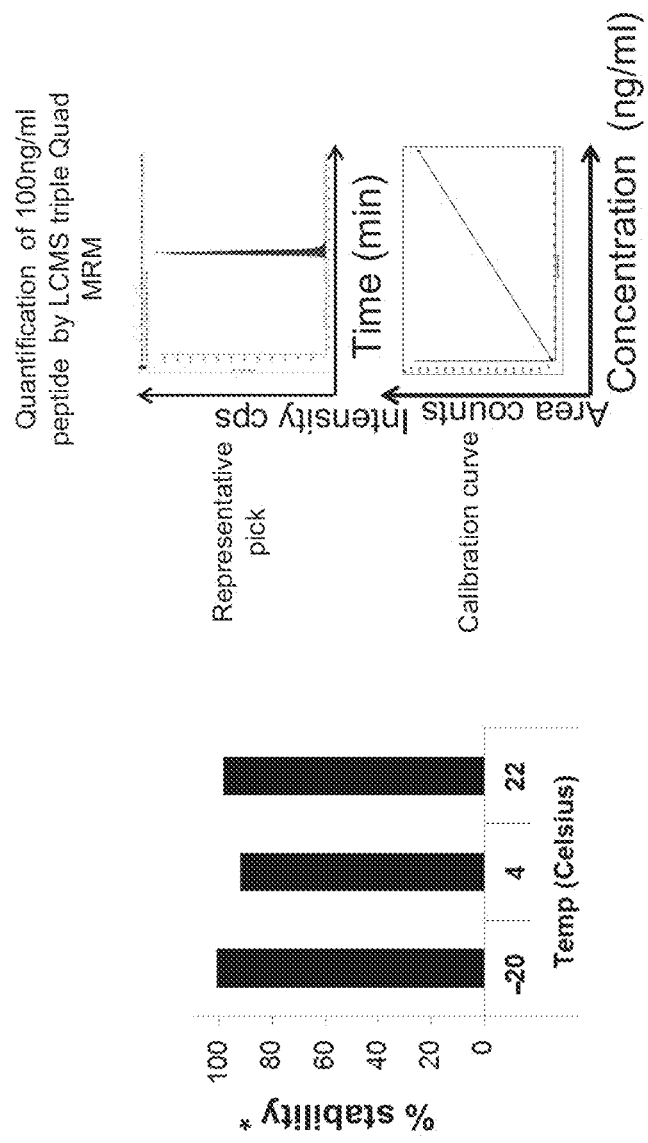

The proteolytic analysis of the RA peptides demonstrated no proteolytic sites (data not shown), indicating that the peptides are at least relatively stable. Quantification analysis by Mass Spectrometry indicated almost identical stability of the 5-mer peptide (SEQ ID NO: 1) upon storage in saline at 4° C., at room temperature or at −20° C. for 22 weeks (FIG. 1). Assuming that storage at −20° C. displays 100% stability, these results demonstrate that the 5-mer peptide is stable for at least 22 weeks at room temperature and 4° C.

Example 2

The 5- and 9-Mer RA Peptides can Reduce Joint Inflammation in the Collagen-Induced Arthritis (CIA) Mouse Model Materials and Methods Mice—

Collagen-induced arthritis (CIA) was generated in DBA/1 or C57BL mice by injection of type II collagen as described in Nedvetzki et al., PNAS 101, 18081-18086, 2004.

Treatment Protocol—

PBS, or the 9-mer RA peptide (SEQ ID NO: 3) at a dose of 25 μg, 100 μg or 150 μg per injection was administered i.p to CIA mice for 4 times within 6 days (see Table 3 below). PBS (n=7), or 5-mer RA peptide (SEQ ID NO: 1, n=7) at a dose of 70 μg per injection were administered i.p to CIA mice on C57BL/6 background for 10 consecutive days. In all groups first injection was given at the onset of disease as determined by paw swelling.

Evaluation of Joint Inflammation—

Inflammation was evaluated by the paw swelling response. Paw swelling was measured by micro caliber. Paw swelling at range of 2.1-2.3 mm was considered "onset of disease" and the starting point for injection of the peptides. Mice that showed above 2.3 mm paw swelling were excluded from the experiment. All measurements were performed under blind manner (For additional details see Nedvetzki, et al., (2004) PNAS 101, 18081-18086).

Histology—

Mice were sacrificed on day 11 (one day following cessation of treatment) and hind limbs were isolated and fixed overnight with 4% paraformaldehyde at room temperature (for additional details see Nedvetzki et al. (2004) PNAS 101, 18081-18086). Following fixation, diarthrodial Joint sections were prepared, stained with Hematoxylin and Eosin (H&E) and evaluated by a pathologist under blind manner. Joint infiltration score: 0=no infiltration; 4=massive infiltration.

Statistical Analysis—

Statistical analysis for each measurement point was performed by the Student's t-test for unpaired values.

TABLE 3

Experimental design-dose response (FIGS. 2A-C)

| Group # | Treatment | #Mice | Injection protocol |
|---|---|---|---|
| 1 | 1XPBS 100 μl/injection | 8 | Injection every other day for 6 constitutive days |
| 2 | Peptide 9 mer TRMTADVDR (SEQ ID NO: 3) 25 μg/100 μl/injection | 8 | Injection every other day for 6 constitutive days |
| 3 | Peptide 9 mer TRMTADVDR (SEQ ID NO: 3) 100 μg/100 μl/injection | 6 | Injection every other day for constitutive days |
| 3 | Peptide 9 mer TRMTADVDR (SEQ ID NO: 3) 150 μg/100 μl/injection | 4 | Injection every other day for 6 constitutive days |

Results

The collagen-induced arthritis (CIA) mouse model is the mouse analogue of human Rheumatoid Arthritis (RA). To evaluate the effect of the generated RA peptides on joint inflammation in the CIA mouse model different dosages of the 9-mer RA peptide (SEQ ID NO: 3) were administered to CIA mice on DBA/1 background starting from the onset of disease; and joint inflammation was evaluated by determining paw swelling. As shown in FIGS. 2A-B, mice that received 25 and 100 μg of the 9-mer RA peptide (SEQ ID NO: 3) did not show significant difference in paw swelling response as compared to mice administered with PBS, implying lack of a significant therapeutic effect. In contrast, mice that received 150 μg of the 9-mer RA peptide (SEQ ID NO: 3) had demonstrated significant reduction in paw swelling (FIG. 2C).

Histological evaluation of hind limbs sections taken from CIA mice on C57BL/6 background following treatment with the PBS control revealed massive infiltration of mononuclear inflammatory cells into the joint capsule, extensive synovial hypertrophy and severe narrowing of the joint space which was filled with reactive cells. In addition, severe erosion of the articular cartilage and the subchondral bone, with destruction of cartilage matrix, was noted. The remaining cartilage matrix was heavily infiltrated as well. Taken together, the average joint Infiltration score in the PBS treated mice=about 4 (FIGS. 3A and 3C).

On the contrary, histological evaluation of hind limbs sections taken from CIA mice following treatment with the 5-mer RA peptide (SEQ ID NO: 1) revealed none-to-mild infiltration of mononuclear inflammatory cells into the joint capsule with either no or mild synovial hypertrophy Inflammatory infiltrate was noted in minority of the samples. The joint space was preserved, with few reactive cells if any. In addition, no erosion of the articular cartilage and the subchondral bone was noted and the cartilage matrix was generally preserved. Furthermore, few of the samples were indistinguishable from unaffected mice (data not shown). Taken together, average joint infiltration score in the 5-mer RA peptide treated mice=about 1 (FIGS. 3B and 3C).

Overall, the joint inflammation score of the control PBS treated group was significantly higher (P<0.0001) than that of the 5-mer RA peptide (SEQ ID NO: 1) treated group, indicating that treatment with the peptide can highly restore normal histology of the inflamed joint.

Taken together, treatment with the 5- and 9-mer RA peptides (SEQ ID NOs: 1 and 3) inhibit joint inflammation in the CIA mouse model.

Without being bound by theory it is suggested that an interaction between unknown CD44vRA ligand and CD44vRA create a conformational change of CD44vRA glycoprotein. This new epitope allows binding of FGF-2 to the heparin sulfate of v3 exon product resides in the same molecule. The bound FGF-2 is oriented to interact with endothelial cells or fibroblasts expressing FGF receptor 1, resulting in their proliferation and exaggeration of the inflammatory activity (Nedvetzki et al., J Clin Invest 111: 1211-1220, 2003). The RA peptide may compete with the cell surface CD44 on the interaction with the unknown ligand resulting in blockade of the FGF-2-induced inflammatory cascade described by Nedvetzki et al. (J Clin Invest 111:1211-1220, 2003).

Example 3

The 5-7- and 9-Mer Protected RA Peptides can Reduce Joint Inflammation in the CIA Mouse Model Materials and Methods
Mice—
As described in Example 2 above.
Treatment Protocol—
PBS, or the tested peptides [Ac-TRMTADVDR-NH2 (SEQ ID NO: 6), Ac-MTADVDR-NH2 (SEQ ID NO: 5), Ac-MTADV-NH$_2$ (SEQ ID NO: 4) and scrambled Ac-TMDVADR-NH$_2$ (SEQ ID NO: 7)] at doses of 70 or 200 μg per injection were administered i.p to CIA/1 mice on DBA background for 9-10 consecutive days (see Tables 4-7 below). As a non-specific control, several mice were administered I.P. with Dexamethsone (Dex) at a dose of 50 μg, following the same protocol. In all groups first injection was given at the onset of disease as determined by paw swelling.
Evaluation of Joint Inflammation—
As described in Example 2 above. Paw swelling of less than 2 mm was considered healthy.
Statistical Analysis—
As described in Example 2 above.

TABLE 4

Experimental design (FIG. 4)

| Group # | Treatment | #Mice/paws* | Injection protocol |
|---|---|---|---|
| 1 | PBSx1 100 μl/injection | 4/5* | One injection per day for 9 constitutive days |
| 2 | Peptide 9 mer Ac-TRMTADVDR-NH2 (SEQ ID NO: 6) 200 μg/100 μl/injection | 5/7* | One injection per day for 9 constitutive days |
| 3 | Peptide 7 mer Ac-MTADVDR-NH2 (SEQ ID NO: 5) 200 μg/100 μl/injection | 2/3* | One injection per day for 9 constitutive days |

*When the two hind paws of a mouse were inflamed, both paws were analyzed for swelling

TABLE 5A

Experimental design (FIG. 5A)

| Group # | Treatment | #Mice | Injection protocol |
|---|---|---|---|
| 1 | 1XPBS 100 μl/injection | 3 | One injection per day for 9 constitutive days |
| 2 | Peptide 5 mer Ac-MTADV-NH2 (SEQ ID NO: 4) 200 μg/100 μl/injection | 5 | One injection per day for 9 constitutive days |
| 3 | Dexamethasone (Dex) | 4 | One injection per day for 9 constitutive days |

TABLE 5B

Experimental design (FIG. 5B)

| Group # | Treatment | #Mice/Paws* | Injection protocol |
|---|---|---|---|
| 1 | 1XPBS 100 μ/injection 1 | 10/11* | One injection per day for 10 constitutive days |
| 2 | Peptide 5 mer Ac-MTADV-NH2 (SEQ ID NO: 4) 200 μg/100 μl/injection | 11/16* | One injection per day for 10 constitutive days |

*When the two hind paws of a mouse were inflamed, both paws were analyzed for swelling

TABLE 6

Experimental design (FIG. 6)

| Group # | Treatment | #Mice | Injection protocol |
|---|---|---|---|
| 1 | 1XPBS 100 μ/injection 1 | 13 | One injection per day for 10 constitutive days |
| 2 | Peptide 5 mer Ac-MTADV-NH2 (SEQ ID NO: 4) 70 μg/100 μl/injection | 11 | One injection per day for 10 constitutive days |

TABLE 7

Experimental design (FIGS. 7A-C)

| Group # | Treatment | #Mice/Paws* | Injection protocol |
|---|---|---|---|
| 1 | 1XPBS 100 μl/injection | 8/9* | One injection per day for 9 constitutive days |
| 2 | Control: 7-mer scrambled Peptide Ac-TMDVADR-NH$_2$ (SEQ ID NO: 7) 200 μg/100 μl/injection | 7/10* | One injection per day for 9 constitutive days |
| 3 | Peptide 7-mer Ac-MTADVDR-NH$_2$ (SEQ ID NO: 5) 200 μg/100 μ/injection 1 | 9/11* | One injection per day for 9 constitutive days |

*When the two hind paws of a mouse were inflamed, both paws were analyzed for swelling Results In the next step 9-7- and 5-mer RA peptides were synthesized with protection residues, namely Acetyl and Amide residues at the amino and carboxyl terminal ends of the peptides [Ac-TRMTADVDR-NH$_2$ (SEQ ID NO: 6), Ac-MTADVDR-NH$_2$ (SEQ ID NO: 5) and Ac-MTADV-NH$_2$ (SEQ ID NO: 4), denoted herein as 9-7- and 5-mer RA protected peptide, respectively]. These protection residues preserve the natural stage of the peptide in the experimental mouse and stabilize the peptide. The ability of the protected peptides to reduce joint inflammation in DBA/1 mice following their injection at the onset of CIA was evaluated. All measurements were performed under blind manner.

As can be seen in FIGS. 4 and 5A-B injection of all protected RA peptides at a dose of 200 μg per injection significantly inhibited joint inflammation in the CIA mice on DBA background, as compared to mice treated with PBS. As also evident in FIG. 5A, administration of Dexamethasone decreased footpad swelling as well, possibly by generating a non-specific anti-inflammatory effect of this steroid. The 5-mer protected peptide (SEQ ID NO: 4) was also able to significantly inhibit joint inflammation in the CIA mice on C57BL/6 background when administered at a dose of 70 μg per injection (FIG. 6). All measurements were performed under blind manner.

In the next step, the effect of a scrambled RA peptide on joint inflammation was evaluated. To this end the effect of the 7-mer protected RA peptide (Ac-MTADVDR-NH$_2$, SEQ ID NO: 5) was compared to the effect of a 7-mer scrambled protected peptide (Ac-TMDVADR-NH$_2$, SEQ ID NO: 7). As shown in FIGS. 7A-C, the scrambled non-specific 7-mer protected peptide had no effect on footpad swelling. All measurements were performed under blind manner.

The results shown in FIGS. 7A-C were also evaluated by determining the percent of healthy paws in each group. Hence, evaluation of the hind paws of the CIA DBA/1 mice (FIG. 8), reflecting the severity of the disease, showed that more than 60% of the hind paws in CIA mice treated with the 7-mer protected RA peptide remained healthy. In comparison, the percentages of the hind paws that remained healthy in the other groups tested were 15% in the PBS treated group and 33% in the 7-mer peptide scrambled group.

Taken together, 5-, 7- and 9-mer RA protected peptides (SEQ ID NOs: 4-6) inhibit joint inflammation upon injection to CIA mice on both DBA and C57BL/6 background, while non-specific scrambled 7-mer protected peptide (SEQ ID NO: 7) has no effect on joint inflammation. Acetylation and Amidation did not affect the activity of the RA peptides (data not shown); however, they are expected to improve stability and pharmacokinetics of the RA peptide.

Example 4

70 μg Per Injection is the Optimal Dose for the 5-Mer Protected RA Peptide for Reducing Joint Inflammation in the CIA Mouse Model Materials and Methods
Mice—
As described in Example 2 above.
Treatment Protocol—
PBS, or the tested peptide [Ac-MTADV-NH$_2$ (SEQ ID NO: 4)] at doses of 10, 25, 70, 200 or 600 μg per injection were administered i.p to CIA mice for 10 consecutive days (see Tables 8-9 below). In all groups first injection was given at the onset of disease as determined by paw swelling.
Evaluation of Joint Inflammation—
As described in Example 2 above. The measurements were effected under blind manner.
Statistical Analysis—
As described in Example 2 above.

TABLE 8

Experimental design (FIG. 9A)

| Group # | Treatment | #Paws | Injection protocol |
|---|---|---|---|
| 1 | 1XPBS 100 μl/injection | 13 | One injection per day for 10 constitutive days |
| 2 | 5 mer Peptide Ac-MTADV-NH$_2$ (SEQ ID NO: 4) 70 μg/100 μl/injection | 11 | One injection per day for 10 constitutive days |
| 3 | 5 mer Peptide Ac-MTADV-NH$_2$ (SEQ ID NO: 4) 200 μg/100 μl/injection | 11 | One injection per day for 10 constitutive days |
| 4 | 5 mer Peptide Ac-MTADV-NH$_2$ (SEQ ID NO: 4) 600 μg/100 μl/injection | 9 | One injection per day for 10 constitutive days |

TABLE 9

Experimental design (FIG. 9B)

| Group # | Treatment | #Paws | Injection protocol |
|---|---|---|---|
| 1 | 1XPBS 100 μl/injection | 13 | One injection per day for 10 constitutive days |
| 2 | 5 mer Peptide Ac-MTADV-NH$_2$ (SEQ ID NO: 4) 10 μg/100 μl/injection | 11 | One injection per day for 10 constitutive days |
| 3 | 5 mer Peptide Ac-MTADV-NH$_2$ (SEQ ID NO: 4) 25 μg/100 μl/injection | 11 | One injection per day for 10 constitutive days |
| 4 | 5 mer Peptide Ac-MTADV-NH$_2$ (SEQ ID NO: 4) 70 μg/100 μl/injection | 9 | One injection per day for 10 constitutive days |

Results

To evaluate the optimal anti-inflammatory therapeutic dose of the 5-mer RA peptide, several different doses of the protected peptide (SEQ ID NO: 4) were administered to CIA mice on C57BL/6 background and joint inflammation was determined by footpad swelling measurements (electronic automatic measurements of the volume of the footpad, based on Archimedes observation). As can be seen in FIG. 9A, injection of 70, 200 or 600 μg per injection of the 5-mer protected RA peptide (SEQ ID NO: 4) reduced the joint inflammation when compared to PBS control; however, a dose of 70 μg of the peptide generated the most statistically significant anti-inflammatory effect. In addition, as shown in FIG. 9B, injection of 10 and 25 μg per injection of the 5-mer protected RA peptide (SEQ ID NO: 4) did not induce a significant anti-inflammatory effect.

Taken together, the data indicates that a dose of 70 μg per injection is the optimal and the lowest dose for CIA inhibition by the 5-mer protected RA peptide (SEQ ID NO: 4).

Example 5

The 5-Mer RA Peptide does not Inhibit DTH in the CIA Mouse Model

Materials and Methods
DTH Model—
C57BL/6 mice were painted at their abdomen with oxazolone solution (sensitization). On day 6, the right ear of each mouse was painted with the same hapten, oxazolone (elicitation), to generate delayed type hypersensitivity (DTH) response. The differences in thickness between the right and the left ears, indicating DTH development, were determined by microcaliper 24 hours later. DTH induction indicates a normal immune response. For additional details see Weiss et al., (2000) Proc. Natl. Acad. Sci. USA. 97, 285-290.

Treatment Protocol—

PBS and 5-mer peptide (SEQ ID NO: 1) at a dose of 200 µg was administered one day before the sensitization and then every day during the sensitization period (7 days). An anti-TNF antibody (Herrring at al., (2002) Infect Immun 70, 2959-64) was used for comparison, to demonstrate non-specific effect.

Statistical Analysis—

As described in Example 2 above.

Results

To evaluate the influence the RA peptides on the immune response in general the effect of the 5-mer RA peptide (SEQ ID NO: 1) on delayed type hypersensitivity (DTH) response was evaluated in a DTH model generated in C57BL/6 mice. DTH reflects acute inflammation, characterizing immune response against microorganism. The results indicate that injection of the 5-mer RA peptide did not affect the DTH response and mice treated with the peptide displayed the same DTH response as the control mice treated with PBS, throughout the 7 days assay period (FIG. 10). In comparison mice treated with anti-TNFα antibody displayed inhibited DTH response, which was significant compared to the control mice.

Example 6

The 5-Mer Peptide does not Generate Neutralizing Antibodies in the CIA Mouse Model Materials and Methods Mice—

As described in Example 2 above.

Treatment Protocol—

PBS, or 5-mer RA peptide (SEQ ID NO: 1) at a dose of 70 µg per injection were administered i.p to CIA mice on C57BL/6 background for 10 consecutive days. In all groups first injection was given at the onset of disease as determined by paw swelling.

ELISA—

96 wells ELISA plates were coated with 5-mer RA peptide (SEQ ID NO: 1), collagen or immunoglobulin (positive control). Serum from CIA mice treated with PBS or the 5-mer RA peptide was added to the coated plates and the presence of neutralizing antibodies against collagen or the RA peptide was detected with anti-immunoglobulin+ detection system. The plate wells were coated with 1 mg/ml peptide or protein. Mouse serum was added to the plate wells for 15 hours in cold temperature. The detection system included HRP-anti-mouse IgG and TMB (Bako) substrate. Plates were analysed using an ELISA reader at a wave length of 450 nm.

Statistical Analysis—

As described in Example 2 above.

Results

To determine whether treatment with the RA peptides induces production of specific neutralizing antibodies that may reduce or even block the peptide anti-inflammatory effect the abundance of anti-5-mer peptide antibodies in the serum was determined using an ELISA assay. As shown in FIG. 11, no neutralizing antibodies to the 5-mer RA peptide (SEQ ID NO: 1) were detected in the serum of CIA mice following treatment with the peptide. Contrary, as the CIA mouse model is generated by collagen injection, anti-collagen specific antibodies were clearly evident in the serum of the CIA mice.

Example 7

Serum Amyloid A, Transthyretin and Apolipoprotein B are Potential Target Proteins of the 5-Mer Peptide Materials and Methods Separation of Peptide Target Protein(s)—

Synovial fluid was removed from the joint of a Rheumatoid Arthritis (RA) patient. The synovial fluid was diluted 1:1 with PBS and centrifuged at 1,200 rpm. The cell pellet was subjected to lysis buffer containing protease inhibitors. The cell lysate was incubated with a biotinylated 5-mer peptide (Sigma) or with PBS for 12 hour at 4° C., with shaking. Streptavidin Sepharose beads (Sephdex) were added to the biotinylated 5-mer peptide-treated cell extract or PBS-treated cell extract for additional one hour at 4° C., with shaking. The peptide-bound beads and the control beads were separated by centrifugation, extensively washed and sent for mass spectrometry analysis, see FIG. 12. The mass spectrometry (MS) measurements and analysis were performed in the Smoler Proteomic Research Center at the Technion in Haifa.

Results

Mass spectrometry analysis of proteins from cell lysates extracted from synovial fluid cells of an RA patient that bound the 5-mer peptide (SEQ ID NO: 1) identified Serum Amyloid A (SAA), Transthyretin and Apolipoprotein B as potential target proteins of the 5-mer RA peptide (SEQ ID NO: 1). The indicated proteins are known to be involved in the pathology of RA but also in the pathologies of Alzheimer's disease, cancer diseases and cardiovascular disease.

Example 8

Pharmacokinetics of the 5-Mer RA Peptide

Materials and Methods

Treatment Protocol—

C57BL/6 mice were subjected to a single i.p. injection of 200 µg 5-mer peptide (SEQ ID NO: 1). Blood samples were taken by terminal bleeding (500-1000 µl) 15, 35, and 60 minutes following injection and the serum was sent for mass spectrometry evaluation.

Mass Spectrometry Analysis—

The concentration of the 5-mer RA peptide in the blood was determined by mass spectrum analysis as described above.

Results

The pharmacokinetic (PK) of the 5-mer RA peptide elimination in the blood of mice following a single i.p. injection is shown in FIG. 13.

Example 9

An In Vitro Model for Evaluating the Effect of the RA Peptides

Materials and Methods

Cells—

Fibroblasts from the inflammatory joint of an RA patient were cultured and maintained as shown in Bendersky et al, J Immunol.; 188:4349-59, 2012. A quantity of 20,000 cells was added to each one of the 96 well plates with the indicated concentrations of peptide, serum amyloid A or α-lactalbumin.

MTT Assay—

MTT assay was effected as shown in Madhyastha et al. (2015) J Clin Diagn Res.; 9:ZC05-8.

Statistical Analysis—

As described in Example 2 above.

Results

An in-vitro model was developed as a tool to evaluate the biological activity of the generated RA peptides. To this end, fibroblasts from the inflammatory joint of an RA patient were incubated in-vitro and the effect of the peptides on cell survival was evaluated by a MTT assay.

As shown in FIG. 14, increasing the dose of the 5-mer RA peptide (SEQ ID NO: 1) gradually inhibits cell survival. Addition 50 µg/ml Serum Amyloid A (SAA) into the fibroblast culture in combination with the 5-mer peptide prevents this inhibition. The results also indicate that a low dose of 2.5 µg/ml (~5 nM) of the peptide is able to significantly inhibit cell survival in this in-vitro model, and that the in-vitro maximal suppressive effect is 60%.

In order to demonstrate the specificity of the effect of the peptide on cell survival, the peptide was added to the cell culture at a constant concentration (25 µg/ml) and SAA or lactalbumin (LA, a control protein with similar molecular weight) was added at excalating concentrations. As shown in FIG. 15, the 5-mer peptide reduced survival of the fibroblast and addition of SAA gradually prevented this reduction in a dose response manner. In contrast, the addition of LA had no effect on the suppressive activity the peptide; indicating the SAA prevents the inhibitory effect of the 5-mer peptide in a specific manner.

In the next step, the suppressive effect of the 5-mer protected RA peptide (SEQ ID NO: 4) was compared to the 5-mer RA peptide (SEQ ID NO: 1). As shown in FIG. 16, peptide modification improved the suppressive effect of the peptide.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A 5 amino acid peptide modified at the N- and/or C-terminus, wherein the peptide consists of SEQ ID NO: 1 and has an anti-inflammatory activity.

2. The peptide of claim 1, wherein said peptide is modified at the N terminus.

3. The peptide of claim 2, wherein said peptide is modified at the N terminus with an Acetyl.

4. The peptide of claim 1, wherein said peptide is modified at the C terminus.

5. The peptide of claim 4, wherein said peptide is modified at the C terminus with an Amide.

6. The peptide of claim 1, being as set forth in SEQ ID NO: 4.

7. A composition of matter comprising an isolated peptide consisting of SEQ ID NO: 1 and a non-proteinaceous moiety attached to said isolated peptide, wherein the composition of matter comprises an anti-inflammatory activity.

8. The composition of matter of claim 7, wherein said attached is covalent attachment.

9. The isolated peptide of claim 1, wherein said anti-inflammatory activity is not dependent on vaccination or mucosal tolerance.

10. The isolated peptide of claim 1, being capable of binding a protein selected from the group consisting of serum amyloid A, Transthyretin and apolipoprotein B.

11. A pharmaceutical composition comprising as an active agent the isolated peptide of claim 1; and a pharmaceutically acceptable carrier or diluent.

12. The isolated peptide of claim 1, being capable of binding serum amyloid A.

* * * * *